(12) United States Patent
Sheng et al.

(10) Patent No.: US 10,106,508 B2
(45) Date of Patent: Oct. 23, 2018

(54) QUINAZOLINE HETEROCYCLIC COMPOUND AS EGFR KINASE INHIBITOR AND PREPARATION AND APPLICATION THEREOF

(71) Applicant: BEIJING SCITECH-MQ PHARMACEUTICALS LIMITED, Beijing (CN)

(72) Inventors: Wang Sheng, Beijing (CN); Leifu Yang, Beijing (CN); Zhiyong Pan, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 0 days.

(21) Appl. No.: 15/541,026

(22) PCT Filed: Jan. 12, 2016

(86) PCT No.: PCT/CN2016/070736
§ 371 (c)(1),
(2) Date: Jun. 30, 2017

(87) PCT Pub. No.: WO2016/112847
PCT Pub. Date: Jul. 21, 2016

(65) Prior Publication Data
US 2017/0355683 A1  Dec. 14, 2017

(30) Foreign Application Priority Data
Jan. 13, 2015 (CN) ............... 2015 1 0015411

(51) Int. Cl.
C07D 239/94 (2006.01)
C07D 491/056 (2006.01)
C07D 498/04 (2006.01)
A61K 31/357 (2006.01)
A61K 31/517 (2006.01)
A61K 31/5375 (2006.01)
A61K 39/395 (2006.01)
C07D 405/14 (2006.01)
A61P 35/02 (2006.01)

(52) U.S. Cl.
CPC .......... *C07D 239/94* (2013.01); *A61K 31/357* (2013.01); *A61K 31/517* (2013.01); *A61K 31/5375* (2013.01); *A61K 39/3955* (2013.01); *A61P 35/02* (2018.01); *C07D 405/14* (2013.01); *C07D 491/056* (2013.01); *C07D 498/04* (2013.01); *A61K 2300/00* (2013.01)

(58) Field of Classification Search
CPC .................................................. C07D 239/94
USPC ......................................................... 544/101
See application file for complete search history.

(56) References Cited

FOREIGN PATENT DOCUMENTS

| CN | 1534026 A | 10/2004 |
|---|---|---|
| CN | 101003515 A | 7/2007 |
| CN | 102875570 A | 1/2013 |
| CN | 103965211 A | 8/2014 |
| CN | 104530063 A | 4/2015 |
| WO | WO9749688 A1 | 12/1997 |
| WO | WO02088129 A1 | 11/2002 |
| WO | WO03082830 A1 | 10/2003 |

OTHER PUBLICATIONS

Dinf,Martini M, Molinari F, et al. Wild-type Braf is required for response to panitumumab or cetuximab in metastatic colorectal cancer, Journal of Clinical Oncology, 2008, 26(35): 5705-5712.
Zhang Ke, et al, Resear ch on Development of Micromolecular Tyrosine Kinase Inhibitors in Treatment of Non-small Ce, clinical research progress: China, 2006, 33 (2):115-118.
Ciardiello F, Tortora G, EGFR antagonists in cancer treatment, New England Journal of Medicine, 2008,358 (11):1160-1174.
Ciardiello F, Caputo R, Bianco R, et al. Inhibition of growth factor production and angiogenesis in human cancer cells by ZD1839 (Iressa), a selective epidermal growth factor receptor tyrosine kinase inhibitor. Clinical Cancer Research, 2001, 7:1459-1465.
Barker A J, Gibson K H, Grundy W, et al. Studies Leading to the Identification of ZD1839 (Iressa): An Orally Active, Selective Epidermal Growth Factor Receptor Tyrosine Kinase Inhibitor Targeted to the Treatment of Cancer. Bioorganic & Chemistry Letters. 2001, 11:1911-1914.
Tsao, M S, Erlotinib in lung Cancer—Molecular and clinical predictors of outcome, New England Journal of Medicine, 2005, 353:133-144.
Wong M, K, et al. Erlotinib as maintenance treatment after failure to first-line gefitinib in non-smail cell lung cancer. Cancer Chemother Pharmacol, 2010, 65 (6):1023-1028.
Wood, E R, Truesdale A T, McDonald O B, et al, A unique structure for epidermal growth factor receptor bound to GW572016 (Lapatinib): relationships among protein conformation, inhibitor off-rate, and receptor activity in tumor cells, Cancer Research 2004, 64:6652-6659.
Geyer C, Forster J, Lindquist D, et al, Lapatinib plus capecitabine for HER2 positive advanced breast cancer, New England Journal of Medicine, 2006, 355 (26):2733-2743.
Shao J H, Guo J X, Zhang X D, et al. Synthesis and biological evaluation of crown ether fused quinazoiine analogues as potent EGFR inhibitors, Bioorganic & Medicinal Chemistry Letters, 2012, 12:6301-6305.
Qi Li, et al. EGFR gene mutation status among lung cancer patients in China, Chin J Oncol, Apr. 2007, vol. 29, No. 4, p. 270-273.

(Continued)

*Primary Examiner* — Kahsay Habte
(74) *Attorney, Agent, or Firm* — Gokalp Bayramoglu

(57) ABSTRACT

The present invention relates to an N-substituted-phenyl-5-substituted-alkoxy-2,3-dihydro-[1,4]dioxane[2,3-f]quinazolin-10-amine (I) or 4-substituted-arylamino-6-substituted-alkyl-6H-[1,4]oxazino[3,2-g]quinazoline-7(8H)-one (II) type compounds, a preparation method thereof and an application thereof as an inhibitor for epidermal growth factor receptor (EGFR) (comprising some mutant forms of EGFR) to treat cancer. These compounds and salts thereof can be used to treat or prevent various cancer diseases.

10 Claims, No Drawings

(56) References Cited

OTHER PUBLICATIONS

Kobayashi S, Boggon T J, Dayaram T, et al. EGFR mutation and resistance of non-small cell lung cancer to gefitinib, New England Journal of Medicine, 2005, 352(8): 786-792.

Engelman J A, Zejnullahu K, Mitsudomi T, et al. MET amplification leads to gefitinib resistance in lung cancer by activating ERBB3 Signaling, Science, 2007, 316(5827):1039-1043.

QUINAZOLINE HETEROCYCLIC COMPOUND AS EGFR KINASE INHIBITOR AND PREPARATION AND APPLICATION THEREOF

CROSS REFERENCE TO RELATED APPLICATIONS

This application is the national phase entry of International Application No. PCT/CN2016/070736, filed on Jan. 12, 2016, which is based upon and claims priority to Chinese Patent Application No. 201510015411.2, filed on Jan. 13, 2015, the entire contents of which are incorporated herein by reference.

TECHNICAL FIELD OF THE INVENTION

The present invention relates to N-substituted-phenyl-5-substituted-alkoxy-2,3-dihydro-[1,4]dioxane[2,3-f]quinazolin-10-amine compounds or 4-substituted-arylamino-6-substituted-alkyl-6H-[1,4]oxazino[3,2-g]quinazoline-7(8H)-one compounds, their method of preparation and their application thereof. Specifically, it relates to compounds of N-substituted-phenyl-5-substituted-alkoxy-2,3-dihydro-[1,4]dioxane[2,3-f]quinazolin-10-amine compounds or 4-substituted-arylamino-6-substituted-alkyl-6H-[1,4]oxazino[3,2-g]quinazoline-7(8H)-one with different substitutions, their method of preparation, and their application for cancer treatment as epidermal growth factor receptor inhibitors.

BACKGROUND OF THE INVENTION

Cancer is a serious threat to human life and health. According to data released by the World Health Organization, the new cases of cancers worldwide reached 14.1 million in 2012; cancer related deaths reached 8.2 million people. In 2008, these numbers were 1.27 million and 0.76 million respectively. In recent years, with the increase of aging population and environmental pollution, the occurrence and mortality rate of cancer have accelerated, and cancer has become one of the main causes of human death. It is expected that the world's new cases of cancer will reach 19.3 million people by 2025. Therefore, the new method of prevention and treatment for cancer is in urgent need.

According to the statistics, the top three cancers with the high occurrence rate were lung cancer (13%), breast cancer (11.9%) and colon cancer (9.7%), the top three cancers with the highest death rate were lung cancer (19.4%), liver cancer (9.1%) and gastric cancer (8.8%). Lung cancer has become the number one killer in cancer related death, in which non-small cell lung cancer (NSCLC) is the most common and accounts for 80% of the total number of lung cancers. Because of its lack of obvious early symptoms, most patients with lung cancer have developed into the middle or late stage when diagnosed, and thus missed the opportunity for early treatment Currently, the treatment for cancer mainly includes surgical treatment, radiotherapy and chemotherapy. The benefits with surgical treatment were obvious, but the recurrence and metastasis of tumor could happen easily. Radiation therapy can change the structure of the biological molecules. Thus, it can destroy the cancer cells. This method also has a strong side effect on normal cells. Chemotherapy uses chemical drugs to kill tumor cells, but it can also damage normal cells, causing obvious side effects.

In recent years, the tumor cell biology and genetics have been developed rapidly. The research on cancer gene, cell apoptosis and tumor angiogenesis has evolved to the level of molecular biology, the mechanism of tumor cells from molecular biology is being understood gradually, and the new ideas and methods of treatment are proposed continuously. Molecular targeted therapy provides a new way of cancer treatment. The study shows that the occurrence and development of tumor involve many signal transduction processes in living organisms. The molecular targeted drug is directed to malignant tumor tissues and cells based on specific biological targets. It has less toxic side effects and higher efficiency than the traditional chemotherapy does. As a result, cancer molecular targeted medicines have become the hot spot in the field of cancer research.

The molecular targeted therapy is a kind of therapy in which, on the basis of the molecular biology, the specific structure of the tumor tissue or cells is used as a target, and corresponding therapeutic medicines are designed to be able to combine with target molecules to achieve direct therapy or guiding therapy. This new method of cancer treatment is to reverse the malignant biological behavior of tumor cells at a molecular level so as to achieve the goal of inhibiting tumor growth. Unlike the conventional cytotoxic drugs, molecular targeted drugs can selectively kill the cancer cells by specifically acting on some specific sites (which normally are not expressed or less expressed in normal cells) so as to provide high safety, good tolerability, less toxic and side effect. For this reason, the molecular targeted therapy has a very big advantage and a broad application prospect.

As a targeted method of treatment, molecular targeted therapy needs to identify the biological targets in the first place. Currently, the common biological targets include oncogenes, anti-oncogenes and growth factor and its receptor, tumor angiogenesis factor, protein kinase and its signal transduction pathway, telomere and telomerase, DNA topoisomerase, histone deacetylase etc. There are multiple methods for testing the activity of the biological targets, including immunohistochemistry (IHC) to detect the protein expression, fluorescence in situ hybridization (FISH) or chromogenic in situ hybridization (CISH) to detect the number of gene copies, and polymerase chain reaction (PCR) to detect gene mutation. In many detection technologies, immunohistochemistry is the simplest, cheapest, and most commonly used.

Receptor tyrosine kinase (RTK) is the largest class of enzyme-linked receptors. It is both a receptor and an enzyme, which is capable of being bound by its ligand, allowing the phosphorylation of the target protein. All the RTKs are composed of three parts: the extracellular domain of the ligand binding site, the single transmembrane hydrophobic alpha helical region, and the intracellular domain involving receptor tyrosine kinase activity. At present, there are more than 50 RTKs, including epidermal growth factor receptor, platelet growth factor receptor, fibroblast growth factor receptor and vascular endothelial growth factor receptor In the absence of binding ligand, RTKs exist in the form of monomer without any bioactivity. Once a ligand binds to the extracellular domain of the receptor, the two receptor monomers form a receptor dimer by the process of polymerization, which leads to the activation of the receptors and the phosphorylation of the tyrosine residues. The phosphorylation transforms the intracellular domain of the receptor into a signal complex which activates a series of biochemical reactions in the cells involving cell proliferation and survival or combines different signals to create a comprehensive cell response (such as cell proliferation). Thus, RTKs play a key role in cell signal transduction.

Research found that over-expression or over-activation of the receptor tyrosine kinase has been observed in many cancer cells, for example, the over-expression of epidermal growth factor receptor in epithelial tumor cells, the over-expression of platelet growth factor receptor in glioma. Over-expression of the tyrosine receptor activates the downstream signal transduction pathway, leading to the abnormal transformation and proliferation of the cells, and promotes the development of tumor.

Epidermal growth factor receptor (EGFR) is a class of receptor tyrosine kinase, which is the expression product of proto-oncogene c-erbB1 and belongs to the HER/ErbB family. The receptor family includes four members, i.e., HER1 (EGFR/erbB-1), HER2 (neu/erbB-2), HER3 (erbB-3) and HER4 (erbB-4). EGFR is widely distributed in the surface of mammalian epithelial cells, fibroblasts, glial cells, and other cells. The signal pathway plays an important role in regulating the physiological processes of cells.

From structure perspective, EGFR is a transmembrane protein, made of 1186 amino acids. It is divided into extracellular domain (ECD), transmembrane domain (TM), and intracellular domain (D). The intracellular structure contains one tyrosine kinase domain and multiple auto phosphorylation sites. After phosphorylation, these tyrosine residues bind specifically to the downstream protein of the signal transduction pathway, thereby activating the EGFR signaling pathway and completing the conduction and transfer process of the signaling from the extracellular cell to the intracellular cell. There are 6 known EGFR ligands, including epidermal growth factor (EGF), transforming growth factor α(TGFα), AmpHiregulin, Bctacelluin (BTC), Heparin-binding EGF (HBEGF), Epiregulin (EPR), and EGF and TGFα are the two most important ligands of EGFR. The binding of a ligand with a receptor results in an important conformational change, causing the dimerization of the receptors, which leads to the phosphorylation and stimulation of numerous intracellular signal transduction pathways involved in cell proliferation, apoptosis, migration, and survival.

Research shows that EGFR expresses in all the normal epidermal cells, but about ⅓ of human tumor has abnormal expression of EGFR, including head and neck squamous cell carcinoma (HNSCC), malignant glioma, non-small cell lung cancer (NSCLC), breast cancer, colon cancer. The possible mechanism is that the high expression of EGFR increases the downstream signal transduction; mutant EGFR receptor or ligand expression leads to the increase of sustained activation of EGFR; abnormal signal transduction pathway activation, etc.

Upon the external activation, EGFR forms a receptor dimer by the process of polymerization. The binding of ATP into EGFR receptor leads to the phosphorylation of intracellular tyrosine residues, which further activates the 3 main signal transduction pathways: (1) Ras2/Raf2/MAPK pathway, this pathway activation can catalyze the nuclear transcription factor of many serine/threonine phosphorylation, promote gene transcription, cell division and cell cycle; (2) the PI3K/Akt/mTOR pathway, which is an important anti-apoptotic pathway, and is associated with angiogenesis; (3) the JAK/STAT pathway whose activation can promote cell proliferation and prolong cell survival. These in turn trigger signaling pathway and control gene transcription, cell proliferation, differentiation and survival, ultimately mediated cell differentiation, survival, migration, invasion, adhesion and cell damage and repair process. Therefore, blocking the EGFR signaling pathway can inhibit the growth of tumor cells. As result, EGFR is an important target for cancer targeted therapy.

EGFR is overexpressed in many tumor cells, which leads to the uncontrolled growth of tumor cells and the increased degree of malignancy. At present, a series of anticancer drugs targeting EGFR have been developed, and some of them have been used in clinics. There are two types of drugs targeting EGFR: (1) monoclonal antibody binding to the extracellular domain of EGFR, such as cetuximab (Cetuximab, Erbitux, MCC225), Matuzumab (EMD72000) and ABX-EGF; (2) small molecule inhibitors binding to the intracellular kinase domain of tyrosine (tyrosine kinase inhibitor, TK1), such as gefitinib, erlotinib (Gefitinib/Iressa/ZD1839) and AG-1478 (Erlotinib/Tarceva/OSI-774).

The EGFR monoclonal antibody (cetuximab and panitumumab) is a human-mouse chimeric IgG monoclonal antibody aiming at EGFR extracellular domain. This EGFR monoclonal antibody has a strong affinity for EGFR. It has the function of blocking the binding site of the growth factor, preventing ligand-induced receptor from activation and phosphorylation, inhibiting tyrosine kinase from activation, blocking the signal transduction pathway relating to tumor cell proliferation, inhibiting cells from proliferation and promoting apoptosis. (DINF, MARTINI M, MOLINARI F, et al. Wild-type Braf is required for response to panitumumab or cetuximab in metastatic colorectal cancer, Journal of Clinical Oncology, 2008, 26(35): 5705-5712)

The small molecule tyrosine kinase inhibitor EGFR-TKI can competitively bind to the ATP binding site of EGFR and inhibit the phosphorylation of the receptor, thereby blocking the conduction of the downstream signal. The aniline quinazoline compounds show good inhibitory effect of the EGFR and the best selectivity for a class of tyrosine kinase inhibitors (Zhang Ke, Xie Guangru, Pan Zhanyu, small molecule tyrosine kinase inhibitors in the treatment of non-small cell lung cancer, clinical research progress, China, 2006, 33 (2):115-118; CIARDIELLO F, TORTORA G, EGFR antagonists in cancer treatment, New England Journal of Medicine, 2008, 358 (11): 1160-1174). Currently, some of the small molecule EGFR inhibitors on the market are based on the structure of aniline quinazoline.

(1) Gefitinib (Gefitinib/Iressa/ZD1839). Gefitinib, also known as gefitinib or Iressa, was developed by AstraZeneca as a selective and reversible EGFR tyrosine kinase inhibitors. It was approved in May 2003 by the US FDA for the treatment of advanced non-small cell lung cancer after chemotherapy failure. It was approved in China in March 2005. Gefitinib could competitive binding to the epidermal growth factor receptor tyrosine kinase (EGFR-TK) binding sites of catalytic region, blocking its downstream signaling, growth, metastasis and vascular and block tumor growth, apoptosis and induce tumor cells to anti-tumor effect (1, CIARDIELLO F, CAPUTO R, BIANCO R, et al. Inhibition of growth factor production and angiogenesis in human cancer cells by ZD1839 (Iressa), a selective epidermal growth factor receptor tyrosine kinase inhibitor. Clinical Cancer Research, 2001, 7:1459-1465; 2, BARKER A J, GIBSON K H, GRUNDY W, et al. Studies Leading to the Identification of ZD1839 (Iressa): An Orally Active, Selective Epidermal Growth Factor Receptor Tyrosine Kinase Inhibitor Targeted to the Treatment of Cancer. Bioorganic & Chemistry Letters. 2001, 11:1911-1914).

Gefitinib is not only effective in the treatment of advanced non-small cell lung cancer, improving the symptoms relating to the disease, but also inhibit other solid tumors, including prostate cancer, breast cancer, head and neck cancer, gastric cancer, colon cancer. It can also improve the anti-tumor activity of chemotherapy, radiotherapy and hormone therapy.

(2) Erlotinib (Erlotinib/Tarceva/OSI-774). Erlotinib or Tarceva was approved in September 2002 by the FDA as the standard regimen for non-small cell lung cancer (NSCLC). Through inhibition of EGFR phosphorylation, the drug inhibits the downstream signal transduction and cell proliferation. In the in vivo tumor xenograft model of NSCLC and head and neck squamous cell carcinoma, erlotinib demonstrates anticancer effect by inhibiting tumor cell growth or inducing apoptosis of tumor cells. The experiment showed that erlotinib oral bioavailability is 80%. (1 TSAO, M S, Erlotinib in lung Cancer-Molecular and clinical predictors of outcome, New England Journal of Medicine, 2005, 353: 133-144; 2 WONG M, K, LO A I, LAM B, et al. Erlotinib as maintenance treatment after failure to first-line gefitinib in non-small cell lung cancer. Cancer Chemother Pharmacol, 2010, 65 (6): 1023-1028).

(3) Lapatinib (Lapatinib/Tykerb/GW572016). Lapatinib is EGFR/HER2 quinazoline inhibitors with dual target, developed by GlaxoSmithKline, which was approved in the United States in March 2007. Lapatinib can suppress both the EGFR and HER2 tyrosine kinase and its downstream MARK and PI3K signal transduction, thereby blocking the proliferation of cancer cells. Lapatinib is used for the treatment of non-small cell lung cancer and breast cancer (1, WOOD, E R, TRUESDALE A T, MCDONALD O B, et al, A unique structure for epidermal growth factor receptor bound to GW572016 (Lapatinib): relationships among protein conformation, inhibitor off-rate, and receptor activity in tumor cells, Cancer Research 2004, 64:6652-659; 2, GEYER C, FORSTER J, LINDQUIST D, et al, Lapatinib plus capecitabine for HER2 positive advanced breast cancer, New England Journal of Medicine, 2006, 355 (26):2733-2743).

(4) Icotinib (Icotinib, Conmana). Icotinib was approved in June 2011 by CFDA, this is China's first small molecules anti-tumor drug with independent intellectual property rights for the treatment of advanced non-small cell lung cancer. Icotinib retained core structure of quinazoline, the only difference is in the side chain with closed loop. The biological testing at molecular level showed that icotinib $IC_{50}$ was 5 nmol/mL, which show strong inhibitory effect against EGFR activity. From the screening of 85 kinases, icotinib selectively inhibits EGFR and 3 other mutants. It had no significant effect on the remaining 81 kinase. Icotinib showed good safety and tolerability profile (SHAO J H, GUO J X, ZHANG X D, et al. Synthesis and biological evaluation of crown ether fused quinazoline analogues as potent EGFR inhibitors, Bioorganic & Medicinal Chemistry Letters, 2012, 12:6301-6305).

EGFR inhibitors have achieved a certain effect on the treatment to advanced non-small cell lung cancer, but the resistance phenomenon has appeared in these drugs (Qi Li, Yali Zhao, Xianghong Li, Study on EGFR Gene Mutation in non-small Cell Lung Cancer, Chinese Journal of Oncology, 2007, 29 (4): 270). Because EGFR signaling pathways are involved in a variety of functions of the mediate cells, their drug resistance may be associated with the disorder of multiple signal conducting pathways, including drug resistance mutations, structural activation, and bypass activation of downstream signal. Common resistance mechanisms are as follows: 1) T790M mutation. The study found that EGFR mutations are found in many patients with EGFR-TKI resistance. T790M mutation (the tyrosine kinase active site 790 threonine mutates to methionine) was first proposed by Kobayashi in 2005 (KOBAYASHI S, BOGGON T J, DAYARAM T, et al. EGFR mutation and resistance of non-small cell lung cancer to gefitinib, New England Journal of Medicine, 2005, 352(8): 786-792) and is the most common secondary mutation. EGFR T790M mutations are found in approximately 50% of the drug-resistant patients. Through the EGFR gene detection of tumor tissue, it is found that No. 20 exon of EGFR had a secondary mutation, leading to tyrosine kinase 790 threonine is replaced by methionine, resulting in the emergence of drug resistance. The resistance caused by the T790M mutation is confirmed in subsequent studies. This may be due to the fact that the mutations increase the affinity of the active site of EGFR with the ATP and the binding of TKIs to EGFR is hindered. (ENGELMAN J A, ZEJNULLAHU K, MITSUDOMI T, et al. MET amplification leads to gefitinib resistance in lung cancer by activating ERBB3 Signaling, Science, 2007, 316 (5827): 1039-1043) 2) C-MET amplification. C-MET is a proto-oncogene whose coded protein is a receptor for hepatocyte growth factor (HGF) with tyrosine kinase activity. Engelman et al. proposed that C-MET amplification is another major mechanism for EGFR-TKIs-acquired drug resistant mutations, which accounts for 20% of all drug resistance. The amplification of C-MET activates the ErbB3/PI3K/AKT signaling pathway, leading to resistance of NSCLC patients to EGFR-TKIs.

It has been found that EGFR and its family receptor are overexpressed in tumor cells of incident cancer such as lung cancer. The mechanism of molecular biology indicates that abnormal expression of EGFR and its signal transduction have an important effect on the proliferation of tumor cells. Some EGFR-targeted small molecule inhibitors have been developed and used in the treatment of advanced non-small cell lung cancer. However, due to occurrence of the drug resistance mutations, the survival time of most advanced patients still needs to be improved.

SUMMARY OF THE INVENTION 4-amino quinazoline compounds are capable of inhibiting the over-expression of EGFR and its family members, The present invention relates to certain N-substituted-phenyl-5-substituted-alkoxy-2,3-dihydro-[1,4]dioxane[2,3-f]quinazolin-10-amine compounds or 4-substituted-arylamino-6-substituted-alkyl-6H-[1,4]oxazino[3,2-g]quinazoline-7(8H)-one compounds and pharmaceutically acceptable salts thereof which may be useful in the treatment or prevention of a disease or medical condition mediated through EGFR, including certain mutated forms of EGFR (for example, the L858R activating mutant, the Exonl 9 deletion activating mutant and the T790M resistance mutant). Such compounds and salts thereof may be useful in the treatment or prevention of a number of different cancers. The invention also relates to pharmaceutical compositions comprising said compounds and salts thereof, especially useful polymorphic forms of these compounds and salts, intermediates useful in the manufacture of said compounds and to methods of treatment of diseases mediated by various different forms of EGFR using said compounds and salts thereof.

In the first aspect of the invention there is provided compounds of Formula (I) and (II):

A compound of structure formula (I) or (II), N-substituted phenyl-5-substituted alkoxyl-2,3-dihydro-[1,4]dioxane[2,3-f]quinazolin-10-amine or 4-(substituted aryl)amino-6-substituted alkyl-6H-[1,4]oxazino[3,2-g]quinazolin-7(8H)-one:

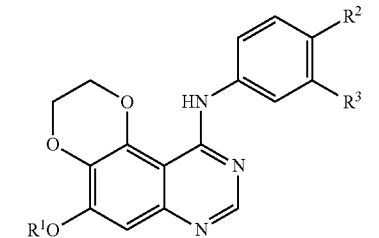

(I)

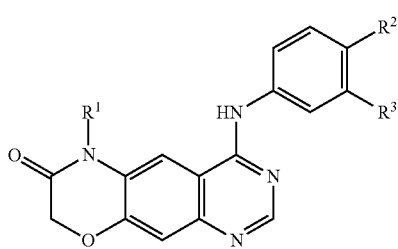

(II)

Where R¹ is:
1) —H;
2) $C^1$-$C^5$ alkyl or $C^1$-$C^5$ branched alkyl;
3) Tetrahydrofuranyl alkoxy, tetrahydropyranyl alkoxy, dioxanyl alkoxy, morpholinyl alkoxyl, $C^1$-$C^5$ alkyl or $C^1$-$C^5$ branched alkyl;
4) Alkoxy substituted $C^1$-$C^5$ alkyl or branched alkyl;
5) Nitrogen-containing saturated heterocycle or nitrogen-containing saturated heterocycle substituted $C^1$-$C^5$ alkyl or branched alkyl;

R² is:
1) —H;
2) Fluoride, chloride, bromide;
3) Fluoride benzyloxy, chloride benzyloxy, bromide benzyloxy, substituted benzyloxy, cyano benzyloxy, nitro benzyloxy, pyridylmethyl, $C^1$-$C^3$ alkyl substituted pyridylmethyl, fluoride pyridylmethyl, chloride pyridylmethyl;
4) Methyl, ethyl, propyl, isopropyl;
5) Methoxyl, ethoxyl, propoxy, isopropoxy.

R³ is:
1) —H;
2) Fluoride, chloride, bromide;
3) Ethenyl, propenyl, 1-butenyl, 2-butenyl, ethynyl, propynyl, 1-butynyl, 2-butynyl;
4) Nitro;
5) Cyano;
6) Methoxyl, ethoxyl, propoxy, isopropoxy.

It should be understood that the compounds of Formula (I) or (II), and pharmaceutically acceptable salts thereof, may exist in solvated forms and unsolvated forms. For example, a solvated form may be a hydrated form. It is to be understood that the present invention encompasses all such solvated and unsolvated forms.

One aspect of the invention is a pharmaceutical composition which comprises the compounds of the Formula (I) or (II). Such compositions can be administered to a subject in need thereof to inhibit the growth, development and/or metastasis of cancers, including solid tumors (e.g., lung, breast, colon, pancreatic, and head and neck cancers, among others), including those resistant to treatment with IRESSA and TARCEVA or another kinase inhibitor.

The cancer treatment method of this invention involves administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer such as lung cancer and breast cancer, in the recipient. Such administration constitutes a method for the treatment or prevention of diseases mediated by one or more kinases inhibited by one of the disclosed compounds or a pharmaceutically acceptable derivative thereof. "Administration" of a compound of this invention encompasses the delivery to a recipient of a compound of the sort described herein, or a prodrug or other pharmaceutically acceptable derivative thereof, using any suitable formulation or route of administration, as discussed herein. Typically, the compound is administered orally or intravenously one or more times per month, often one or more times per week, e.g. daily, every other day, 5 days/week, etc.

The phrase, "pharmaceutically acceptable derivative", as used herein, denotes any pharmaceutically acceptable salt, ester, or salt of such ester, of such compound, or any other adduct or derivative which, upon administration to a patient, is capable of providing a compound (directly or indirectly).

The compounds of this invention or their metabolites or residues otherwise will be described herein. Pharmaceutically acceptable derivatives include pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

Particularly favored derivatives and pro-drugs of a parent compound are those derivatives and pro-drugs that increase the bioavailability of the compound when administered to a mammal (e.g., by permitting enhanced absorption into the blood following oral administration) or which enhance delivery to a biological compartment of interest relative to the parent compound. Preferred prodrugs include derivatives of a compound with enhanced aqueous solubility or active transport through the gut membrane, relative to the parent compound.

Another important aspect of this invention is a method for treating cancer in a subject in need thereof, which comprises administering to the subject a treatment effective amount of a composition containing a compound of this invention. Various cancers which may be thus treated are noted elsewhere herein and include cancers which are or have become resistant to another anticancer agent such as Iressa, Tarceva, Tykerb/Tyverb or one of the other agents noted herein. Treatment may be provided in combination with one or more other cancer therapies, include surgery, radiotherapy, endocrine therapy, biologic response modifiers, hyperthermia, cryotherapy, agents to attenuate any adverse effects, and other cancer chemotherapeutic drugs. The other agents may be administered using a formulation, route of administration and dosing schedule the same or different from the ones used with the compound of this invention.

The other drugs include but not limited to one or more of the following: an anti-cancer alkylating or intercalating agent; antimetabolite; purine antagonist or pyrimidine antagonist; spindle poison; podophyllotoxin; antibiotic; nitrosourea; inorganic ion; enzyme; hormone; Temsirolimus, Everolimus; proteasome inhibitor; other kinase inhibitors such as EGFR kinase (e.g., Iressa, Tarceva, etc.), ErbB2 kinase (e.g., Tykerb/Tyverb), etc; an antibody, soluble receptor or other receptor antagonist against a receptor or hormone implicated in a cancer (including receptors such as EGFR, ErbB2, VEGFR, PDGFR; and agents such as Herceptin, Avastin, Erbitux, etc.); etc.

This invention also comprises the use of a compound of the invention, or a pharmaceutically acceptable derivative thereof, in the manufacture of a medicament for the treatment either acutely or chronically of cancer (including solid tumors, primary or metastatic, including cancers which are resistant or refractory to one or more other therapies). The compounds of this invention are useful in the manufacture of an anti-cancer medicament.

This invention further encompasses a composition comprising a compound of the invention, including a compound of any of the described classes or subclasses, including those of any of the formulas noted above, among others, preferably in a therapeutically-effective amount, in association with a least one pharmaceutically acceptable carrier, adjuvant or diluent.

Compounds of this invention are also useful as standards and reagents for characterizing various kinases, especially but not limited to ErbB family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

In any of the aspects or embodiments mentioned herein, the said cancers include but not limited to: ovarian cancer, cervical cancer, colorectal cancer, breast cancer, pancreatic cancer, glioma, glioblastoma, melanoma, prostate cancer, leukemia, lymphoma, non-Hodgkins lymphoma, gastric cancer, lung cancer, hepatocellular cancer, gastric cancer, gastrointestinal stromal tumor (GIST), thyroid cancer, bile duct cancer, endometrial cancer, renal cancer, anaplastic large cell lymphoma, acute myeloid leukemia (AML), multiple myeloma, melanoma and mesothelioma.

Synthesis of the Compounds of the Invention:

Refer Figure 1 for the Synthesis route for compounds of formula (I).

Figure 1: Synthesis route for compounds of formula (I)

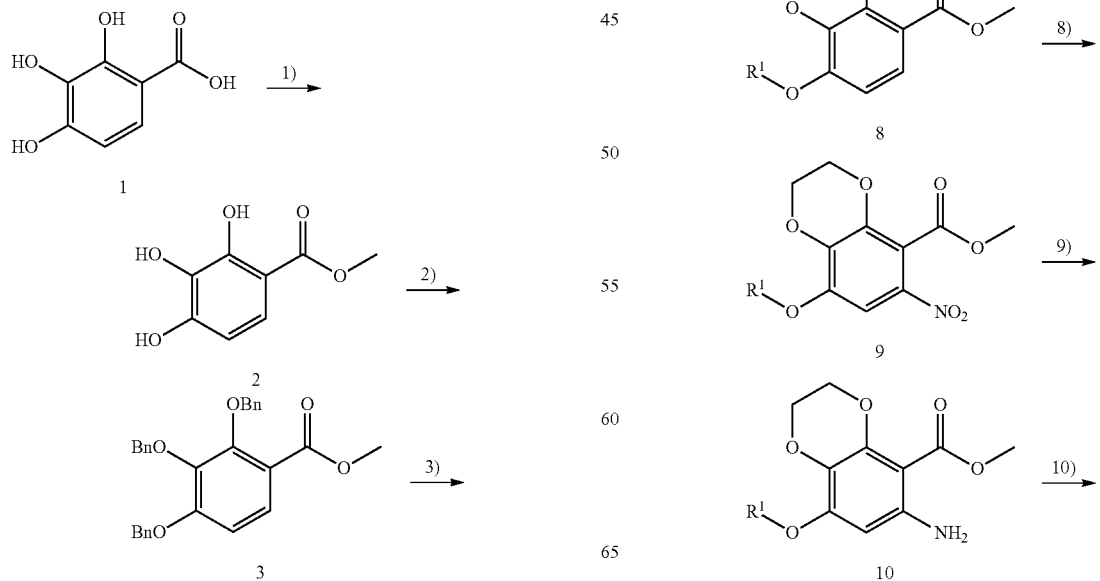

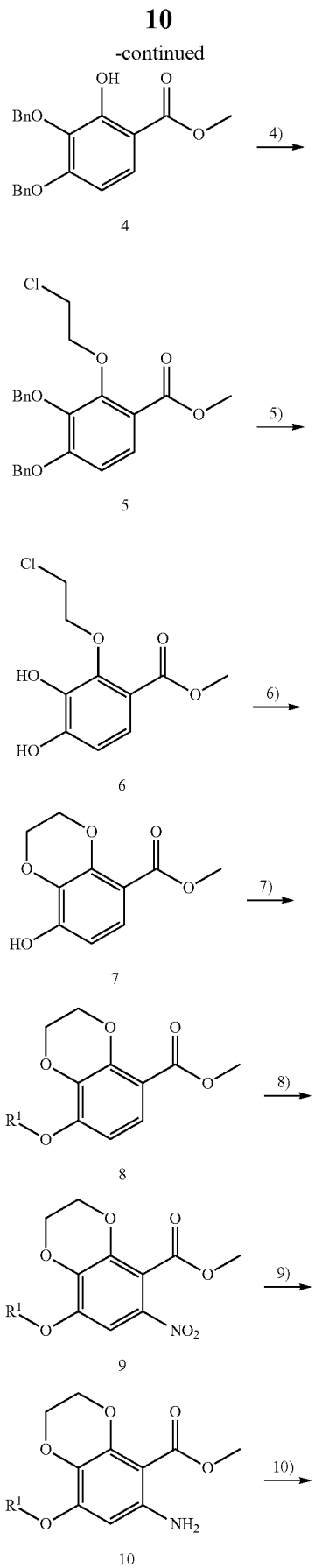

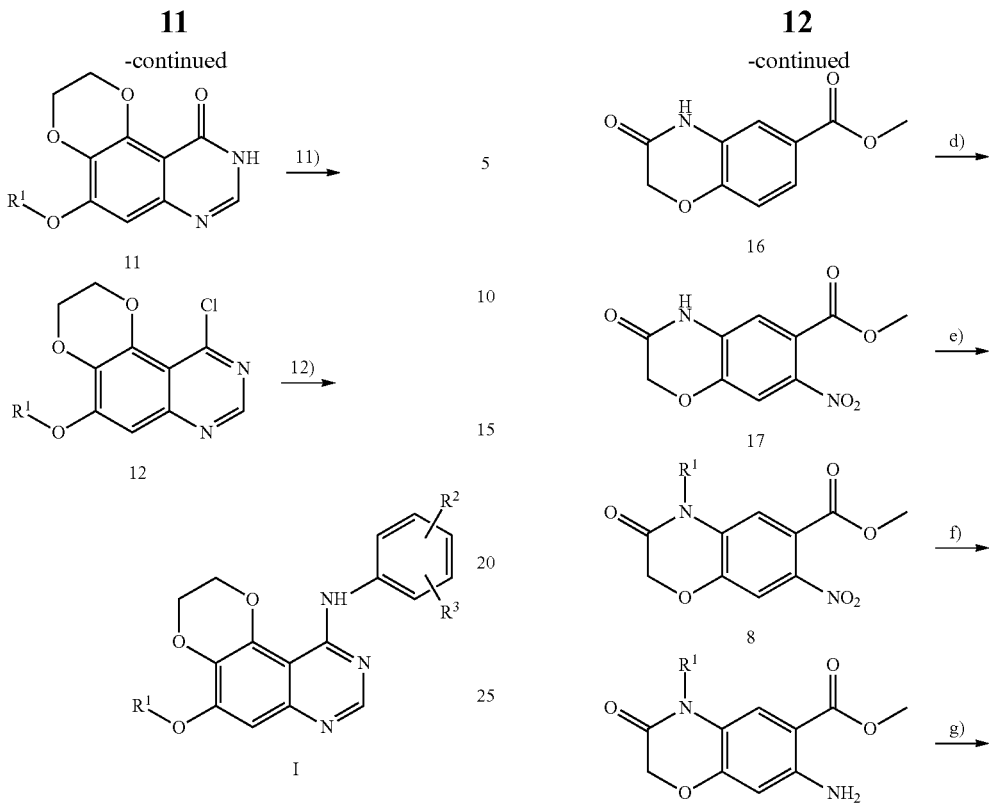

Reaction conditions: 1) KI, KHCO$_3$, DMF, 25° C.; 2) BnBr, K$_2$CO$_3$, DMF, 25° C.; 3) AcOH, HCl, 40° C.; 4) BrC$_2$H$_4$Cl, K$_2$CO$_3$, CH$_3$CN, 80° C.; 5) H$_2$, Pd/C, 25° C.; 6) K$_2$CO$_3$, DMF, 50° C.; 7) R—Br or R-OTs, K$_2$CO$_3$, CH$_3$CN, 80° C.; 8) HNO$_3$, HCl, 0° C.; 9) Zn, AcOH, 40° C.; 10) HCONH$_2$, 150° C.; 11) POCl$_3$, 120° C.; 12) aromatic amine, 1-butanol, 80° C.

Refer Figure 2 for the Synthesis route for compounds of formula (II).

Figure 2: Synthesis route for compounds of formula (II)

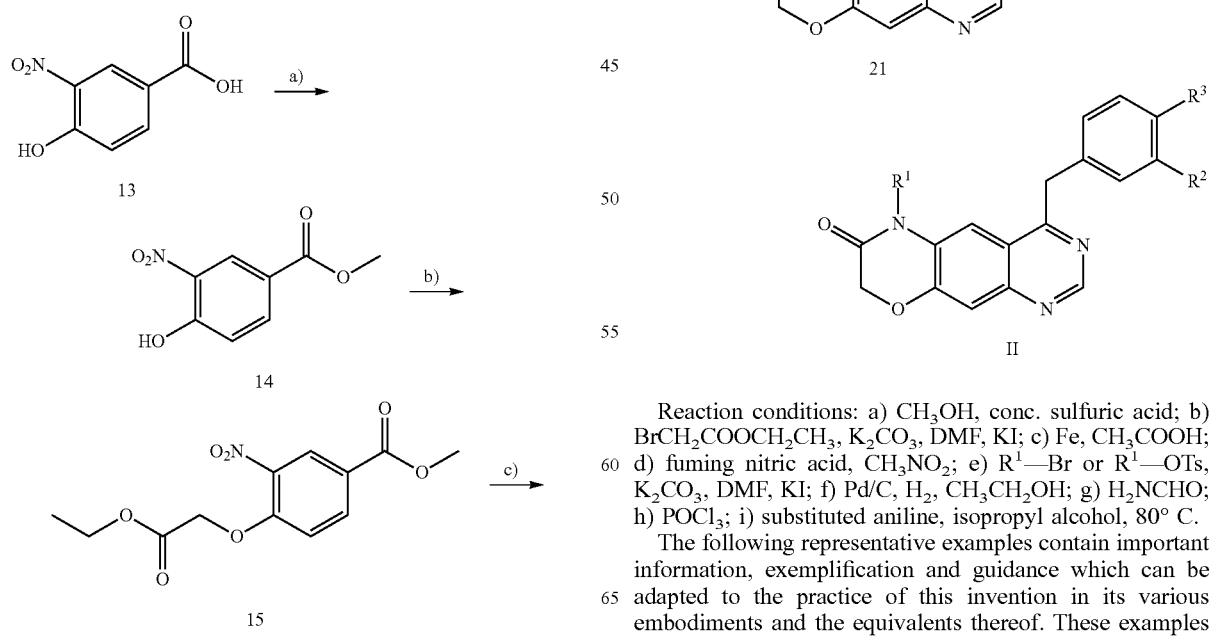

Reaction conditions: a) CH$_3$OH, conc. sulfuric acid; b) BrCH$_2$COOCH$_2$CH$_3$, K$_2$CO$_3$, DMF, KI; c) Fe, CH$_3$COOH; d) fuming nitric acid, CH$_3$NO$_2$; e) R$^1$—Br or R$^1$—OTs, K$_2$CO$_3$, DMF, KI; f) Pd/C, H$_2$, CH$_3$CH$_2$OH; g) H$_2$NCHO; h) POCl$_3$; i) substituted aniline, isopropyl alcohol, 80° C.

The following representative examples contain important information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art.

DETAILED DESCRIPTION OF THE INVENTION

Example 1

5-Isopropoxy-N-(4-methoxy-3-nitrophenyl)-2,3-dihydro-[1,4]dioxino[2,3-f]quinazolin-10-amine (I-1)

Step 1: Preparation for methyl 2,3,4-trihydroxybenzoate

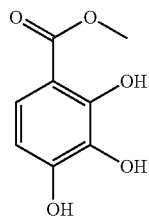

To a solution of 2,3,4-trihydroxybenzoic acid (34.0 g, 200 mmol) and potassium bicarbonate (40.0 g, 400 mmol) in dimethylformamide (300 mL) was added methyl iodide (42.0 g, 300 mmol). The mixture was stirred at ambient temperature for 12 hours, then quenched with water and filtered to obtain a white solid (35.0 g, yield=95%). MS: 185 (M+H$^+$).

Step 2: Preparation for methyl 2,3,4-tris(benzyloxy)benzoate

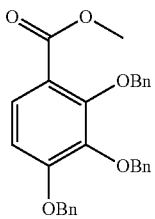 [SMILES: COC(=O)c1ccc(OCc2ccccc2)c(OCc2ccccc2)c1OCc1ccccc1]

To a solution of methyl 2,3,4-trihydroxybenzoate (18.5 g, 100 mmol) and potassium carbonate (42.0 g, 300 mmol) in dimethylformamide (150 mL) was added (bromomethyl)benzene (51.5 g, 300 mmol). The mixture was stirred at ambient temperature for 20 hours, then quenched with water and filtered to obtain a light yellow solid (30.2 g, yield=66%); MS: 455 (M+H$^+$).

Step 3: Preparation for methyl 3,4-bis(benzyloxy)-2-hydroxybenzoate

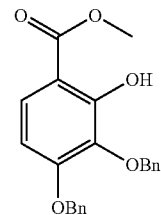 [SMILES: COC(=O)c1ccc(OCc2ccccc2)c(OCc2ccccc2)c1O]

To a solution of hydrochloric acid (37%, 10 mL) and acetic acid (100 mL) was added methyl 2,3,4-tris(benzyloxy)benzoate (18.2 g, 40 mmol) at 40° C. The mixture was stirred at 40° C. for 2 hours, then quenched with ice water and filtered to obtain a yellow solid (8.0 g, yield=55%); MS: 365 (M+H$^+$).

Step 4: Preparation for methyl 3,4-bis(benzyloxy)-2-(2-chloroethoxy)benzoate

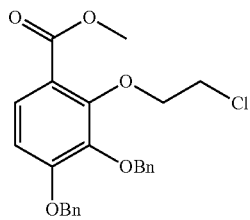 [SMILES: COC(=O)c1ccc(OCc2ccccc2)c(OCc2ccccc2)c1OCCCl]

To a solution of methyl 3,4-bis(benzyloxy)-2-hydroxybenzoate (7.2 g, 20 mmol) and potassium carbonate (4.2 g, 30 mmol) in dimethylformamide (50 mL) was added 1-bromo-2-chloroethane (4.3 g, 30 mmol). The mixture was added stirred at 80° C. for 5 hours. After cooling to ambient temperature, the solution was quenched with ice water, extracted with ethyl acetate and washed with saturated brine. The obtained organic layer was dried over magnesium sulfate, filtered and concentrated to obtain a crude product as a yellow oil which was used in next step without further purification (8.2 g, yield=95%); MS: 427 (M+H$^+$).

Step 5: Preparation for methyl 2-(2-chloroethoxy)-3,4-dihydroxybenzoate

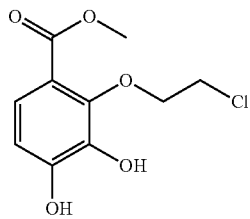 [SMILES: COC(=O)c1ccc(O)c(O)c1OCCCl]

To a solution of Pd/C (0.5 g) in methanol (50 mL) was added methyl 3,4-bis(benzyloxy)-2-(2-chloroethoxy)benzoate (8.2 g, 19.2 mmol). The solution was degassed with hydrogen twice and then stirred at ambient temperature for 8 hours. After that the solution was filtered and concentrated to obtain a white solid (3.8 g, yield=80%); MS: 247 (M+H$^+$).

Step 6: Preparation for methyl 8-hydroxy-2,3-dihydrobenzo[b][1,4]dioxine-5-carboxylate

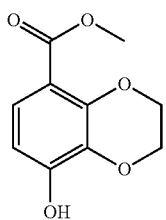

To a solution of methyl 2-(2-chloroethoxy)-3,4-dihydroxybenzoate (2.5 g, 10 mmol) in dimethylformamide (20 mL) was added potassium carbonate (1.4 g, 10 mmol). The mixture was stirred at 60° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (2.1 g, yield=95%); $^1$H NMR (DMSO-d$_6$, 300 MHz): δ 9.97 (s, 1H), 7.22-7.17 (m, 1H), 6.44-6.40 (m, 1H), 4.27-4.24 (m, 4H), 3.71 (s, 3H); MS: 211 (M+H$^+$).

Step 7: Preparation for methyl 8-isopropoxy-2,3-dihydrobenzo[b][1,4]dioxine-5-carboxylate

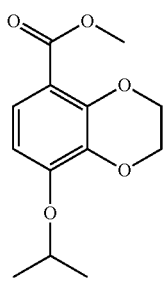

To a solution of methyl 8-hydroxy-2,3-dihydrobenzo[b][1,4]dioxine-5-carboxylate (1.0 g, 5 mmol) and potassium carbonate (1.4 g, 10 mmol) in dimethylformamide (10 mL) was added 2-bromopropane (1.2 g, 10 mmol). The mixture was stirred at 80° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (1.2 g, yield=95%); MS: 253 (M+H$^+$).

Step 8: Preparation for methyl 8-isopropoxy-6-nitro-2,3-dihydrobenzo[b][1,4]dioxine-5-carboxylate

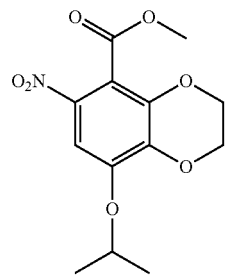 [SMILES: COC(=O)c1c([N+](=O)[O-])cc(OC(C)C)c2c1OCCO2]

To a solution of methyl 8-isopropoxy-2,3-dihydrobenzo[b][1,4]dioxine-5-carboxylate (1.0 g, 4 mmol) in acetic acid (9 mL) was added a solution of acetic acid (3 mL) and nitric acid fuming (98%, 6 mL) in dropwise at 0° C. with stirring. The mixture was stirred at 0° C. for 2 hours, then quenched with ice water and filtered to obtain a yellow solid (1.2 g, yield=95%); $^1$NMR (CDCl$_3$, 300 MHz): δ 7.40 (s, 1H), 4.69 (quint, J=4.5 Hz, 1H), 4.44-4.42 (m, 2H), 4.38-4.32 (m, 2H), 3.97 (s, 3H), 1.46 (d, J=4.5 Hz, 6H).

Step 9: Preparation for methyl 6-amino-8-isopropoxy-2,3-dihydrobenzo[b][1,4]dioxine-5-carboxylate

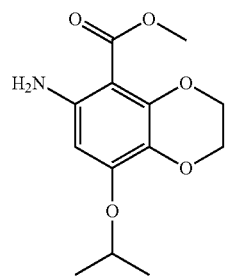

To a solution of methyl 8-isopropoxy-6-nitro-2,3-dihydrobenzo[b][1,4]dioxine-5-carboxylate (1.2 g, 4 mmol) in acetic acid (10 mL) was added zinc powder. The mixture was stirred at 40° C. for 2 hours, then filtered and concentrated to obtain a brown solid which was purified by column chromatography on silicon gel (dichloromethane:methanol=100:1) to obtain a yellow solid (1.0 g, yield=95%); MS: 268 (M+H$^+$).

Step 10: Preparation for 5-Isopropoxy-2,3-dihydro-[1,4]dioxino[2,3-f]quinazolin-10-ol

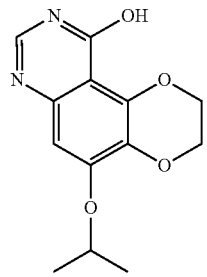 [SMILES: CC(C)Oc1cc2ncnc(O)c2c2c1OCCO2]

A solution of methyl 6-amino-8-isopropoxy-2,3-dihydrobenzo[b][1,4]dioxine-5-carboxylate (1.0 g, 3.8 mmol) in formamide (10 mL) was stirred at 150° C. for 24 hours. After cooling to ambient temperature, the solution was concentrated in vacuum to obtain a brown solid (1.0 g, yield=95%); MS: 263 (M+H$^+$).

Step 11: Preparation for 10-Chloro-5-isopropoxy-2,3-dihydro-[1,4]dioxino[2,3-f]quinazoline

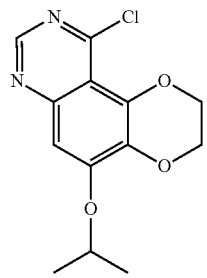 [SMILES: CC(C)Oc1cc2ncnc(Cl)c2c2c1OCCO2]

A solution of 5-isopropoxy-2,3-dihydro-[1,4]dioxino[2,3-f]quinazolin-10-ol (1.0 g, 3.8 mmol) in phosphorus oxychloride (15 mL) was stirred at 110° C. for 24 hours. After cooling to ambient temperature, the solution was quenched with a large amount of ice, then adjusted the pH to 9 with K$_2$CO$_3$, extracted with ethyl acetate and washed with saturated brine. The obtained organic layer was dried over magnesium sulfate, filtered and concentrated to obtain a crude product as a yellow solid which was purified by column chromatography on silicon gel (dichloromethane:methanol=100:1) to obtain a yellow solid (0.6 g, yield=55%); MS: 281 (M+H$^+$).

Step 12: Preparation for 5-Isopropoxy-N-(4-methoxy-3-nitrophenyl)-2,3-dihydro-[1,4]dioxino[2,3-f]quinazolin-10-amine

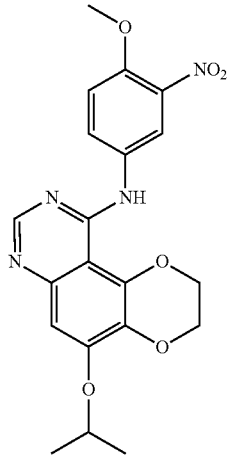 [SMILES: COc1ccc(Nc2ncnc3cc(OC(C)C)c4c(c23)OCCO4)cc1[N+](=O)[O-]]

To a solution of 10-chloro-5-isopropoxy-2,3-dihydro-[1,4]dioxino[2,3-f]quinazoline (0.1 g, 0.36 mmol) in isopropanol (3 mL) was added 4-methoxy-3-nitroaniline (0.060 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.08 g, yield=50%). $^1$NMR (DMSO-d$_6$, 400 MHz): δ 11.02 (s, 1H), 8.94 (d, 1H, J=8.8 Hz), 8.64 (s, 1H), 8.03 (d, 1H, J=8.8 Hz), 7.92 (s, 1H), 7.12 (s, 1H), 4.83 (dd, 1H, J=6 Hz), 4.71 (s, 2H), 4.51 (s, 2H), 4.14 (s, 3H), 1.40 (d, 6H, J=6 Hz); MS: 413 (M+H)$^+$.

Example 2

N-(4-Fluoro-3-nitrophenyl)-5-isopropoxy-2,3-dihydro-[1,4]dioxino[2,3-f]quinazolin-10-amine (I-2)

Step 1 to 11 is the same as in example 1;

Step 12: N-(4-Fluoro-3-nitrophenyl)-5-isopropoxy-2,3-dihydro-[1,4]dioxino[2,3-f]quinazolin-10-amine

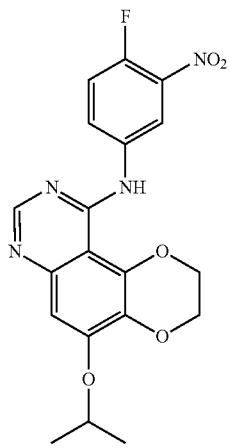 [SMILES: CC(C)Oc1cc2ncnc(Nc3ccc(F)c([N+](=O)[O-])c3)c2c2c1OCCO2]

To a solution of 10-chloro-5-isopropoxy-2,3-dihydro-[1,4]dioxino[2,3-f]quinazoline (0.1 g, 0.36 mmol) in isopropanol (3 mL) was added 4-fluoro-3-nitroaniline (0.062 g, 0.40 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.12 g, yield=75%). $^1$H NMR (DMSO-$d_6$, 400 MHz): δ 10.59 (s, 1H), 8.77 (s, 1 Hz), 8.53-8.51 (m, 1H), 8.09-8.07 (m, 1H), 7.75-7.72 (m, 1H), 7.18 (s, 1H), 4.80 (dd, 1H, J=4.8 Hz), 4.61 (s, 2H), 4.53 (s, 2H), 1.40 (d, 6H, J=4.8 Hz); MS: 401 (M+H)$^+$.

Example 3

5-Isopropoxy-N-(4-methyl-3-nitrophenyl)-2,3-dihydro-[1,4]dioxino[2,3-f]quinazolin-10-amine (I-3)

Step 1 to 11 is the same as in example 1;

Step 12: Preparation for 5-Isopropoxy-N-(4-methyl-3-nitrophenyl)-2,3-dihydro-[1,4]dioxino[2,3-f]quinazolin-10-amine

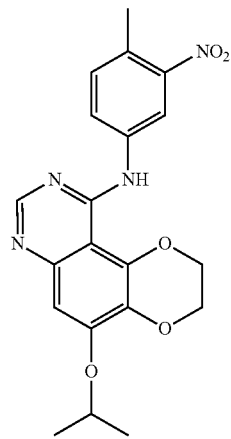 [SMILES: Cc1ccc(Nc2ncnc3cc(OC(C)C)c4c(c23)OCCO4)cc1[N+](=O)[O-]]

To a solution of 10-chloro-5-isopropoxy-2,3-dihydro-[1,4]dioxino[2,3-f]quinazoline (0.1 g, 0.36 mmol) in isopropanol (3 mL) was added 4-methyl-3-nitroaniline (0.060 g, 0.40 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.10 g, yield=62%). $^1$H NMR (DMSO-$d_6$, 400 MHz): δ 10.55 (s, 1H), 8.76 (s, 1 Hz), 8.39 (s, 1H), 7.98 (d, 1H, J=8 Hz), 7.60 (d, 1H, J=8 Hz), 7.15 (s, 1H), 4.81 (dd, 1H, J=6 Hz), 4.62 (s, 2H), 4.45 (s, 2H), 1.40 (d, 6H, J=6 Hz); MS: 397 (M+H)$^+$.

Example 4

N-(4-Chloro-3-nitrophenyl)-5-isopropoxy-2,3-dihydro-[1,4]dioxino[2,3-f]quinazolin-10-amine (I-4)

Step 1 to 11 is the same as in example 1;

Step 12: Preparation for N-(4-Chloro-3-nitrophenyl)-5-isopropoxy-2,3-dihydro-[1,4]dioxino[2,3-f]quinazolin-10-amine

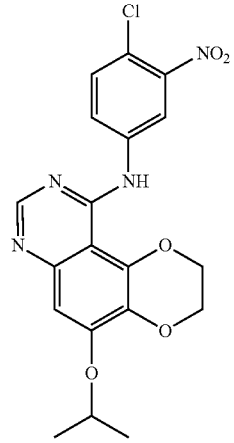 [SMILES: CC(C)Oc1cc2ncnc(Nc3ccc(Cl)c([N+](=O)[O-])c3)c2c2c1OCCO2]

To a solution of 10-chloro-5-isopropoxy-2,3-dihydro-[1,4]dioxino[2,3-f]quinazoline (0.1 g, 0.36 mmol) in isopropanol (3 mL) was added 4-chloro-3-nitroaniline (0.070 g, 0.40 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.11 g, yield=67%). $^1$H NMR (DMSO-$d_6$, 400 MHz): δ 10.57 (s, 1H), 8.79 (s, 1 Hz), 8.51 (s, 1H), 8.05 (d, 1H, J=8.4 Hz), 7.88 (d, 1H, J=8.8 Hz), 7.15 (s, 1H), 4.81 (dd, 1H, J=6 Hz), 4.61 (s, 2H), 4.45 (s, 2H), 1.40 (d, 6H, J=6 Hz); MS: 417 (M+H)$^+$.

Example 5

2-Fluoro-5-((5-isopropoxy-2,3-dihydro-[1,4]dioxino[2,3-f]quinazolin-10-yl)amino)benzonitrile (I-5)

Step 1 to 11 is the same as in example 1;

Step 12: Preparation for 2-Fluoro-5-((5-isopropoxy-2,3-dihydro-[1,4]dioxino[2,3-f]quinazolin-10-yl)amino)benzonitrile

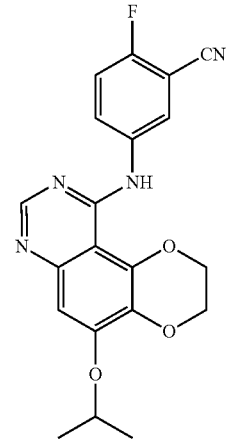 [SMILES: CC(C)Oc1cc2ncnc(Nc3ccc(F)c(C#N)c3)c2c2c1OCCO2]

To a solution of 10-chloro-5-isopropoxy-2,3-dihydro-[1,4]dioxino[2,3-f]quinazoline (0.05 g, 0.18 mmol) in isopropanol (3 mL) was added 4-chloro-3-nitroaniline (0.030 g, 0.20 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.045 g, yield=55%). $^1$H NMR (DMSO-$d_6$, 400 MHz): δ 10.54 (s, 1H), 8.76 (s, 1 Hz), 8.24-8.23 (m, 1H), 8.04 (t, 1H, J=8.8 Hz), 7.66 (t, 1H, J=8.8 Hz), 7.21 (s, 1H), 4.79 (dd, 1H, J=6 Hz), 4.60 (s, 2H), 4.45 (s, 2H), 1.40 (d, 6H, J=6 Hz); MS: 381 (M+H)$^+$.

Example 6

5-((5-Isopropoxy-2,3-dihydro-[1,4]dioxino[2,3-f]quinazolin-10-yl)amino)-2-methylbenzonitrile (I-6)

Step 1 to 11 is the same as in example 1;

Step 12: Preparation for 5-((5-Isopropoxy-2,3-dihydro-[1,4]dioxino[2,3-f]quinazolin-10-yl)amino)-2-methylbenzonitrile

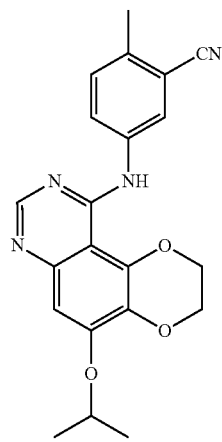 [SMILES: Cc1ccc(Nc2ncnc3cc(OC(C)C)c4c(c23)OCCO4)cc1C#N]

To a solution of 10-chloro-5-isopropoxy-2,3-dihydro-[1,4]dioxino[2,3-f]quinazoline (0.05 g, 0.18 mmol) in isopropanol (3 mL) was added 5-amino-2-methylbenzonitrile (0.026 g, 0.20 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.050 g, yield=67%). $^1$H NMR (DMSO-$d_6$, 400 MHz): δ 10.50 (s, 1H), 8.75 (s, 1 Hz), 8.11 (s, 1H), 7.88 (d, 1H, J=8.4 Hz), 7.56 (d, 1H, J=8.4 Hz), 7.11 (s, 1H), 4.80 (dd, 1H, J=6 Hz), 4.61 (s, 2H), 4.45 (s, 2H), 1.40 (d, 6H, J=6 Hz); MS: 378 (M+H)$^+$.

Example 7

N-(3-Chloro-4-fluorophenyl)-5-isopropoxy-2,3-dihydro-[1,4]dioxino[2,3-f]quinazolin-10-amine (I-7)

Step 1 to 11 is the same as in example 1;

Step 12: Preparation for N-(3-Chloro-4-fluorophenyl)-5-isopropoxy-2,3-dihydro-[1,4]dioxino[2,3-f]quinazolin-10-amine

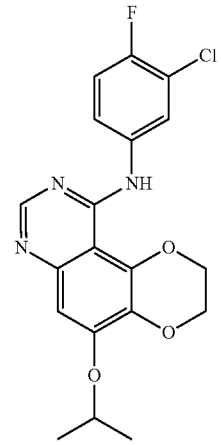 [SMILES: CC(C)Oc1cc2ncnc(Nc3ccc(F)c(Cl)c3)c2c2c1OCCO2]

To a solution of 10-chloro-5-isopropoxy-2,3-dihydro-[1,4]dioxino[2,3-f]quinazoline (0.05 g, 0.18 mmol) in isopropanol (3 mL) was added 3-chloro-4-fluoroaniline (0.029 g, 0.20 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.040 g, yield=50%). $^1$H NMR (DMSO-$d_6$, 400 MHz): δ 10.44 (s, 1H), 8.72 (s, 1 Hz), 7.97-7.95 (m, 1H), 7.68-7.65 (m, 1H), 7.56-7.51 (m, 1H), 7.02 (s, 1H), 4.81 (dd, 1H, J=6 Hz), 4.60 (s, 2H), 4.44 (s, 2H), 1.40 (d, 6H, J=6 Hz); MS: 390 (M+H)$^+$.

Example 8

N-(3-Ethynylphenyl)-5-isopropoxy-2,3-dihydro-[1,4]dioxino[2,3-f]quinazolin-10-amine (I-8)

Step 1 to 11 is the same as in example 1;

Step 12: Preparation for N-(3-Ethynylphenyl)-5-isopropoxy-2,3-dihydro-[1,4]dioxino[2,3-f]quinazolin-10-amine

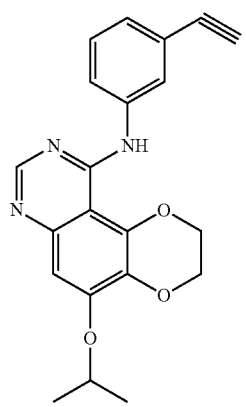 [SMILES: C#Cc1cccc(Nc2ncnc3cc(OC(C)C)c4c(c23)OCCO4)c1]

To a solution of 10-chloro-5-isopropoxy-2,3-dihydro-[1,4]dioxino[2,3-f]quinazoline (0.1 g, 0.36 mmol) in isopropanol (3 mL) was added 3-ethynylaniline (0.042 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=46%). $^1$H NMR (DMSO-d$_6$, 300 MHz): δ 10.35 (s, 1H), 8.69 (s, 1H), 7.85 (s, 1H), 7.73 (d, J=6 Hz, 1H), 7.47 (t, J=6 Hz, 1H), 7.38 (d, J=6 Hz, 1H), 7.11 (s, 1H), 4.81-4.78 (m, 1H), 4.61 (s, 2H), 4.44 (s, 2H). 4.27 (s, 1H), 1.39 (d, J=4.5 Hz, 6H); MS: 362 (M+H$^+$).

Example 9

N-(4-Methoxy-3-nitrophenyl)-5-(2-methoxyethoxy)-2,3-dihydro-[1,4]dioxino[2,3-f]quinazolin-10-amine (I-9)

Step 1 to 6 is the same as in example 1;

Step 7: Preparation for methyl 8-(2-methoxyethoxy)-2,3-dihydrobenzo[b][1,4]dioxine-5-carboxylate To a solution of methyl 8-hydroxy-2,3-dihydrobenzo[b][1,4]dioxine-5-carboxylate (4.0 g, 20 mmol) and potassium carbonate (2.8 g, 20 mmol) in dimethylformamide (10 mL) was added 1-bromo-2-methoxyethane (2.8 g, 20 mmol). The mixture was stirred at 80° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (5.1 g, yield=95%); MS: 269 (M+H$^+$).

Step 8: Preparation for methyl 8-(2-methoxyethoxy)-6-nitro-2,3-dihydrobenzo[b][1,4]dioxine-5-carboxylate To a solution of methyl 8-(2-methoxyethoxy)-2,3-dihydrobenzo[b][1,4]dioxine-5-carboxylate (5.0 g, 19 mmol) in acetic acid (45 mL) was added a solution of acetic acid (15 mL) and nitric acid fuming (98%, 30 mL) in dropwise at 0° C. with stirring. The mixture was stirred at 0° C. for 2 hours, then quenched with ice water and filtered to obtain a yellow solid (5.0 g, yield=95%).

Step 9: Preparation for methyl 6-amino-8-(2-methoxyethoxy)-2,3-dihydrobenzo[b][1,4]dioxine-5-carboxylate To a solution of methyl 8-(2-methoxyethoxy)-6-nitro-2,3-dihydrobenzo[b][1,4]dioxine-5-carboxylate (3.1 g, 10 mmol) in acetic acid (20 mL) was added zinc powder (2.6 g, 40 mmol). The mixture was stirred at 40° C. for 2 hours, then filtered and concentrated to obtain a brown solid which was purified by column chromatography on silicon gel (dichloromethane:methanol=100:1) to obtained a yellow solid (2.8 g, yield=95%); MS: 284 (M+H$^+$).

Step 10: Preparation for 5-(2-Methoxyethoxy)-2,3-dihydro-[1,4]dioxino[2,3-f]quinazolin-10-ol

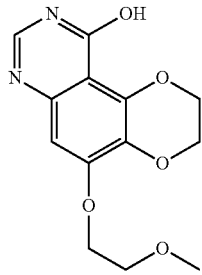 [SMILES: COCCOc1cc2ncnc(O)c2c2c1OCCO2]

A solution of 6-amino-8-(2-methoxyethoxy)-2,3-dihydrobenzo[b][1,4]dioxine-5-carboxylate (2.8 g, 10 mmol) in formamide (10 mL) was stirred at 150° C. for 24 hours. After cooling to ambient temperature, the solution was concentrated in vacuum to obtain a brown solid (2.6 g, yield=95%). MS: 279 (M+H⁺). ¹H NMR (CDCl₃, 400 MHz): δ 7.29 (s, 1H), 5.86 (s, 1H), 4.30 (s, 2H), 4.10 (s, 2H), 3.85 (s, 2H), 3.75 (s, 2H), 3.32 (s, 3H); MS: 279 (M+H)⁺.

Step 11: Preparation for 10-Chloro-5-(2-methoxyethoxy)-2,3-dihydro-[1,4]dioxino[2,3-f]quinazoline

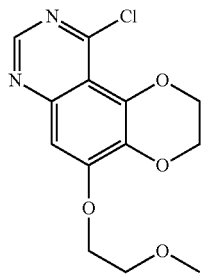 [SMILES: COCCOc1cc2ncnc(Cl)c2c2c1OCCO2]

A solution of 5-(2-methoxyethoxy)-2,3-dihydro-[1,4]dioxino[2,3-f]quinazolin-10-ol (2.0 g, 7.2 mmol) in phosphorus oxychloride (15 mL) was stirred at 110° C. for 24 hours. After cooling to ambient temperature, the solution was quenched with a large amount of ice, adjusted the pH to 9 with K₂CO₃, extracted with ethyl acetate and washed with saturated brine. The obtained organic layer was dried over magnesium sulfate, filtered and concentrated to obtain a crude product as a yellow solid which was purified by column chromatography on silicon gel (dichloromethane:methanol=100:1) to obtained a yellow solid (1.2 g, yield=60%); MS: 297 (M+H⁺).

Step 12: Preparation for N-(4-Methoxy-3-nitrophenyl)-5-(2-methoxyethoxy)-2,3-dihydro-[1,4]dioxino[2,3-f]quinazolin-10-amine

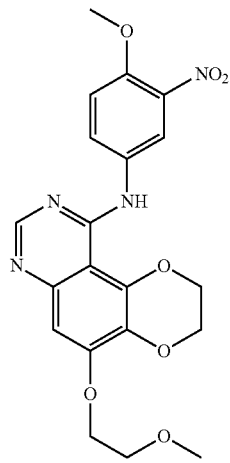 [SMILES: COCCOc1cc2ncnc(Nc3ccc(OC)c([N+](=O)[O-])c3)c2c2c1OCCO2]

To a solution of 10-chloro-5-(2-methoxyethoxy)-2,3-dihydro-[1,4]dioxino[2,3-f]quinazoline (0.1 g, 0.34 mmol) in isopropanol (3 mL) was added 4-methoxy-3-nitroaniline (0.060 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.1 g, yield=63%). ¹H NMR (DMSO-d₆, 400 MHz): δ 11.01 (s, 1H), 8.91-8.88 (m, 2H), 8.00 (d, 1H, J=8.8 Hz), 7.91 (s, 1H), 7.10 (s, 1H), 4.72 (s, 2H), 4.53 (s, 2H), 4.29 (t, 2H, J=4 Hz), 4.13 (s, 3H), 3.87 (s, 1H), 3.76 (t, 2H, J=4.4 Hz), 3.35 (s, 3H); MS: 429 (M+H)⁺.

Example 10

N-(4-Fluoro-3-nitrophenyl)-5-(2-methoxyethoxy)-2,3-dihydro-[1,4]dioxino[2,3-f]quinazolin-10-amine (I-10)

Step 1 to 6 is the same as in example 1;
Step 7 to 11 is the same as in example 9;

Step 12: Preparation for N-(4-Fluoro-3-nitrophenyl)-5-(2-methoxyethoxy)-2,3-dihydro-[1,4]dioxino[2,3-f]quinazolin-10-amine

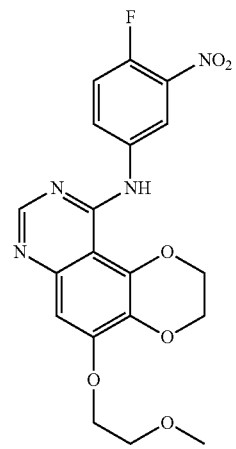 [SMILES: COCCOc1cc2ncnc(Nc3ccc(F)c([N+](=O)[O-])c3)c2c2c1OCCO2]

To a solution of 10-chloro-5-(2-methoxyethoxy)-2,3-dihydro-[1,4]dioxino[2,3-f]quinazoline (0.1 g, 0.34 mmol) in isopropanol (3 mL) was added 4-fluoro-3-nitroaniline (0.060 g, 0.38 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=40%). ¹H NMR (DMSO-d₆, 400 MHz): δ 10.58 (s, 1H), 8.76 (s, 1H), 8.54-8.52 (m, 1H), 8.09 (d, 1H, J=8.8 Hz), 7.75-7.70 (m, 1H), 7.14 (s, 1H), 4.62 (s, 2H), 4.47 (s, 2H), 4.30 (s, 2H), 3.70 (s, 2H), 3.35 (s, 3H); MS: 417 (M+H)⁺.

Example 11

5-(2-Methoxyethoxy)-N-(4-methyl-3-nitrophenyl)-2,3-dihydro-[1,4]dioxino[2,3-f]quinazolin-10-amine (I-11)

Step 1 to 6 is the same as in example 1;
Step 7 to 11 is the same as in example 9;

Step 12: Preparation for 5-(2-Methoxyethoxy)-N-(4-methyl-3-nitrophenyl)-2,3-dihydro-[1,4]dioxino[2,3-f]quinazolin-10-amine

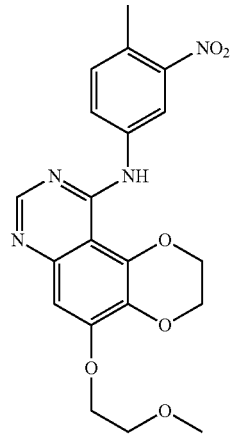 [SMILES: COCCOc1cc2ncnc(Nc3ccc(C)c([N+](=O)[O-])c3)c2c2c1OCCO2]

To a solution of 10-chloro-5-(2-methoxyethoxy)-2,3-dihydro-[1,4]dioxino[2,3-f]quinazoline (0.1 g, 0.34 mmol) in isopropanol (3 mL) was added 4-methyl-3-nitroaniline (0.06 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.08 g, yield=57%). $^1$H NMR (DMSO-$d_6$, 400 MHz): δ 10.59 (s, 1H), 8.79 (s, 1H), 8.51 (s, 1H), 8.50 (d, 1H, J=8.4 Hz), 7.88 (d, 1H, 8.4 Hz), 7.16 (s, 1H), 4.63 (s, 2H), 4.47 (s, 2H), 4.30 (s, 2H), 4.13 (s, 3H), 3.76 (s, 2H), 3.35 (s, 3H); MS: 413 (M+H)$^+$.

Example 12

N-(4-Chloro-3-nitrophenyl)-5-(2-methoxyethoxy)-2,3-dihydro-[1,4]dioxino[2,3-f]quinazolin-10-amine (I-12)

Step 1 to 6 is the same as in example 1;
Step 7 to 11 is the same as in example 9;

Step 12: Preparation for N-(4-Chloro-3-nitrophenyl)-5-(2-methoxyethoxy)-2,3-dihydro-[1,4]dioxino[2,3-f]quinazolin-10-amine

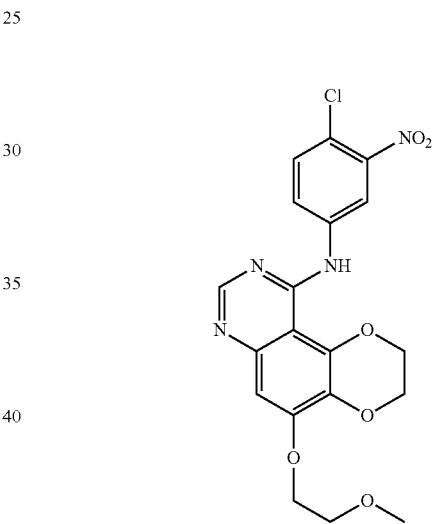

To a solution of 10-chloro-5-(2-methoxyethoxy)-2,3-dihydro-[1,4]dioxino[2,3-f]quinazoline (0.1 g, 0.34 mmol) in isopropanol (3 mL) was added 4-chloro-3-nitroaniline (0.06 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.07 g, yield=44%). $^1$H NMR (DMSO-$d_6$, 400 MHz): δ 10.57 (s, 1H), 8.79 (s, 1H), 8.53-8.52 (m, 1H), 8.07-8.06 (m, 1H), 8.04-8.03 (m, 1H), 7.89-7.87 (m, 1H), 4.62 (br, 2H), 4.47 (br, 2H), 4.32-4.30 (m, 2H), 3.77-3.75 (m, 2H), 3.34 (s, 1H); MS: 433 (M+H)$^+$.

Example 13

2-Fluoro-5-((5-(2-methoxyethoxy)-2,3-dihydro-[1,4]dioxino[2,3-f]quinazolin-10-yl)amino)benzonitrile (I-13)

Step 1 to 6 is the same as in example 1;
Step 7 to 11 is the same as in example 9;

Step 12: Preparation for 2-Fluoro-5-((5-(2-methoxyethoxy)-2,3-dihydro-[1,4]dioxino[2,3-f]quinazolin-10-yl)amino)benzonitrile

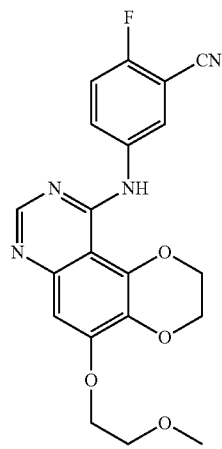 [SMILES: COCCOc1cc2ncnc(Nc3ccc(F)c(C#N)c3)c2c2c1OCCO2]

To a solution of 10-chloro-5-(2-methoxyethoxy)-2,3-dihydro-[1,4]dioxino[2,3-f]quinazoline (0.1 g, 0.34 mmol) in isopropanol (3 mL) was added 5-amino-2-fluoro benzonitrile (0.055 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtained a yellow solid (0.077 g, yield=53%). $^1$H NMR (DMSO-$d_6$, 400 MHz): δ 10.51 (s, 1H), 8.74 (s, 1H), 8.10 (s, 1H), 7.88 (d, 1H, J=8.4 Hz), 7.56 (d, 1H, J=8.4 Hz), 7.09 (s, 1H), 4.62 (s, 2H), 4.46 (s, 2H), 4.30 (s, 2H), 3.76 (s, 2H), 3.35 (s, 3H); MS: 397 (M+H)$^+$.

Example 14

5-((5-(2-Methoxyethoxy)-2,3-dihydro-[1,4]dioxino[2,3-f]quinazolin-10-yl)amino)-2-methylbenzonitrile (I-14)

Step 1 to 6 is the same as in example 1;
Step 7 to 11 is the same as in example 9

Step 12: Preparation for 5-((5-(2-Methoxyethoxy)-2,3-dihydro-[1,4]dioxino[2,3-f]quinazolin-10-yl)amino)-2-methylbenzonitrile

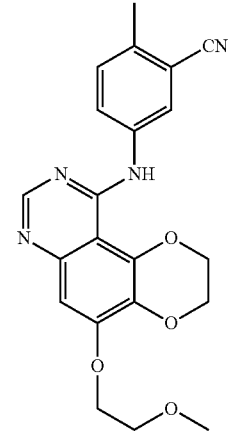 [SMILES: COCCOc1cc2ncnc(Nc3ccc(C)c(C#N)c3)c2c2c1OCCO2]

To a solution of 10-chloro-5-(2-methoxyethoxy)-2,3-dihydro-[1,4]dioxino[2,3-f]quinazoline (0.1 g, 0.34 mmol) in isopropanol (3 mL) was added 5-amino-2-methyl benzonitrile (0.053 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.07 g, yield=49%). $^1$H NMR (DMSO-$d_6$, 400 MHz): δ 10.47 (s, 1H), 8.73 (s, 1H), 8.26-8.24 (m, 1H), 8.08-8.05 (m, 1H), 7.66 (t, 1H, J=8.8 Hz), 7.03 (s, 1H), 4.61 (s, 2H), 4.47 (s, 2H), 4.31 (s, 2H), 3.76 (s, 2H), 3.35 (s, 3H), 2.50 (s, 3H); MS: 393 (M+H)$^+$.

Example 15

5-(1-Ethoxyethoxy)-N-(4-methoxy-3-nitrophenyl)-2,3-dihydro-[1,4]dioxino[2,3-f]quinazolin-10-amine (I-15)

Step 1 to 6 is the same as in example 1

Step 7: Preparation for methyl 8-(1-ethoxyethoxy)-2,3-dihydrobenzo[b][1,4]dioxine-5-carboxylate

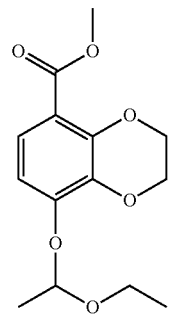 [SMILES: CCOC(C)Oc1ccc(C(=O)OC)c2c1OCCO2]

To a solution of methyl 8-hydroxy-2,3-dihydrobenzo[b][1,4]dioxine-5-carboxylate (2.1 g, 10 mmol), PPh₃ (4.6 g, 15 mmol), diethyl azodicarboxylate (2.6 g, 15 mmol) in THF (70 mL) was added 1-ethoxyethanol (1.0 g, 11 mmol) with stirring at room temperature for 20 hours. And then the resulting mixture was concentrated to obtain a yellow solid which was purified by column chromatography on silicon gel (PE:EA=5:1) to obtained a white solid (2.5 g, yield=89%).

Step 8: Preparation for methyl 8-(1-ethoxyethoxy)-6-nitro-2,3-dihydrobenzo[b][1,4]dioxine-5-carboxylate

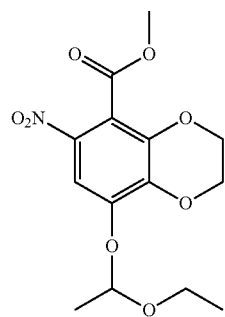 [SMILES: CCOC(C)Oc1cc([N+](=O)[O-])c(C(=O)OC)c2c1OCCO2]

To a solution of methyl methyl 8-(1-ethoxyethoxy)-2,3-dihydrobenzo[b][1,4]dioxine-5-carboxylate (2.5 g, 8.8 mmol) in acetic acid (24 mL) was added a solution of acetic acid (8 mL) and nitric acid filming (98%, 16 mL) in dropwise at 0° C. with stirring. The mixture was stirred at 0° C. for 2 hours, then quenched with ice water and filtered to obtain a yellow solid (2.6 g, yield=90%).

Step 9: Preparation for methyl 6-amino-8-(1-ethoxyethoxy)-2,3-dihydrobenzo[b][1,4]dioxine-5-carboxylate

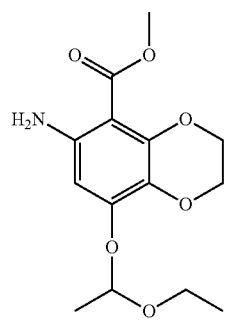

To a solution of methyl 8-(1-ethoxyethoxy)-6-nitro-2,3-dihydrobenzo[b][1,4]dioxine-5-carboxylate (2.6 g, 8 mmol) in acetic acid (20 mL) was added zinc powder (2.6 g, 40 mmol). The mixture was stirred at 40° C. for 2 hours, then filtered and concentrated to obtain a brown solid (2.3 g, yield=95%); MS: 298 (M+H)⁺.

Step 10: Preparation for 5-(1-Ethoxyethoxy)-2,3-dihydro-[1,4]dioxino[2,3-f]quinazolin-10-ol

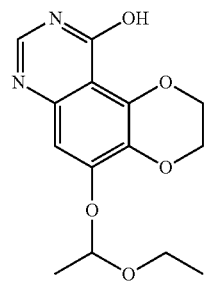

A solution of 6-amino-8-(1-ethoxyethoxy)-2,3-dihydrobenzo[b][1,4]dioxine-5-carboxylate (2.3 g, 7.7 mmol) in formamide (10 mL) was stirred at 150° C. for 24 hours. After cooling to ambient temperature, the solution was concentrated in vacuum to obtain a brown solid (2.2 g, yield=95%); MS: 293 (M+H⁺).

Step 11: Preparation for 10-Chloro-5-(1-ethoxyethoxy)-2,3-dihydro-[1,4]dioxino[2,3-f]quinazoline

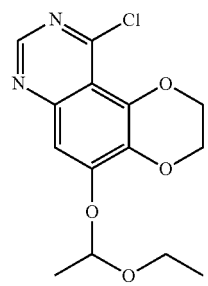

A solution of 5-(1-ethoxyethoxy)-2,3-dihydro-[1,4]dioxino[2,3-f]quinazolin-10-ol (2.0 g, 6.8 mmol) in phosphorus oxychloride (15 mL) was stirred at 110° C. for 24 hours. After cooling to ambient temperature, the solution was quenched with a large amount of ice, adjusted the pH to 9 with K₂CO₃, extracted with ethyl acetate and washed with saturated brine. The obtained organic layer was dried over magnesium sulfate, filtered and concentrated to obtain a crude product as a yellow solid (1.3 g, yield=61%); MS: 311 (M+H⁺).

Step 12: Preparation for 5-(1-Ethoxyethoxy)-N-(4-methoxy-3-nitrophenyl)-2,3-dihydro-[1,4]dioxino[2,3-f]quinazolin-10-amine

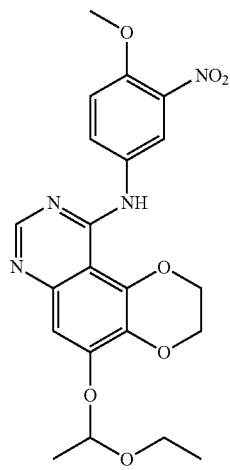 [SMILES: CCOC(C)Oc1cc2ncnc(Nc3ccc(OC)c([N+](=O)[O-])c3)c2c2c1OCCO2]

To a solution of 10-chloro-5-(1-ethoxyethoxy)-2,3-dihydro-[1,4]dioxino[2,3-f]quinazoline (0.1 g, 0.33 mmol) in isopropanol (3 mL) was added 4-methoxy-3-nitroaniline (0.060 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.11 g, yield=69%). $^1$H NMR (DMSO-d$_6$, 400 MHz): δ 11.06 (s, 1H), 8.91-8.87 (m, 2H), 8.02 (d, 1H, J=9.2 Hz), 7.91 (s, 1H), 7.21 (s, 1H), 4.83-4.82 (m, 1H), 4.71 (s, 2H), 4.52 (s, 2H), 4.13 (s, 3H), 3.63-3.56 (m, 2H), 3.32 (s, 3H), 1.33 (d, 3H, J=6 Hz); MS: 443 (M+H)$^+$.

Example 16

5-(1-Ethoxyethoxy)-N-(4-fluoro-3-nitrophenyl)-2,3-dihydro-[1,4]dioxino[2,3-f]quinazolin-10-amine
(I-16)

Step 1 to 6 is the same as in example 1;
Step 7 to 11 is the same as in example 15;

Step 12: Preparation for 5-(1-Ethoxyethoxy)-N-(4-fluoro-3-nitrophenyl)-2,3-dihydro-[1,4]dioxino[2,3-f]quinazolin-10-amine

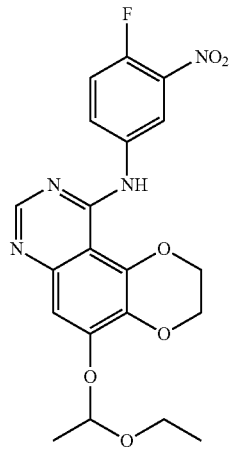 [SMILES: CCOC(C)Oc1cc2ncnc(Nc3ccc(F)c([N+](=O)[O-])c3)c2c2c1OCCO2]

To a solution of 10-chloro-5-(1-ethoxyethoxy)-2,3-dihydro-[1,4]dioxino[2,3-f]quinazoline (0.1 g, 0.33 mmol) in isopropanol (3 mL) was added 4-fluoro-3-nitroaniline (0.060 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtained a yellow solid (0.65 g, yield=44%). $^1$H NMR (DMSO-d$_6$, 400 MHz): δ 10.60 (s, 1H), 8.77 (s, 1H), 8.53-8.51 (m, 1H), 8.09-8.07 (m, 1H), 7.73 (d, 1H, J=10 Hz), 7.25 (s, 1H), 4.82 (q, 1H, J=6 Hz), 4.61 (s, 2H), 4.46 (s, 2H), 3.62-3.56 (m, 2H), 3.32 (s, 3H), 1.33 (d, 3H, J=6 Hz); MS: 431 (M+H)$^+$.

Example 17

N-(4-Chloro-3-nitrophenyl)-5-(1-ethoxyethoxy)-2,3-dihydro-[1,4]dioxino[2,3-f]quinazolin-10-amine
(I-17)

Step 1 to 6 is the same as in example 1;
Step 7 to 11 is the same as in example 15;

Step 12: N-(4-Chloro-3-nitrophenyl)-5-(1-ethoxyethoxy)-2,3-dihydro-[1,4]dioxino[2,3-f]quinazolin-10-amine

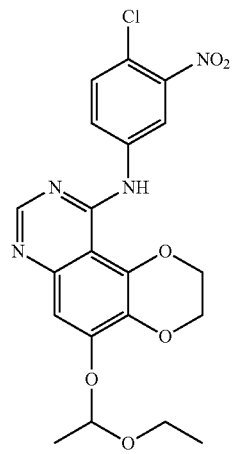 [SMILES: CCOC(C)Oc1cc2ncnc(Nc3ccc(Cl)c([N+](=O)[O-])c3)c2c2c1OCCO2]

To a solution of 10-chloro-5-(1-ethoxyethoxy)-2,3-dihydro-[1,4]dioxino[2,3-f]quinazoline (0.1 g, 0.33 mmol) in isopropanol (3 mL) was added 4-chloro-3-nitroaniline (0.060 g, 0.35 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.05 g, yield=32%). $^1$H NMR (DMSO-d$_6$, 400 MHz): δ 10.61 (s, 1H), 8.80 (s, 1H), 8.50 (s, 1H), 8.04 (d, 1H, J=8.8 Hz), 7.89 (d, 1H, J=8.8 Hz), 7.28 (s, 1H), 4.81 (q, 1H, J=6 Hz), 4.62 (s, 2H), 4.46 (s, 2H), 3.62-3.56 (m, 2H), 3.31 (s, 3H), 1.33 (d, 3H, J=6 Hz); MS: 447 (M+H)$^+$.

Example 18

5-(1-Ethoxyethoxy)-N-(4-methyl-3-nitrophenyl)-2,3-dihydro-[1,4]dioxino[2,3-f]quinazolin-10-amine (I-18)

Step 1 to 6 is the same as in example 1;
Step 7 to 11 is the same as in example 15;

Step 12: Preparation for 5-(1-Ethoxyethoxy)-N-(4-methyl-3-nitrophenyl)-2,3-dihydro-[1,4]dioxino[2,3-f]quinazolin-10-amine

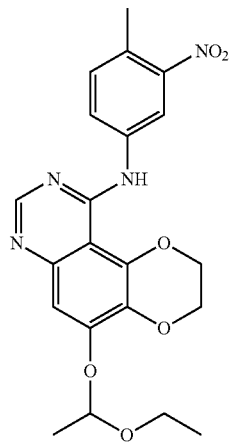 [SMILES: CCOC(C)Oc1cc2ncnc(Nc3ccc(C)c([N+](=O)[O-])c3)c2c2c1OCCO2]

To a solution of 10-chloro-5-(1-ethoxyethoxy)-2,3-dihydro-[1,4]dioxino[2,3-f]quinazoline (0.1 g, 0.33 mmol) in isopropanol (3 mL) was added 4-methyl-3-nitroaniline (0.060 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.085 g, yield=57%). $^1$H NMR (DMSO-$d_6$, 400 MHz): δ 10.66 (s, 1H), 8.79 (s, 1H), 8.35 (s, 1H), 7.91 (d, 1H, J=8.4 Hz), 7.61 (d, 1H, J=8.4 Hz), 7.21 (s, 1H), 4.83-4.82 (m, 1H), 4.64 (s, 2H), 4.47 (s, 2H), 3.62-3.60 (m, 2H), 3.31 (s, 3H), 2.52 (s, 3H), 1.33 (d, J=6 Hz); MS: 427 (M+H$^+$).

Example 19

5-((5-(1-Ethoxyethoxy)-2,3-dihydro-[1,4]dioxino[2,3-f]quinazolin-10-yl)amino)-2-fluoro-benzonitrile (I-19)

Step 1 to 6 is the same as in example 1;
Step 7 to 11 is the same as in example 15;

Step 12: Preparation for 5-((5-(1-Ethoxyethoxy)-2,3-dihydro-[1,4]dioxino[2,3-f]quinazolin-10-yl)amino)-2-fluoro-benzonitrile

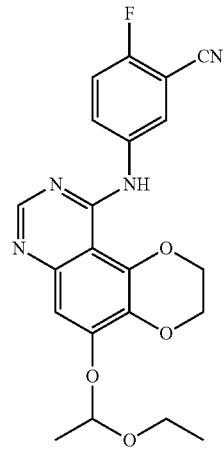 [SMILES: CCOC(C)Oc1cc2ncnc(Nc3ccc(F)c(C#N)c3)c2c2c1OCCO2]

To a solution of 10-chloro-5-(1-ethoxyethoxy)-2,3-dihydro-[1,4]dioxino[2,3-f]quinazoline (0.1 g, 0.33 mmol) in isopropanol (3 mL) was added 5-amino-2-fluorobenzonitrile (0.060 g, 0.44 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.062 g, yield=46%). $^1$H NMR (DMSO-$d_6$, 400 MHz): δ 10.59 (s, 1H), 8.77 (s, 1H), 8.23-82.1 (m, 1H), 8.05-8.01 (m, 1H), 7.67 (t, 1H, 9.2 Hz), 7.22 (s, 1H), 4.83-4.79 (m, 1H), 4.60 (s, 2H), 4.45 (s, 2H), 3.62-3.56 (m, 2H), 3.32 (s, 3H), 1.33 (d, 3H, J=6 Hz); MS: 411 (M+H)$^+$.

Example 20

5-((5-(1-Ethoxyethoxy)-2,3-dihydro-[1,4]dioxino[2,3-f]quinazolin-10-yl)amino)-2-methylbenzonitrile (I-20)

Step 1 to 6 is the same as in example 1;
Step 7 to 11 is the same as in example 15;

Step 12: Preparation for 5-((5-(1-Ethoxyethoxy)-2,3-dihydro-[1,4]dioxino[2,3-f]quinazolin-10-yl)amino)-2-methylbenzonitrile

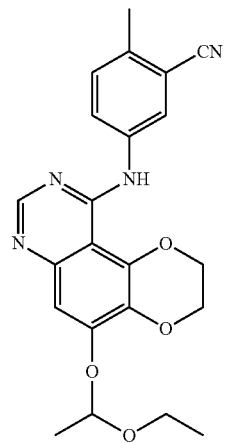 [SMILES: CCOC(C)Oc1cc2ncnc(Nc3ccc(C)c(C#N)c3)c2c2c1OCCO2]

To a solution of 10-chloro-5-(1-ethoxyethoxy)-2,3-dihydro-[1,4]dioxino[2,3-f]quinazoline (0.1 g, 0.33 mmol) in isopropanol (3 mL) was added 5-amino-2-methylbenzonitrile (0.053 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=40%). $^1$H NMR (DMSO-d$_6$, 400 MHz): δ 10.57 (s, 1H), 8.76 (s, 1H), 8.09 (m, 1H), 7.86 (d, 1H, J=8.4 Hz), 7.57 (d, 1H, J=8.4 Hz), 7.23 (s, 1H), 4.82-4.78 (m, 1H), 4.61 (s, 2H), 4.45 (s, 2H), 3.66-3.56 (m, 2H), 3.32-3.30 (m, 3H), 2.51 (s, 3H), 1.33 (d, 3H, J=6 Hz); MS: 407 (M+H)$^+$.

Example 21

N-(3-Ethynylphenyl)-5-(tetrahydro-2H-pyran-4-yloxy)-2,3-dihydro-[1,4]dioxino[2,3-f]quinazolin-10-amine (I-21)

Step 1 to 6 is the same as in example 1;
Step 7: Preparation for tetrahydro-2H-pyran-4-ol

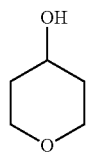

To a solution of lithium aluminium hydride (0.95 g, 25 mmol) in tetrahydrofuran (40 mL) was dihydro-2H-pyran-4(3H)-one (2.0 g, 20 mmol) with stirring at 0° C. The mixture was stirred at ambient temperature for 2 hours, quenched with sodium hydroxide (30%, 0.45 g), filtered, dried over magnesium sulfate, filtered and concentrated to obtain a crude product as a light-yellow oil (2.0 g, yield=95%).

Step 8: Preparation for tetrahydro-2H-pyran-4-yl 4-methylbenzenesulfonate

To a mixture of tetrahydro-2H-pyran-4-ol (0.5 g, 5 mmol) and 4-methylbenzene-1-sulfonyl chloride (1.4 g, 7.5 mmol) was added pyridine (5 mL). The solution was stirred at ambient temperature for 24 hours, washed with hydrochloric acid (1 mol/L), extracted with ethyl acetate and washed with saturated brine. The obtained organic layer was dried over magnesium sulfate, filtered and concentrated to obtain a crude product as a light-yellow oil (1.2 g, yield=95%).

Step 9: Preparation for methyl 8-(tetrahydro-2H-pyran-4-yloxy)-2,3-dihydrobenzo[b][1,4]dioxine-5-carboxylate

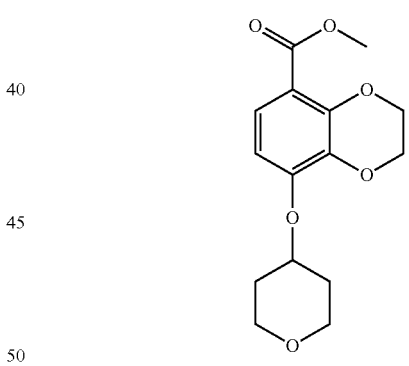

To a solution of methyl 8-hydroxy-2,3-dihydrobenzo[b][1,4]dioxine-5-carboxylate (1.0 g, 5 mmol) and potassium carbonate (1.4 g, 10 mmol) in acetonitrile (10 mL) was added tetrahydro-2H-pyran-4-yl 4-methylbenzenesulfonate (1.2 g, 5 mmol). The mixture was stirred at 80° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (1.2 g, yield=80%). MS: 295 (M+H$^+$). $^1$H NMR (CDCl$_3$, 400 MHz): δ 7.46 (d, 1H, J=9.2 Hz), 6.89 (d, 1H, J=9.2 Hz), 4.55 (dd, 1H, J=4 Hz), 4.40-4.33 (m, 4H), 4.06-4.01 (m, 2H), 3.88 (s, 3H), 3.60-3.54 (m, 2H), 2.08-2.04 (m, 2H), 1.89-1.85 (m, 2H); MS: 295 (M+H$^+$).

Step 10: Preparation for methyl 6-nitro-8-(tetrahydro-2H-pyran-4-yloxy)-2,3-dihydrobenzo[b][1,4]dioxine-5-carboxylate

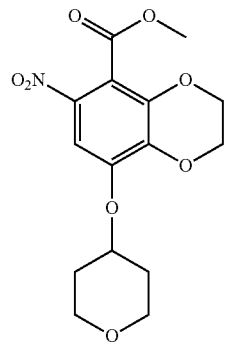 [SMILES: COC(=O)c1c([N+](=O)[O-])cc(OC2CCOCC2)c2c1OCCO2]

To a solution of methyl 8-(tetrahydro-2H-pyran-4-yloxy)-2,3-dihydrobenzo[b][1,4]dioxine-5-carboxylate (1.1 g, 4 mmol) in acetic acid (9 mL) at 0° C. was added a mixture of acetic acid (3 mL) and nitric acid (6 mL) dropwise. After that the mixture was stirred for 1 hour, poured into ice water (500 mL), stirred for another 1 hour, filtered and dried to obtain a yellow solid (1.2 g, 95% yield). $^1$H NMR (CDCl$_3$, 400 MHz): δ 7.41 (s, 1H), 4.60 (dd, 1H, J=4 Hz), 4.43-4.42 (m, 2H), 4.38-4.37 (m, 2H), 4.04-4.01 (m, 2H), 3.97 (s, 3H), 3.64-3.58 (m, 2H), 2.07-2.06 (m, 2H), 1.88-1.87 (m, 2H).

Step 11: Preparation for methyl 6-amino-8-(tetrahydro-2H-pyran-4-yloxy)-2,3-dihydrobenzo[b][1,4]dioxine-5-carboxylate

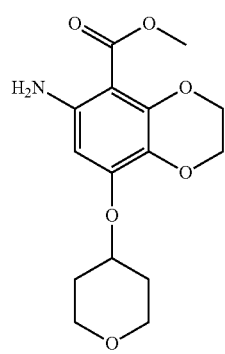

A solution of methyl 6-nitro-8-(tetrahydro-2H-pyran-4-yloxy)-2,3-dihydrobenzo[b][1,4]dioxine-5-carboxylate (1.2 g, 4 mmol) and zinc powder (1.3 g, 20 mmol) in acetic acid (10 mL) was stirred at 40° C. for 0.5 hour, filtered, concentrated, extracted with ethyl acetate (50 mL), washed with water, dried over Na$_2$SO$_4$ and concentrated in vacuum to obtain a yellow solid (1.1 g, 95% yield), MS: 310 (M+H$^+$).

Step 12: Preparation for 5-(Tetrahydro-2H-pyran-4-yloxy)-2,3-dihydro-[1,4]dioxino[2,3-f]quinazolin-10-ol

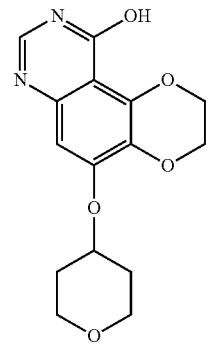 [SMILES: Oc1ncnc2cc(OC3CCOCC3)c3c(c12)OCCO3]

A solution of methyl 6-amino-8-(tetrahydro-2H-pyran-4-yloxy)-2,3-dihydrobenzo[b][1,4]dioxine-5-carboxylate (1.1 g, 4 mmol) in formamide (10 mL) was stirred at 150° C. for 20 hours, cooled, concentrated, washed with ethyl acetate, filtered and dried to obtain a pale solid (1.0 g, 95% yield). $^1$H NMR (DMSO-d$_6$, 400 MHz): δ 7.83 (s, 1H), 6.84 (s, 1H), 4.75 (dd, 1H, J=4 Hz), 4.32-4.29 (m, 4H), 3.87-3.84 (m, 2H), 3.54-3.49 (m, 2H), 2.01-1.99 (m, 2H), 1.64-1.60 (m, 2H). MS: 305 (M+H$^+$).

Step 13: Preparation for 10-Chloro-5-(tetrahydro-2H-pyran-4-yloxy)-2,3-dihydro-[1,4]dioxino[2,3-f]quinazoline

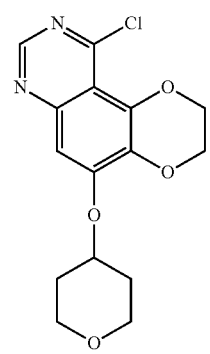 [SMILES: Clc1ncnc2cc(OC3CCOCC3)c3c(c12)OCCO3]

A solution of 5-(Tetrahydro-2H-pyran-4-yloxy)-2,3-dihydro-[1,4]dioxino[2,3-f]quinazolin-10-ol (1 g, 3.3 mmol) in Phosphorus oxychloride (15 mL) was stirred at 110° C. for 24 hours, cooled, poured into ice water (500 mL), adjusted pH to 8 with potassium carbonate, extracted with ethyl acetate, dried over Na$_2$SO$_4$, filtered and concentrated to obtain a yellow solid (0.5 g, 45% yield). MS: 323 (M+H$^+$).

Step 14: Preparation for N-(3-Ethynylphenyl)-5-(tetrahydro-2H-pyran-4-yloxy)-2,3-dihydro-[1,4]dioxino[2,3-f]quinazolin-10-amine

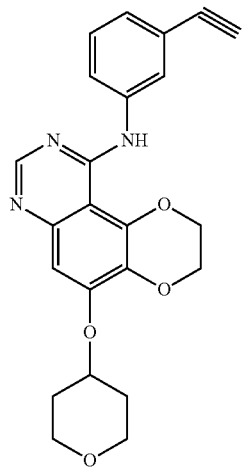 [SMILES: C#Cc1cccc(Nc2ncnc3cc(OC4CCOCC4)c4c(c23)OCCO4)c1]

To a solution of 10-Chloro-5-(tetrahydro-2H-pyran-4-yloxy)-2,3-dihydro-[1,4]dioxino[2,3-f]quinazoline (0.1 g, 0.3 mmol) in isopropanol (3 mL) was added 3-ethynylaniline (0.042 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=50%). $^1$H NMR (DMSO-$d_6$, 400 MHz): δ 10.53 (s, 1H), 8.75 (s, 1H), 7.79 (s, 1H), 7.69 (d, 1H, J=8 Hz), 7.49 (t, 1H, J=8.0 Hz), 7.42 (d, 1H, 8 Hz), 7.31 (s, 1H), 4.76 (dd, 1H, J=4.4 Hz), 4.62 (s, 2H), 4.42 (s, 2H), 3.92-3.89 (m, 2H), 3.55-3.51 (m, 2H), 2.11-2.07 (m, 2H), 1.71-1.69 (m, 2H); MS: 404 (M+H$^+$).

Example 22

N-(4-Chloro-3-fluorophenyl)-5-(tetrahydro-2H-pyran-4-yloxy)-2,3-dihydro-[1,4]dioxino[2,3-f]-quinazolin-10-amine (I-22)

Step 1 to 6 is the same as in example 1;
Step 7 to 13 is the same as in example 21;

Step 14: Preparation for N-(4-Chloro-3-fluorophenyl)-5-(tetrahydro-2H-pyran-4-yloxy)-2,3-dihydro-[1,4]dioxino[2,3-f]-quinazolin-10-amine

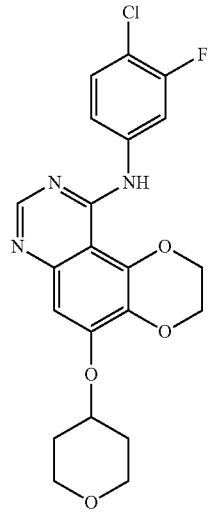 [SMILES: Fc1cc(Nc2ncnc3cc(OC4CCOCC4)c4c(c23)OCCO4)ccc1Cl]

To a solution of 10-Chloro-5-(tetrahydro-2H-pyran-4-yloxy)-2,3-dihydro-[1,4]dioxino[2,3-f]quinazoline (0.1 g, 0.3 mmol) in isopropanol (3 mL) was added 4-chloro-3-fluoroaniline (0.06 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.07 g, yield=49%). $^1$H NMR (DMSO-$d_6$, 400 MHz): 10.51 (s, 1H), 8.75 (s, 1H), 7.95-7.92 (m, 1H), 7.65-7.64 (m, 1H), 7.54 (t, 1H, J=8.9 Hz), 7.30 (s, 1H), 4.77 (dd, 1H, J=4.4 Hz), 4.61 (br, 2H), 4.60 (br, 2H), 3.92-3.89 (m, 2H), 3.56-3.50 (m, 2H), 2.10-2.07 (m, 2H), 1.72-1.69 (m, 2H); MS: 432 (M+H$^+$).

Example 23

N-(4-Chloro-3-fluorophenyl)-5-(tetrahydrofuran-3-yloxy)-2,3-dihydro-[1,4]dioxino[2,3-f]quinazolin-10-amine (I-23)

Step 1 to 6 is the same as in example 1;

Preparation for tetrahydrofuran-3-yl 4-methylbenzenesulfonate

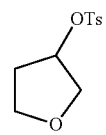 [SMILES: Cc1ccc(S(=O)(=O)OC2CCOC2)cc1]

To a solution of tetrahydrofuran-3-ol (2 g, 23 mmol) and 4-methylbenzene-1-sulfonyl chloride (5 g, 26 mmol) in dichloromethane (15 mL) was added pyridine (15 mL) at 0° C. The solution was stirred at ambient temperature for 24 hours, washed with hydrochloric acid (1 mol/L), extracted with ethyl acetate and washed with saturated brine. The obtained organic layer was dried over magnesium sulfate, filtered and concentrated to obtain a light yellow oily crude product (5 g, 91% yield).

Step 7: Preparation for Methyl 8-(tetrahydrofuran-3-yloxy)-2,3-dihydrobenzo[b][1,4]dioxine-5-carboxylate

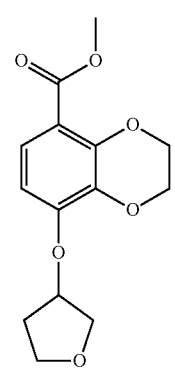 [SMILES: COC(=O)c1ccc(OC2CCOC2)c2c1OCCO2]

To a solution of methyl 8-hydroxy-2,3-dihydrobenzo[b][1,4]dioxine-5-carboxylate (4 g, 19 mmol) and potassium carbonate (4.2 g, 30 mmol) in DMF (15 mL) was added tetrahydrofuran-3-yl 4-methylbenzenesulfonate (5 g, 21 mmol). The mixture was stirred at 80° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (4.3 g, yield=81%); MS: 281 (M+H$^+$).

Step 8: Preparation for Methyl 6-nitro-8-(tetrahydrofuran-3-yloxy)-2,3-dihydrobenzo[b][1,4]dioxine-5-carboxylate

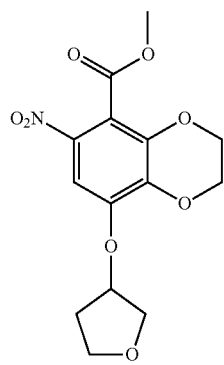 [SMILES: COC(=O)c1c([N+](=O)[O-])cc(OC2CCOC2)c2c1OCCO2]

To a solution of Methyl 8-(tetrahydrofuran-3-yloxy)-2,3-dihydrobenzo[b][1,4]dioxine-5-carboxylate (1.1 g, 4 mmol) in acetic acid (9 mL) at 0° C. was added a mixture of acetic acid (3 mL) and nitric acid (6 mL) dropwise. After that the mixture was stirred for 1 hour, poured into ice water (500 mL), stirred for another 1 hour, filtered and dried to obtain a yellow solid (1.2 g, 95% yield).

Step 9: Preparation for Methyl 6-amino-8-(tetrahydrofuran-3-yloxy)-2,3-dihydrobenzo[b][1,4]dioxine-5-carboxylate

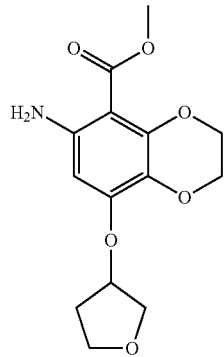

A solution of Methyl 6-nitro-8-(tetrahydrofuran-3-yloxy)-2,3-dihydrobenzo[b][1,4]dioxine-5-carboxylate (1.2 g, 4 mmol) and zinc powder (1.3 g, 20 mmol) in acetic acid (10 mL) was stirred at 40° C. for 0.5 hour, filtered, concentrated, extracted with ethyl acetate (50 mL), washed with water, dried over Na$_2$SO$_4$ and concentrated in vacuum to obtain a yellow solid (1.1 g, yield=95%). MS: 296 (M+H$^+$).

Step 10: Preparation for 5-(Tetrahydrofuran-3-yloxy)-2,3-dihydro-[1,4]dioxino[2,3-f]quinazolin-10-ol

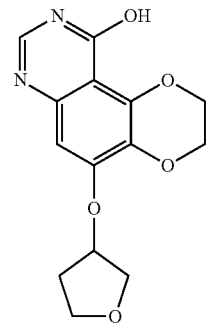 [SMILES: Oc1ncnc2cc(OC3CCOC3)c3c(c12)OCCO3]

A solution of Methyl 6-amino-8-(tetrahydrofuran-3-yloxy)-2,3-dihydrobenzo[b][1,4]dioxine-5-carboxylate (1.1 g, 4 mmol) in formamide (10 mL) was stirred at 150° C. for 20 hours, cooled, concentrated, washed with ethyl acetate, filtered and dried to obtain a pale solid (1.0 g, 95% yield). MS: 291 (M+H$^+$).

Step 11: Preparation for 10-chloro-5-(tetrahydrofuran-3-yloxy)-2,3-dihydro-[1,4]dioxino[2,3-f]quinazoline

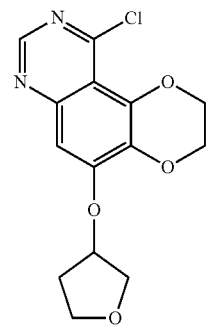 [SMILES: Clc1ncnc2cc(OC3CCOC3)c3c(c12)OCCO3]

A solution of 5-(tetrahydrofuran-3-yloxy)-2,3-dihydro-[1,4]dioxino[2,3-f]quinazolin-10-ol (1 g, 3.3 mmol) in Phosphorus oxychloride (15 mL) was stirred at 110° C. for 24 hours, cooled, poured into ice water (500 mL), adjusted pH to 8 with potassium carbonate, extracted with ethyl acetate, dried over Na$_2$SO$_4$, filtered and concentrated to obtain a yellow solid (0.5 g, yield=45%). MS: 309 (M+H$^+$).

Step 12: Preparation for N-(4-Chloro-3-fluorophenyl)-5-(tetrahydrofuran-3-yloxy)-2,3-dihydro-[1,4]dioxino[2,3-f]quinazolin-10-amine

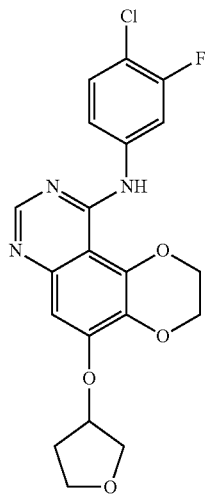 [SMILES: Fc1cc(Nc2ncnc3cc(OC4CCOC4)c4c(c23)OCCO4)ccc1Cl]

To a solution of 10-chloro-5-(tetrahydrofuran-3-yloxy)-2,3-dihydro-[1,4]dioxino[2,3-f]quinazoline (0.1 g, 0.3 mmol) in isopropanol (3 mL) was added 4-chloro-3-fluoroaniline (0.06 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.09 g, yield=62%). $^1$H NMR (DMSO-d$_6$, 400 MHz): δ 10.45 (s, 1H), 8.73 (s, 1H), 7.97-7.94 (m, 1H), 7.66-7.65 (m, 1H), 7.54 (t, 1H, J=8.9 Hz), 7.14 (s, 1H), 5.20-5.18 (m, 1H), 4.61-4.59 (m, 2H), 4.45-4.44 (m, 2H), 3.96-3.88 (m, 3H), 3.81-3.79 (m, 1H), 2.37-2.34 (m, 1H), 2.08-2.06 (m, 1H). MS: 418 (M+H$^+$).

Example 24

N-(3-Ethynylphenyl)-5-(tetrahydrofuran-3-yloxy)-23-dihydro-[1,4]dioxino[2,3-f]quinazolin-10-amine (I-24)

Step 1 to 6 is the same as in example 1;
Step 7 to 11 is the same as in example 23;

Step 12: Preparation for N-(3-Ethynylphenyl)-5-(tetrahydrofuran-3-yloxy)-2,3-dihydro-[1,4]dioxino[2,3-f]quinazolin-10-amine

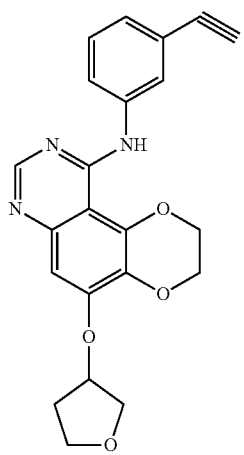 [SMILES: C#Cc1cccc(Nc2ncnc3cc(OC4CCOC4)c4c(c23)OCCO4)c1]

To a solution of 10-chloro-5-(tetrahydrofuran-3-yloxy)-2,3-dihydro-[1,4]dioxino[2,3-f]quinazoline (0.1 g, 0.3 mmol) in isopropanol (3 mL) was added 3-ethynylaniline (0.042 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.07 g, yield=52%). $^1$H NMR (DMSO-d$_6$, 400 MHz): δ 10.43 (s, 1H), 8.72 (s, 1H), 7.83 (s, 1H), 7.71 (d, 1H, J=8 Hz), 7.48 (t, 1H, J=8 Hz), 7.40 (d, 1H, J=8 Hz), 7.07 (s, 1H), 5.21-5.19 (m, 1H), 4.62-4.61 (m, 2H), 4.45-4.44 (m, 2H), 4.28 (s, 1H), 3.98-3.88 (m, 3H), 3.81-3.77 (m, 1H), 2.37-2.34 (m, 1H), 2.08-2.06 (m, 1H). MS: 390 (M+H$^+$).

Example 25

N-(3-Chloro-4-fluorophenyl)-5-(1-methoxypropan-2-yloxy)-2,3-dihydro-[1,4]dioxino[2,3-H]quinazolin-10-amine (I-25)

Step 1 to 6 is the same as in example 1;

Step 7: Preparation for methyl 8-(1-methoxypropan-2-yloxy)-2,3-dihydrobenzo[b][1,4]dioxine-5-carboxylate

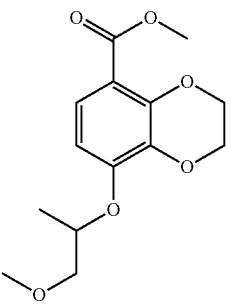 [SMILES: COCC(C)Oc1ccc(C(=O)OC)c2c1OCCO2]

To a solution of methyl 8-hydroxy-2,3-dihydrobenzo[b][1,4]dioxine-5-carboxylate (2.1 g, 10 mmol), PPh$_3$ (4.6 g, 15 mmol), diethyl azodicarboxylate (2.6 g, 15 mmol) in THF (70 mL) was added 1-methoxypropan-2-ol (1.0 g, 11 mmol) with stirring at room temperature for 20 hours. And then the resulting mixture was concentrated to obtain a yellow solid which was purified by column chromatography on silicon gel (PE:EA=5:1) to obtained a white solid (2.7 g, yield=95%). MS: 283 (M+H$^+$).

Step 8: Preparation for methyl 8-(1-methoxypropan-2-yloxy)-6-nitro-2,3-dihydrobenzo[b][1,4]dioxine-5-carboxylate

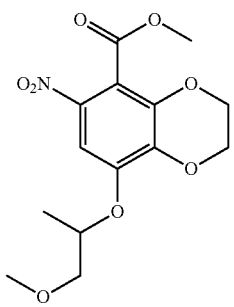 [SMILES: COCC(C)Oc1cc([N+](=O)[O-])c(C(=O)OC)c2c1OCCO2]

To a solution of Methyl 8-(1-methoxypropan-2-yloxy)-2,3-dihydrobenzo[b][1,4]dioxine-5-carboxylate (2.5 g, 8.8 mmol) in acetic acid (24 mL) at 0° C. was added a mixture of acetic acid (8 mL) and nitric acid (16 mL) dropwise. After that the mixture was stirred for 1 hour, poured into ice water (500 mL), stirred for another 1 hour, filtered and dried to obtain a yellow solid (2.7 g, yield=95%).

Step 9: Preparation for Methyl 6-amino-8-(1-methoxypropan-2-yloxy)-2,3-dihydrobenzo[b][1,4]dioxine-5-carboxylate

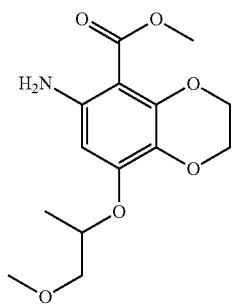 [SMILES: COCC(C)Oc1cc(N)c(C(=O)OC)c2c1OCCO2]

A solution of methyl 8-(1-methoxypropan-2-yloxy)-6-nitro-2,3-dihydrobenzo[b][1,4]dioxine-5-carboxylate (2.6 g, 8 mmol) and zinc powder (2.6 g, 40 mmol) in acetic acid (20 mL) was stirred at 40° C. for 0.5 hour, filtered, concentrated, extracted with ethyl acetate (50 mL), washed with water, dried over Na$_2$SO$_4$ and concentrated in vacuum to obtain a yellow solid (2.4 g, yield=95%). MS: 298 (M+H$^+$).

Step 10: Preparation for 5-(1-Methoxypropan-2-yloxy)-2,3-dihydro-[1,4]dioxino[2,3-f]quinazolin-10-ol

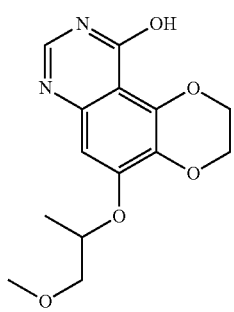 [SMILES: COCC(C)Oc1cc2ncnc(O)c2c2c1OCCO2]

A solution of Methyl 6-amino-8-(1-methoxypropan-2-yloxy)-2,3-dihydrobenzo[b][1,4]dioxine-5-carboxylate (2.4 g, 7.7 mmol) in formamide (10 mL) was stirred at 150° C. for 20 hours, cooled, concentrated, washed with ethyl acetate, filtered and dried to obtain a pale solid (2.2 g, yield=95%). MS: 293 (M+H$^+$).

Step 11: Preparation for 10-Chloro-5-(1-methoxypropan-2-yloxy)-2,3-dihydro-[1,4]dioxino[2,3-f]quinazoline

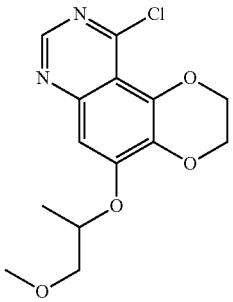 [SMILES: COCC(C)Oc1cc2ncnc(Cl)c2c2c1OCCO2]

A solution of 5-(1-Methoxypropan-2-yloxy)-2,3-dihydro-[1,4]dioxino[2,3-f]quinazolin-10-ol (2 g, 6.8 mmol) in Phosphorus oxychloride (15 mL) was stirred at 110° C. for 24 hours, cooled, poured into ice water (500 mL), adjust the PH=8 with potassium carbonate, extracted with ethyl acetate, dried over Na$_2$SO$_4$, filtered and concentrated to obtain a yellow solid (1.1 g, yield=53%). MS: 311 (M+H$^+$).

Step 12: Preparation for N-(3-Chloro-4-fluorophenyl)-5-(1-methoxypropan-2-yloxy)-2,3-dihydro-[1,4]dioxino[2,3-f]quinazolin-10-amine

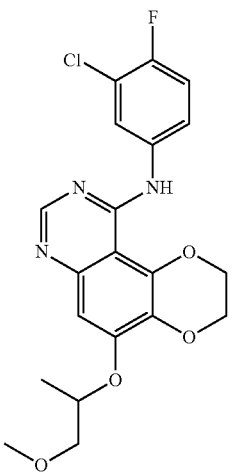 [SMILES: COCC(C)Oc1cc2ncnc(Nc3ccc(F)c(Cl)c3)c2c2c1OCCO2]

To a solution of 10-Chloro-5-(1-methoxypropan-2-yloxy)-2,3-dihydro-[1,4]dioxino[2,3-f]quinazoline (0.1 g, 0.3 mmol) in isopropanol (3 mL) was added 4-chloro-3-fluoroaniline (0.06 g, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.09 g, yield=62%). $^1$H NMR (DMSO-d$_6$, 400 MHz): δ 10.52 (s, 1H), 8.75 (s, 1H), 7.95-7.92 (m, 1H), 7.66-7.63 (m, 1H), 7.54 (t, 1H, J=8.9 Hz), 7.21 (s, 1H), 4.83-4.78 (m, 1H), 4.60 (br, 2H), 4.45 (br, 2H), 3.60-3.58 (m, 2H), 3.31 (s, 3H), 1.33 (d, 3H, J=6.4 Hz); MS: 420 (M+H$^+$).

Example 26

N-(3-Ethynylphenyl)-5-(1-methoxypropan-2-yloxy)-2,3-dihydro-[1,4]dioxino[2,3-f]quinazolin-10-amine (I-26)

Step 1 to 6 is the same as in example 1;
Step 7 to 11 is the same as in example 25;

Step 12: Preparation for N-(3-Ethynylphenyl)-5-(1-methoxypropan-2-yloxy)-2,3-dihydro-[1,4]dioxino[2,3-f]quinazolin-10-amine

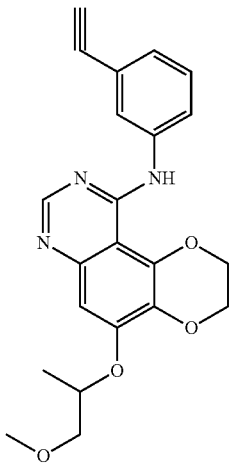 [SMILES: C#Cc1cccc(Nc2ncnc3cc(OC(C)COC)c4c(c23)OCCO4)c1]

To a solution of 10-Chloro-5-(1-methoxypropan-2-yloxy)-2,3-dihydro-[1,4]dioxino[2,3-f]quinazoline (0.1 g, 0.3 mmol) in isopropanol (3 mL) was added 3-ethynylaniline (0.042 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.08 g, yield=59%). $^1$H NMR (DMSO-$d_6$, 400 MHz): δ 9.65 (s, 1H), 8.43 (s, 1H), 8.07 (s, 1H), 7.89-7.87 (m, 1H), 7.38 (t, 1H, J=8 Hz), 7.22-7.20 (m, 1H), 6.94 (s, 1H), 4.88-4.83 (m, 1H), 4.60 (br, 2H), 4.41 (br, 2H), 4.20 (s, 1H), 3.57-3.53 (m, 2H), 3.31 (s, 3H), 1.29 (d, 3H, J=6.4 Hz); MS: 392 (M+H$^+$).

Example 27

N-(3-Chloro-4-((3-fluorobenzyl)oxy)phenyl)-5-isopropoxy-2,3-dihydro-[1,4]dioxino[2,3-f]quinazolin-10-amine (I-27)

Step 1 to 11 is the same as in example 1;

Step 12: Preparation for N-(3-Chloro-4-((3-fluorobenzyl)oxy)phenyl)-5-isopropoxy-2,3-dihydro-[1,4]dioxino[2,3-f]quinazolin-10-amine

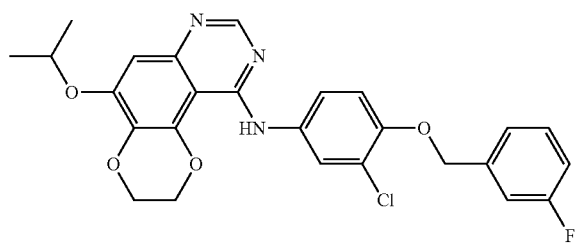 [SMILES: CC(C)Oc1cc2ncnc(Nc3ccc(OCc4cccc(F)c4)c(Cl)c3)c2c2c1OCCO2]

To a solution of 10-chloro-5-isopropoxy-2,3-dihydro-[1,4]dioxino[2,3-f]quinazoline (0.1 g, 0.3 mmol) in butyl alcohol (3 mL) was added 3-chloro-4-((3-fluorobenzyl)oxy)aniline (0.075 g, 0.30 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.090 g, yield=50%). $^1$H NMR (DMSO-$d_6$, 400 MHz): δ 8.64-8.62 (m, 2H), 7.51-7.47 (m, 1H), 7.33-7.31 (m, 1H), 7.19-7.18 (m, 1H), 6.98-6.97 (m, 3H), 5.31 (s, 2H), 4.73-4.70 (m, 3H), 4.58 (br, 1H), 4.43 (br, 1H), 1.34 (d, 6H, J=6 Hz); MS: 492 (M+H)$^+$.

Example 28

N-(3-Ethynylphenyl)-5-methoxy-2,3-dihydro-[1,4]dioxino[2,3-f]quinazolin-10-amine (I-28)

Step 1: Preparation for methyl 8-methoxy-2,3-dihydrobenzo[b][1,4]dioxine-5-carboxylate

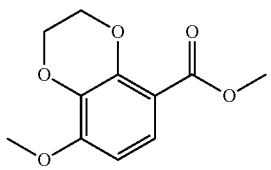

To a solution of methyl 8-hydroxy-2,3-dihydrobenzo[b][1,4]dioxine-5-carboxylate (4.2 g, 20 mmol) and potassium carbonate (4.2 g, 30 mmol) in DMF (15 mL) was added iodomethane (1.5 mL, 24 mmol). The mixture was stirred at 80° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (4.2 g, yield=95%). $^1$H NMR (CDCl$_3$, 400 MHz, δ ppm): 3.88 (s, 3H), 3.94 (s, 3H), 4.37-4.40 (m, 4H), 6.53 (d, J=4.4 Hz, 1H), 7.51 (d, J=4.4 Hz, 1H).

Step 2: Preparation for methyl 8-methoxy-6-nitro-2,3-dihydrobenzo[b][1,4]dioxine-5-carboxylate

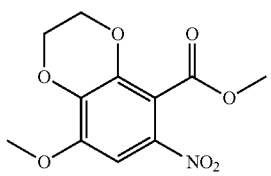

To a solution of methyl 8-methoxy-2,3-dihydrobenzo[b][1,4]dioxine-5-carboxylate (4.2 g, 0.019 mol) in acetic acid was added nitric acid (20 mL) with the temperature below 10° C. with stirring for 4 hours, poured into ice water (100 mL), filtered, washed with water to pH 7 and dried to obtain a yellow solid (4.0 g, yield=79%). $^1$H NMR (CDCl$_3$, 400 MHz, δ ppm): 3.97 (s, 3H), 3.99 (s, 3H), 4.37-4.39 (m, 2H), 4.43-4.45 (m, 2H), 7.41 (s, 1H).

Step 3: Preparation for methyl 6-amino-8-methoxy-2,3-dihydrobenzo[b][1,4]dioxine-5-carboxylate

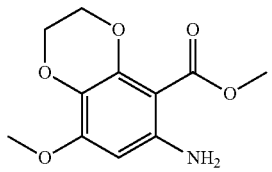

To a solution of methyl 8-methoxy-6-nitro-2,3-dihydrobenzo[b][1,4]dioxine-5-carboxylate (2.69 g, 0.01 mol) in methanol (50 mL) was added Palladium on activated carbon 5% Pd with stirring under hydrogen atmosphere for 8 hours. After that the mixture was filtered and concentrated to obtain a pale solid which was re-crystallized in ethanol to obtain a white solid (2.4 g, yield=95%). $^1$H NMR (CDCl$_3$, 400 MHz, δ ppm): 3.87 (s, 3H), 3.88 (s, 3H), 4.27-4.29 (m, 2H), 4.31-4.33 (m, 2H), 5.32 (s, 2H), 5.84 (s, 1H).

Step 4: Preparation for 5-Methoxy-2,3-dihydro-[1,4]dioxino[2,3-f]quinazolin-10(9H)-one

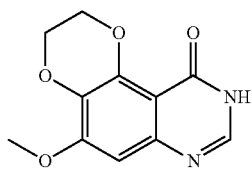 [SMILES: COc1cc2nc[nH]c(=O)c2c2c1OCCO2]

A solution of methyl 6-amino-8-methoxy-2,3-dihydrobenzo[b][1,4]dioxine-5-carboxylate (2.39 g, 0.01 mol) in formamide (30 mL) was stirred at 150° C. for 8-10 hours, cooled, concentrated, washed with ethyl acetate, filtered and dried to obtain a pale solid (2.3 g, yield=96%). $^1$H NMR (CDCl$_3$, 400 MHz, δ ppm): 3.87 (s, 3H), 4.26-4.31 (m, 4H), 6.75 (s, 1H), 7.85 (s, 1H), 11.75 (s, 1H).

Step 5: Preparation for 10-Chloro-5-methoxy-2,3-dihydro-[1,4]dioxino[2,3-f]quinazoline

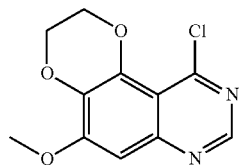 [SMILES: COc1cc2ncnc(Cl)c2c2c1OCCO2]

A solution of 5-Methoxy-2,3-dihydro-[1,4]dioxino[2,3-f]quinazolin-10(9H)-one (2.3 g, 0.01 mmol) in Phosphorus oxychloride (30 mL) was stirred at 110° C. for 6-8 hours, cooled, poured into ice water, adjust to pH 8 with potassium carbonate, extracted with ethyl acetate, dried over Na$_2$SO$_4$, filtered and concentrated to obtain a yellow solid (1.3 g, yield=55%). $^1$H NMR (CDCl$_3$, 400 MHz, δ ppm): 4.07 (s, 3H), 4.50 (s, 4H), 7.09 (s, 1H), 8.81 (s, 1H).

Step 6: Preparation for N-(3-Ethynylphenyl)-5-methoxy-2,3-dihydro-[1,4]dioxino[2,3-f]quinazolin-10-amine

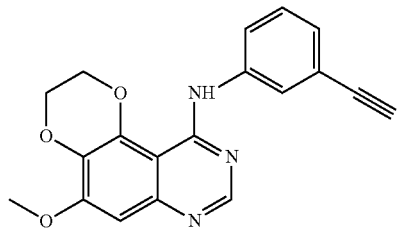 [SMILES: C#Cc1cccc(Nc2ncnc3cc(OC)c4c(c23)OCCO4)c1]

To a solution of 10-Chloro-5-methoxy-2,3-dihydro-[1,4]dioxino[2,3-f]quinazoline (1.3 g, 0.005 mol) in isopropanol (20 mL) was added 3-ethynylaniline (1.35 g, 0.012 mol). The solution was stirred at reflux for until the regent was not detected by TLC. After cooling to ambient temperature, the mixture was filtered to obtain a yellow solid which was washed with isopropanol to obtain a white solid (0.83 g, yield=51%). $^1$H NMR (MeOD-d$_6$, 400 MHz, δ ppm): 3.61 (s, 1H), 4.06 (s, 3H), 4.50 (t, J=3.6 Hz, 2H), 4.69 (t, 7=3.6 Hz, 2H), 5.50 (s, 1H), 6.90 (s, 1H), 7.41-7.47 (m, 2H), 7.70 (d, J=3.8 Hz, 1H), 7.88 (s, 1H), 8.60 (s, 1H); MS: 334.1 (M+H$^+$).

Example 29

N-(3-Chloro-4-fluorophenyl)-5-methoxy-2,3-dihydro-[1,4]dioxino[2,3-f]quinazolin-10-amine (I-29)

Step 1 to 5 is the same as in example 28;

Step 6: Preparation for N-(3-Chloro-4-fluorophenyl)-5-methoxy-2,3-dihydro-[1,4]dioxino[2,3-f]quinazolin-10-amine

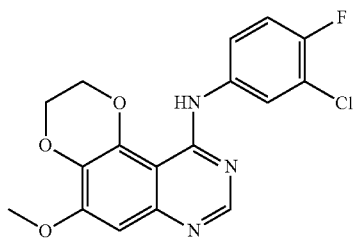 [SMILES: COc1cc2ncnc(Nc3ccc(F)c(Cl)c3)c2c2c1OCCO2]

To a solution of 10-Chloro-5-methoxy-2,3-dihydro-[1,4]dioxino[2,3-f]quinazoline (0.1 g, 0.4 mmol) in isopropanol (2 mL) was added 4-fluoro-3-chloroaniline (60 mg, 0.4 mmol). The solution was stirred at reflux for until the regent was not detected by TLC. After cooling to ambient temperature, the mixture was filtered to obtain a yellow solid which was washed with isopropanol to obtain a yellow solid (0.08 g, yield=50%). $^1$H NMR (CDCl$_3$, 400 MHz, δ ppm): 3.98 (s, 3H), 4.44 (q, J=4.6 Hz, 2H), 4.60 (q, J=4.6 Hz, 2H), 7.08 (s, 1H), 7.54 (t, J=9.2 Hz, 1H), 7.63-7.67 (m, 1H), 7.94 (q, y=6.8 Hz, 1H), 8.75 (s, 1H), 10.50 (s, 1H); MS: 362.1 (M+H$^+$).

Example 30

N-(3-Chloro-4-fluorophenyl)-5-(2-methoxyethoxy)-2,3-dihydro-[1,4]dioxino[2,3-f]quinazolin-10-amine (I-30)

Step 1 to 5 is the same as in example 28;

Step 6: Preparation for N-(3-Chloro-4-fluorophenyl)-5-(2-methoxyethoxy)-2,3-dihydro-[1,4]dioxino[2,3-f]quinazolin-10-amine

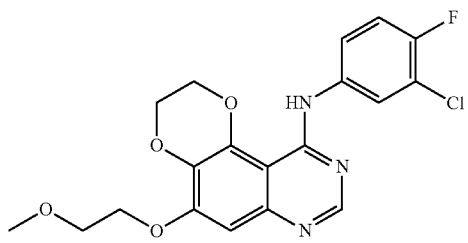 [SMILES: COCCOc1cc2ncnc(Nc3ccc(F)c(Cl)c3)c2c2c1OCCO2]

To a solution of 10-Chloro-5-(2-methoxyethoxy)-2,3-dihydro-[1,4]dioxino[2,3-f]quinazoline (0.1 g, 0.4 mmol) in isopropanol (3 mL) was added 4-fluoro-3-chloroaniline (60 mg, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=40%). $^1$H NMR (CDCl$_3$, 400 MHz, δ ppm): 3.47 (s, 3H), 3.83 (t, J=4.0 Hz, 2H), 4.34 (t, J=4.2 Hz, 2H), 4.56 (t, J=2.0 Hz, 2H), 4.69 (t, J=3.8 Hz, 2H), 7.26 (t, J=7.6 Hz, 1H), 7.56-7.60 (m, 1H), 7.64 (s, 1H), 7.82 (q, J=6.4 Hz, 1H), 8.64 (s, 1H), 10.00 (s, 1H); MS: 406.1 (M+H$^+$).

Example 31

N-(3-Ethynylphenyl)-5-(2-methoxyethoxy)-2,3-dihydro-[1,4]dioxino[2,3-f]quinazolin-10-amine (I-31)

Step 1 to 5 is the same as in example 28;

Step 6: Preparation for N-(3-Ethynylphenyl)-5-(2-methoxyethoxy)-2,3-dihydro-[1,4]dioxino[2,3-f]quinazolin-10-amine

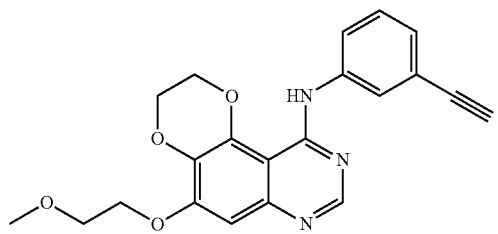 [SMILES: C#Cc1cccc(Nc2ncnc3cc(OCCOC)c4c(c23)OCCO4)c1]

To a solution of 10-Chloro-5-(2-methoxyethoxy)-2,3-dihydro-[1,4]dioxino[2,3-f]quinazoline (0.1 g, 0.4 mmol) in isopropanol (3 mL) was added 3-ethynylaniline (60 mg, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=42%). $^1$H NMR (CDCl$_3$, 400 MHz, δ ppm): 3.18 (s, 1H), 3.47 (s, 3H), 3.82 (t, J=4.0 Hz, 2H), 4.34 (t, J=4.0 Hz, 2H), 4.55 (s, 2H), 4.69 (s, 2H), 7.44 (d, J=2.4 Hz, 2H), 7.64 (s, 1H), 7.74 (s, 1H), 7.79 (s, 1H), 8.47 (s, 1H), 10.06 (s, 1H). MS: 406.1 (M+H$^+$). MS: 378.1 (M+H$^+$).

Example 32

N-(4-fluorophenyl)-5-(2-methoxyethoxy)-2,3-dihydro-[1,4]dioxino[2,3-f]quinazolin-10-amine (I-32)

Step 1 to 5 is the same as in example 28;

Step 6: Preparation for N-(4-fluorophenyl)-5-(2-methoxyethoxy)-2,3-dihydro-[1,4]dioxino[2,3-f]quinazolin-10-amine

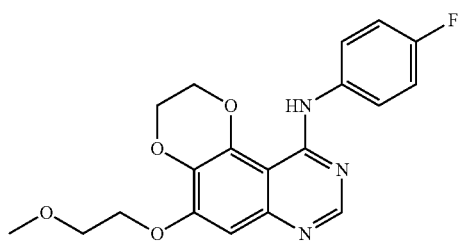 [SMILES: COCCOc1cc2ncnc(Nc3ccc(F)cc3)c2c2c1OCCO2]

To a solution of 10-chloro-5-(2-methoxyethoxy)-2,3-dihydro-[1,4]dioxino[2,3-f]quinazoline (0.1 g, 0.34 mmol) in isopropanol (3 mL) was added 4-fluoroaniline (0.040 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.07 g, yield=52%). $^1$H NMR (CDCl$_3$, 400 MHz, δ ppm): 3.33 (s, 3H), 3.72 (t, J=4.0 Hz, 2H), 4.24 (t, J=4.0 Hz, 2H), 4.40 (t, J=4.0 Hz, 2H), 4.58 (s, 2H), 6.88 (s, 1H), 7.21 (t, J=8.8 Hz, 2H), 7.82 (t, J=5.2 Hz, 2H), 8.36 (s, 1H), 9.55 (s, 1H); MS: 372.1 (M+H$^+$).

Example 33

5-(2-Methoxyethoxy)-N-(3-methoxyphenyl)-2,3-dihydro-[1,4]dioxino[2,3-f]quinazolin-10-amine (I-33)

Step 1 to 5 is the same as in example 28;

Step 6: Preparation for 5-(2-Methoxyethoxy)-N-(3-methoxyphenyl)-2,3-dihydro-[1,4]dioxino[2,3-f]quinazolin-10-amine

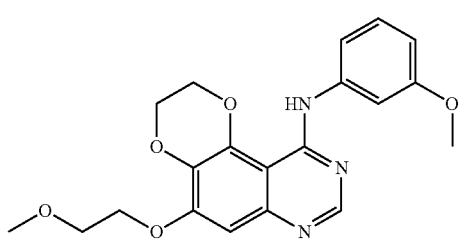

To a solution of 10-chloro-5-(2-methoxyethoxy)-2,3-dihydro-[1,4]dioxino[2,3-f]quinazoline (0.1 g, 0.34 mmol) in isopropanol (3 mL) was added 3-methoxyaniline (0.040 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=44%). $^1$H NMR (CDCl$_3$, 400 MHz, δ ppm): 3.47 (s, 3H), 3.83 (t, J=4.0 Hz, 2H), 3.88 (s, 3H), 4.35 (t, J=4.2 Hz, 2H), 4.55 (d, J=2.0 Hz, 2H), 4.67 (d, J=2.0 Hz, 2H), 6.88 (q, J=8.4 Hz, 1H), 7.19 (d, J=4.0 Hz, 1H), 7.33-7.41 (m, 2H), 8.47 (s, 1H), 10.05 (s, 1H); MS: 384.2 (M+H$^+$).

Example 34

5-Ethoxy-N-(4-fluorophenyl)-2,3-dihydro-[1,4]dioxino[2,3-f]quinazolin-10-amine (I-34)

Step 1: Preparation for methyl 8-ethoxy-2,3-dihydrobenzo[b][1,4]dioxine-5-carboxylate

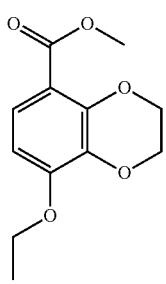

To a solution of methyl 8-hydroxy-2,3-dihydrobenzo[b][1,4]dioxine-5-carboxylate (4.20 g, 20 mmol) and potassium carbonate (4.14 g, 30 mmol) in DMF (50 mL) was added bromoethane (1.8 mL, 0.024 mol). The mixture was stirred at 70° C. for 2 hours. After cooling to ambient temperature, the solution was poured into ice water, filtered, washed with water and dried to obtain a yellow solid (4.3 g, yield=95%).

Step 2: Preparation for methyl 8-ethoxy-6-nitro-2,3-dihydrobenzo[b][1,4]dioxine-5-carboxylate

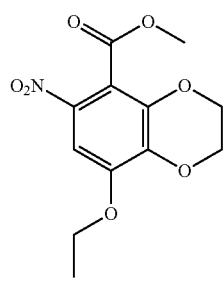

To a solution of methyl 8-ethoxy-2,3-dihydrobenzo[b][1,4]dioxine-5-carboxylate (4.2 g, 0.0176 mol) in acetic acid was added nitric acid (20 mL) with the temperature below 10° C. with stirring for 4 hours, poured into ice water (100 mL), filtered, washed with water to pH 7 and dried to obtain a yellow solid (4.1 g, yield=83%).

Step 3: Preparation for methyl 6-amino-8-ethoxy-2,3-dihydrobenzo[b][1,4]dioxine-5-carboxylate

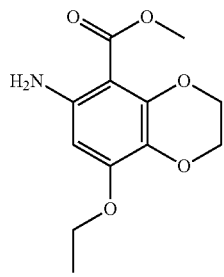 [SMILES: CCOc1cc([N+](=O)[O-])c(C(=O)OC)c2c1OCCO2]

To a solution of methyl 8-ethoxy-6-nitro-2,3-dihydrobenzo[b][1,4]dioxine-5-carboxylate (4.1 g, 14.5 mmol) in acetic acid (20 mL) was added zinc powder (2.6 g, 40 mmol) with stirring at 40° C. for 0.5 hour, filtered, concentrated, extracted with ethyl acetate (50 mL), washed with water, dried over Na$_2$SO$_4$, concentrated to obtain a yellow solid (3.5 g, yield=95%).

Step 4: Preparation for 5-Ethoxy-2,3-dihydro-[1,4]dioxino[2,3-f]quinazolin-10-ol

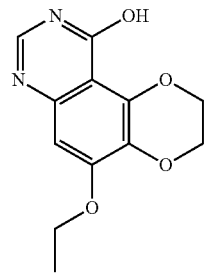 [SMILES: CCOc1cc2ncnc(O)c2c2c1OCCO2]

A solution of methyl 6-amino-8-ethoxy-2,3-dihydrobenzo[b][1,4]dioxine-5-carboxylate (3.5 g, 14 mmol) in formamide (10 mL) was stirred at 150° C. for 20 hours, cooled, concentrated, washed with ethyl acetate, filtered and dried to obtain a pale solid (3.5 g, yield=95%).

Step 5: Preparation for 10-Chloro-5-ethoxy-2,3-dihydro-[1,4]dioxino[2,3-f]quinazoline

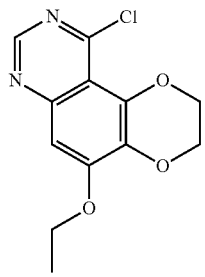 [SMILES: CCOc1cc2ncnc(Cl)c2c2c1OCCO2]

A solution of 5-ethoxy-2,3-dihydro-[1,4]dioxino[2,3-f]quinazolin-10(9H)-one (1 g, 0.04 mmol) in Phosphorus oxychloride (15 mL) was stirred at 110° C. for 24 hours, cooled, poured into ice water (500 mL), adjusted to pH 8 with potassium carbonate, extracted with ethyl acetate, dried over Na$_2$SO$_4$, filtered and concentrated to obtain a yellow solid (0.6 g, yield=55%).

Step 6: Preparation for 5-Ethoxy-N-(4-fluorophenyl)-2,3-dihydro-[1,4]dioxino[2,3-f]quinazolin-10-amine

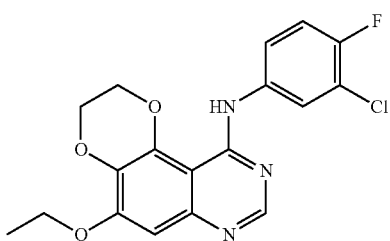 [SMILES: CCOc1cc2ncnc(Nc3ccc(F)c(Cl)c3)c2c2c1OCCO2]

To a solution of 10-Chloro-5-ethoxy-2,3-dihydro-[1,4]dioxino[2,3-f]quinazoline (0.1 g, 0.33 mmol) in isopropanol (3 mL) was added 4-fluoro-3-chloroaniline (60 mg, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=40%). $^1$H NMR (CDCl$_3$, 400 MHz, δ ppm): 1.56 (t, J=4.0 Hz, 3H), 4.06 (s, 3H), 2.35 (t, J=4.0 Hz, 2H), 4.56 (s, 2H), 4.67 (s, 2H), 7.28 (s, 1H), 7.71 (s, 1H), 7.78 (d, J=2.0 Hz, 1H), 8.56 (s, 1H), 9.89 (s, 1H); HRMS(ESI) m/z: C$_{18}$H$_{16}$ClFN$_3$O$_3$, calculated 376.0864 [M+H]$^+$, found 376.0861 [M+H]$^+$.

Example 35

5-Ethoxy-N-(3-ethynylphenyl)-2,3-dihydro-[1,4]dioxino[2,3-f]quinazolin-10-amine (I-35)

Step 1 to 5 is the same as in example 34;

Step 6: Preparation for 5-Ethoxy-N-(3-ethynylphenyl)-2,3-dihydro-[1,4]dioxino[2,3-f]quinazolin-10-amine

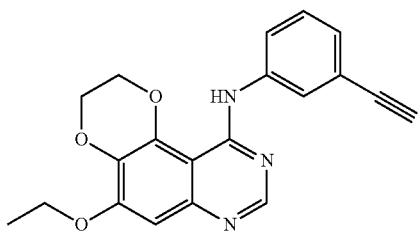 [SMILES: C#Cc1cccc(Nc2ncnc3cc(OCC)c4c(c23)OCCO4)c1]

To a solution of 10-Chloro-5-ethoxy-2,3-dihydro-[1,4]dioxino[2,3-f]quinazoline (0.1 g, 0.33 mmol) in isopropanol (3 mL) was added 3-ethynylaniline (40 mg, 0.33 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.065 g, yield=45%). $^1$H NMR (CDCl$_3$, 400 MHz, δ ppm): 1.54 (t, J=8.0 Hz, 3H), 3.18 (s, 1H), 4.31 (t, J=7.0 Hz, 2H), 4.57 (t, J=3.8 Hz, 2H), 4.69 (t, J=3.8 Hz, 2H), 7.45 (d, J=4.0 Hz, 2H), 7.67 (s, 1H), 7.74 (t, J=2.8 Hz, 1H), 7.81 (s, 1H), 8.50 (s, 1H), 10.02 (s, 1H). HRMS(ESI) m/z: C$_{20}$H$_{17}$N$_3$O$_3$, calculated 348.1348 [M+H]$^+$, found 348.1345 [M+H]$^+$.

Example 36

5-Ethoxy-N-(3-methoxyphenyl)-2,3-dihydro-[1,4]dioxino[2,3-f]quinazolin-10-amine (I-36)

Step 1 to 5 is the same as in example 34;

Step 6: Preparation for 5-Ethoxy-N-(3-methoxyphenyl)-2,3-dihydro-[1,4]dioxino[2,3-f]quinazolin-10-amine

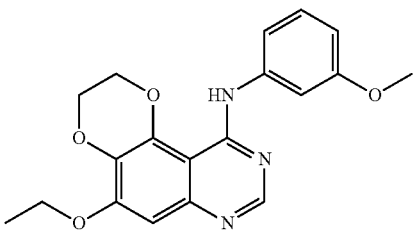 [SMILES: CCOc1cc2ncnc(Nc3cccc(OC)c3)c2c2c1OCCO2]

To a solution of 10-Chloro-5-ethoxy-2,3-dihydro-[1,4]dioxino[2,3-f]quinazoline (0.1 g, 0.33 mmol) in isopropanol (3 mL) was added 3-methoxyaniline (40 mg, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.09 g, yield=66%). $^1$H NMR (DMSO-d$_6$, 400 MHz, δ ppm): 1.43 (t, J=6.8 Hz, 3H), 3.74 (s, 3H), 4.21 (t, J=4.0 Hz, 2H), 4.45 (s, 2H), 4.62 (s, 2H), 6.90-6.93 (m, 1H), 7.11 (s, 1H), 7.20 (t, J=4.0 Hz, 1H), 7.27 (s, 1H), 7.38 (t, J=8.0 Hz, 1H), 8.72 (s, 1H). HRMS(ESI) m/z: C$_{20}$H$_{17}$N$_3$O$_3$, calculated 354.1454 [M+H]$^+$, found 354.1452 [M+H]$^+$.

Example 37

N-(3-Chloro-4-methylphenyl)-5-ethoxy-2,3-dihydro-[1,4]dioxino[2,3-f]quinazolin-10-amine (I-37)

Step 1 to 5 is the same as in example 34;

Step 6: Preparation for N-(3-Chloro-4-methylphenyl)-5-ethoxy-2,3-dihydro-[1,4]dioxino[2,3-f]quinazolin-10-amine

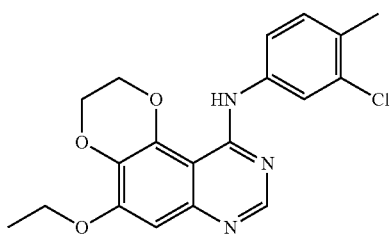 [SMILES: CCOc1cc2ncnc(Nc3ccc(C)c(Cl)c3)c2c2c1OCCO2]

To a solution of 10-chloro-5-ethoxy-2,3-dihydro-[1,4]dioxino[2,3-f]quinazoline (0.1 g, 0.34 mmol) in isopropanol (3 mL) was added 3-chloro-4-methylaniline (0.05 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.07 g, yield=52%). $^1$H NMR (DMSO-d$_6$, 400 MHz, δ ppm): 1.43 (t, J=8.0 Hz, 3H), 2.37 (s, 3H), 4.22 (q, J=12.0 Hz, 2H), 4.45 (s, 2H), 4.61 (s, 2H), 7.04 (s, 1H), 7.44 (d, J=4.0 Hz, 1H), 7.51-7.53 (m, 1H), 7.80 (s, 1H), 8.74 (s, 1H), 10.49 (s, 1H). HRMS(ESI) m/z: $C_{19}H_{18}ClN_3O_3$, calculated 372.1115 [M+H]$^+$, found 372.1112 [M+H]$^+$.

Example 38

5-Ethoxy-N-(3-nitrophenyl)-2,3-dihydro-[1,4]dioxino[2,3-f]quinazolin-10-amine (I-38)

Step 1 to 5 is the same as in example 34;

Step 6: Preparation for 5-Ethoxy-N-(3-nitrophenyl)-2,3-dihydro-[1,4]dioxino[2,3-f]quinazolin-10-amine

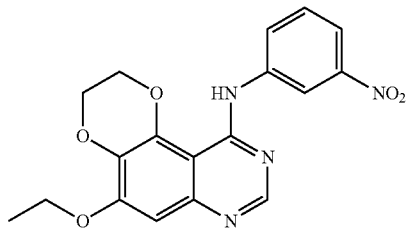 [SMILES: CCOc1cc2ncnc(Nc3cccc([N+](=O)[O-])c3)c2c2c1OCCO2]

To a solution of 10-chloro-5-ethoxy-2,3-dihydro-[1,4]dioxino[2,3-f]quinazoline (0.1 g, 0.34 mmol) in isopropanol (3 mL) was added 3-nitroaniline (0.05 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.06 g, yield=42%). $^1$H NMR (CDCl$_3$, 400 MHz, δ ppm): 1.57 (t, J=4.0 Hz, 3H), 4.35 (d, J=4.0 Hz, 2H), 4.59 (s, 2H), 4.71 (s, 2H), 7.65-7.69 (m, 1H), 7.72 (s, 2H), 8.15-8.20 (m, 2H), 8.53 (s, 2H), 10.01 (s, 1H). HRMS(ESI) m/z: $C_{18}H_{16}N_4O_5$, calculated 369.1199 [M+H]$^+$, found 369.1196 [M+H]$^+$.

Example 39

5-Ethoxy-N-p-tolyl-2,3-dihydro-[1,4]dioxino[2,3-f]quinazolin-10-amine (I-39)

Step 1 to 5 is the same as in example 34;

Step 6: Preparation for 5-Ethoxy-N-p-tolyl-2,3-dihydro-[1,4]dioxino[2,3-f]quinazolin-10-amine

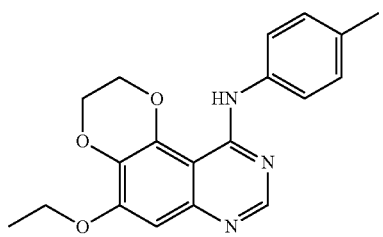 [SMILES: CCOc1cc2ncnc(Nc3ccc(C)cc3)c2c2c1OCCO2]

To a solution of 10-chloro-5-ethoxy-2,3-dihydro-[1,4]dioxino[2,3-f]quinazoline (0.1 g, 0.34 mmol) in isopropanol (3 mL) was added p-toluidine (0.04 g, 0.36 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.09 g, yield=65%). $^1$H NMR (CDCl$_3$, 400 MHz, δ ppm): 1.51 (t, J=6.0 Hz, 3H), 2.41 (s, 3H), 4.24 (q, J=13.8 Hz, 2H), 4.56 (q, J=4.6 Hz, 2H), 4.68 (q, J=4.6 Hz, 2H), 7.28 (d, J=1.4 Hz, 2H), 7.52-7.56 (m, 3H), 8.40 (s, 1H), 7.81 (s, 1H), 9.99 (s, 1H); HRMS(ESI) m/z: $C_{19}H_{19}N_3O_3$, calculated 338.1505 [M+H]$^+$, found 338.1507 [M+H]$^+$.

Example 40

N-(3-Chloro-4-fluorophenyl)-5-((tetrahydrofuran-2-yl)methoxy)-2,3-dihydro-[1,4]dioxino[2,3-f]quinazolin-10-amine (I-40)

Step 1: Preparation for methyl 8-((tetrahydrofuran-2-yl)methoxy)-2,3-dihydrobenzo[b][1,4]dioxine-5-carboxylate

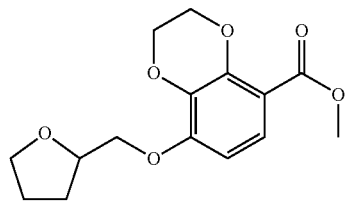 [SMILES: COC(=O)c1ccc(OCC2CCCO2)c2c1OCCO2]

To a solution of methyl 8-hydroxy-2,3-dihydrobenzo[b][1,4]dioxine-5-carboxylate (4.2 g, 20 mmol) and potassium carbonate (4.2 g, 30 mmol) in DMF (15 mL) was added 2-(bromomethyl)tetrahydrofuran (3.52 mL, 30 mmol). The mixture was stirred at 80° C. for 2 hours. After cooling to ambient temperature, the solution was quenched with water, extracted with ethyl acetate and washed with saturated brine. The obtained organic layer was dried over magnesium sulfate, filtered and concentrated to obtain a crude product as a white solid which was used in next step without further purification (4.3 g, yield=95%).

Step 2: Preparation for methyl 6-nitro-8-((tetrahydrofuran-2-yl)methoxy)-2,3-dihydrobenzo[b][1,4]dioxine-5-carboxylate

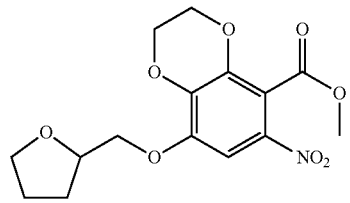 [SMILES: COC(=O)c1c([N+](=O)[O-])cc(OCC2CCCO2)c2c1OCCO2]

To a solution of methyl 8-((tetrahydrofuran-2-yl)methoxy)-2,3-dihydrobenzo[b][1,4]dioxine-5-carboxylate (4.3 g, 15 mmol) in acetic acid (42 mL) at 0° C. was added a mixture of acetic acid (14 mL) and nitric acid (28 mL) dropwise. After that the mixture was stirred for 1 hour, poured into ice water (500 mL), stirred for another 1 hour, filtered and dried to obtain a yellow solid (5.0 g, yield=95%).

Step 3: Preparation for methyl 6-amino-8-((tetrahydrofuran-2-yl)methoxy)-2,3-dihydrobenzo[b][1,4]dioxine-5-carboxylate

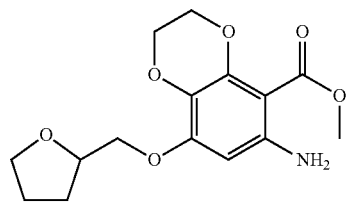 [SMILES: COC(=O)c1c(N)cc(OCC2CCCO2)c2c1OCCO2]

To a solution of methyl 6-nitro-8-((tetrahydrofuran-2-yl)methoxy)-2,3-dihydrobenzo[b][1,4]dioxine-5-carboxylate (5 g, 15 mmol) in acetic acid (20 mL) was added zinc powder (2.6 g, 40 mmol) with stirring at 40° C. for 0.5 hour, filtered, concentrated, extracted with ethyl acetate (50 mL), washed with water, dried over Na$_2$SO$_4$, concentrated to obtain a pale solid (4.5 g, yield=95%).

Step 4: Preparation for 5-((Tetrahydrofuran-2-yl)methoxy)-2,3-dihydro-[1,4]dioxino[2,3-f]quinazolin-10(9H)-one

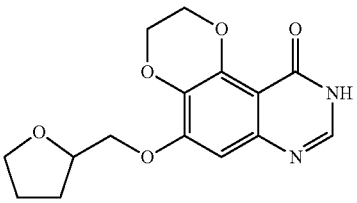 [SMILES: O=c1[nH]cnc2cc(OCC3CCCO3)c3c(c12)OCCO3]

A solution of methyl 6-amino-8-methoxy-2,3-dihydrobenzo[b][1,4]dioxine-5-carboxylate (4.5 g, 15 mmol) in formamide (15 mL) was stirred at 150° C. for 20 hours, cooled, concentrated, washed with ethyl acetate, filtered and dried to obtain a pale solid (4.5 g, yield=95%).

Step 5: Preparation for 10-Chloro-5-((tetrahydrofuran-2-yl)methoxy)-2,3-dihydro-[1,4]dioxino[2,3-f]quinazoline

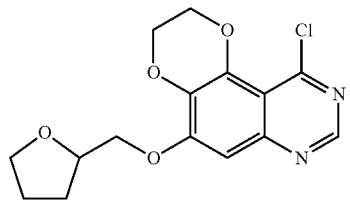 [SMILES: Clc1ncnc2cc(OCC3CCCO3)c3c(c12)OCCO3]

A solution of 5-((Tetrahydrofuran-2-yl)methoxy)-2,3-dihydro-[1,4]dioxino[2,3-f]quinazolin-10(9H)-one (1.5 g, 0.05 mmol) in Phosphorus oxychloride (15 mL) was stirred at 110° C. for 24 hours, cooled, poured into ice water (500 mL), adjusted to pH 8 with potassium carbonate, extracted with ethyl acetate, dried over Na$_2$SO$_4$, filtered and concentrated to obtain a yellow solid (0.7 g, yield=40%).

Step 6: Preparation for N-(3-Chloro-4-fluorophenyl)-5-((tetrahydrofuran-2-yl)methoxy)-2,3-dihydro-[1,4]dioxino[2,3-f]quinazolin-10-amine

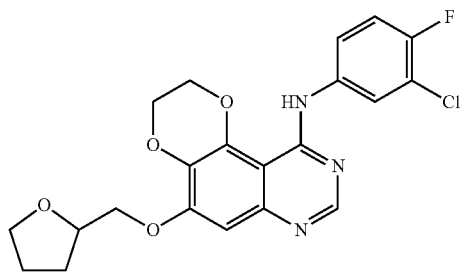 [SMILES: Fc1ccc(Nc2ncnc3cc(OCC4CCCO4)c4c(c23)OCCO4)cc1Cl]

To a solution of 10-Chloro-5-((tetrahydrofuran-2-yl)methoxy)-2,3-dihydro-[1,4]dioxino[2,3-f]quinazoline (0.15 g, 0.35 mmol) in isopropanol (3 mL) was added 4-fluoro-3-chloroaniline (60 mg, 0.4 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.10 g, yield=49%). $^1$H NMR (DMSO-d$_6$, 400 MHz, δ ppm): 1.72-2.04 (m, 4H), 3.70 (d, J=4.0 Hz, 1H), 3.82 (d, J=4.0 Hz, 1H), 4.11 (t, J=4 Hz, 1H), 4.19 (t, J=4 Hz, 1H), 4.24 (s, 1H), 4.46 (s, 2H), 4.61 (s, 2H), 7.08 (s, 1H), 7.54 (d, J=8 Hz, 1H), 7.63-7.67 (m, 1H), 7.93-7.95 (m, 1H), 8.74 (s, 1H), 10.52 (s, 1H); HRMS(ESI) m/z: C$_{20}$H$_{18}$ClFN$_3$O$_4$, calculated 432.1126 [M+H]$^+$, found 432.1125 [M+H]$^+$.

Example 41

N-(3-Ethynylphenyl)-5-((tetrahydrofuran-2-yl)methoxy)-2,3-dihydro-[1,4]dioxino[2,3-f]quinazolin-10-amine (I-41)

Step 1 to 5 is the same as in example 40;

Step 6: Preparation for N-(3-Ethynylphenyl)-5-((tetrahydrofuran-2-yl)methoxy)-2,3-dihydro-[1,4]dioxino[2,3-f]quinazolin-10-amine

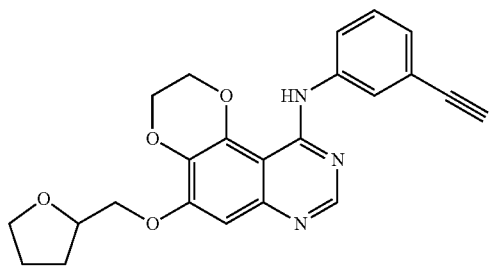 [SMILES: C#Cc1cccc(Nc2ncnc3cc(OCC4CCCO4)c4c(c23)OCCO4)c1]

To a solution of 10-Chloro-5-((tetrahydrofuran-2-yl)methoxy)-2,3-dihydro-[1,4]dioxino[2,3-f]quinazoline (0.15 g, 0.35 mmol) in isopropanol (3 mL) was added 3-ethynylaniline (45 mg, 0.38 mmol). The solution was stirred at 80° C. for 4 hours. After cooling to ambient temperature, the solution was concentrated to obtain a yellow solid which was purified by column chromatography on silicon gel (dichloromethane:methanol=100:1) to obtain a yellow solid (0.095 g, yield=45%). $^1$H NMR (DMSO-d$_6$, 400 MHz, δ ppm): 1.72-2.04 (m, 4H), 3.71 (t, J=8.0 Hz, 1H), 3.82 (d, J=4.0 Hz, 1H), 4.10 (s, 1H), 4.25 (s, 1H), 4.26-4.29 (m, 2H), 4.45 (s, 2H), 4.62 (s, 2H), 7.06 (s, 1H), 7.39-7.46 (m, 2H), 7.48-7.82 (m, 2H), 8.71 (s, 1H), 10.45 (s, 1H); HRMS(ESI) m/z: C$_{23}$H$_{22}$N$_3$O$_4$, calculated 404.1610 [M+H]$^+$, found 404.1611 [M+H]$^+$.

Example 42

4-((3-Chloro-4-fluorophenyl)amino)-6-(3-morpholinopropyl)-6H-[1,4]oxazino[3,2-g]quinazolin-7(8H)-one (II-1)

Step 1: Preparation for methyl 4-hydroxy-3-nitrobenzoate

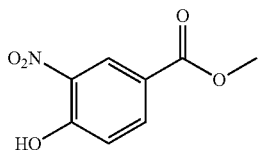

To a solution of 4-hydroxy-3-nitrobenzoic acid (9.15 g, 0.05 mol) in methanol (100 mL) was added H$_2$SO$_4$ (98%, 5 mL). The mixture was stirred at 80° C. for 10 hours, then concentrated, diluted with water (500 mL), filtered, and dried to obtain a yellow solid (8.6 g, 87% yield). $^1$H NMR (CDCl$_3$, 400 MHz, δ ppm): 3.96 (s, 1H), 7.23-7.28 (m, 1H), 8.25 (d, J=4.4 Hz, 1H), 8.84 (s, 1H), 10.90 (s, 1H).

Step 2: Preparation for methyl 4-(2-ethoxy-2-oxoethoxy)-3-nitrobenzoate

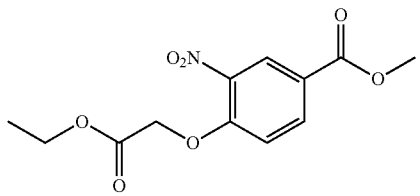 [SMILES: CCOC(=O)COc1ccc(C(=O)OC)cc1[N+](=O)[O-]]

To a solution of methyl 4-hydroxy-3-nitrobenzoate (9.85 g, 0.05 mol) in DMF (100 mL) was added K$_2$CO$_3$ (20.7 g, 0.15 mol) with stirring for 15 minutes, then to the solution were added ethyl 2-bromoacetate (6.65 mL, 0.06 mol) and potassium iodide (0.165 g, 0.001 mol) with stirring at 80° C. for 10 hours. After that the mixture was diluted with water (1000 mL), filtered, washed by water and dried to obtain a yellow solid (12.7 g, 90% yield). $^1$H NMR (CDCl$_3$, 400 MHz, δ ppm): 1.29 (t, J=7.0 Hz, 3H), 3.94 (s, 3H), 4.27 (q, J=7.2, 2H), 4.85 (s, 2H), 7.01 (d, J=4.4 Hz, 1H), 8.18-8.20 (m, 1H), 8.53 (s, 1H).

Step 3: Preparation for methyl 3-oxo-3,4-dihydro-2H-benzo[b][1,4]oxazine-6-carboxylate

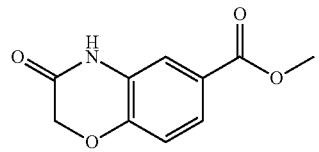

To a solution of methyl 4-(2-ethoxy-2-oxoethoxy)-3-nitrobenzoate (2.83 g, 0.01 mol) in acetic acid (50 mL) was added iron powder (2.24 g, 0.04 mol) with stirring at 60° C. for 6 hours and then the mixture was filtered. The resulting filtrate was washed with K$_2$CO$_3$ solution, dried and concentrated to obtain a white solid (1.3 g, 65% yield). $^1$H NMR (CDCl$_3$, 400 MHz, δ ppm): 3.39 (s, 3H), 4.72 (s, 2H), 7.02 (t, J=4.2 Hz, 1H), 7.57 (s, 1H), 7.71-7.73 (m, 1H), 8.63 (s, 1H).

Step 4: Preparation for methyl 7-nitro-3-oxo-3,4-dihydro-2H-benzo[b][1,4]oxazine-6-carboxylate

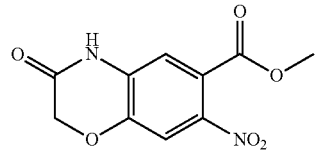 [SMILES: COC(=O)c1cc2c(cc1[N+](=O)[O-])OCC(=O)N2]

To a solution of methyl 3-oxo-3,4-dihydro-2H-benzo[b][1,4]oxazine-6-carboxylate (10.35 g, 0.05 mol) in nitromethane (100 mL) was added nitrosonitric acid (0.66 mL, 0.015 mmol) in small portions at 0° C. with stirring. After stirred at ambient temperature for 40 minutes, an additional nitromethane (3.96 mL, 0.09 mol) was added. The solution was stirred at 35° C. for 1 hour and then ambient temperature 4 hours. Most of the nitromethane was evaporated and the resulting solution was diluted with water (500 mL). The mixture was filtered and dried to obtain a yellow solid (6.9 g, 55% yield). $^1$H NMR (CDCl$_3$, 400 MHz, δ ppm): 3.82 (s, 3H), 4.77 (s, 2H), 7.21 (s, 1H), 7.64 (s, 1H), 11.30 (s, 1H).

Step 5: Preparation for methyl 4-(3-morpholinopropyl)-7-nitro-3-oxo-3,4-dihydro-2H-benzo[b][1,4]oxazine-6-carboxylate

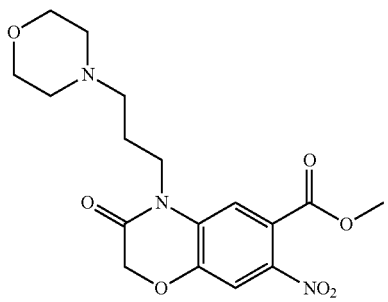

To a solution of methyl 7-nitro-3-oxo-3,4-dihydro-2H-benzo[b][1,4]oxazine-6-carboxylate (2.52 g, 0.01 mol) in DMF (50 mL) was added K$_2$CO$_3$ (4.14 g, 0.03 mol) with stirring for 15 minutes. And then to the solution were added 4-(3-chloropropyl)morpholine (2.45 g, 0.015 mol) and potassium iodide (0.165 g, 0.001 mol) with stirring at 80° C. for 10 hours. After that the mixture was diluted with water (300 mL), filtered, washed by water and dried to obtain a yellow solid (2.6 g, 75% yield). $^1$H NMR (CDCl$_3$, 400 MHz, δ ppm): 1.84 (m, J=6.8 Hz, 2H), 2.37-2.40 (m, 6H), 3.68 (t, J=4.4 Hz, 4H), 3.89 (s, 3H), 4.05 (t, J=7.2 Hz, 2H), 4.71 (s, 2H), 7.39 (s, 1H), 7.52 (s, 1H).

Step 6: Preparation for methyl 7-amino-4-(3-morpholinopropyl)-3-oxo-3,4-dihydro-2H-benzo[b][1,4]oxazine-6-carboxylate

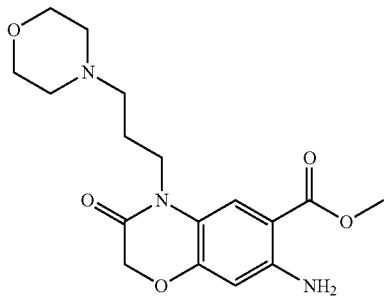 [SMILES: COC(=O)c1cc2c(cc1[N+](=O)[O-])OCC(=O)N2CCCN1CCOCC1]

To a solution of methyl 4-(3-morpholinopropyl)-7-nitro-3-oxo-3,4-dihydro-2H-benzo[b][1,4]oxazine-6-carboxylate (3.79 g, 0.01 mol) in methanol was added Pd/C (5%, 0.1 g). The solution was stirred under H$_2$ atom sphere at ambient temperature for 4 hours, filtered and evaporated in vacuum to obtain a pale solid (3.6 g, 95% yield). $^1$H NMR (CDCl$_3$, 400 MHz, δ ppm): 1.86 (m, J=7.2 Hz, 2H), 2.44 (m, 6H), 3.73 (t, J=4.6 Hz, 4H), 3.88 (s, 3H), 4.00 (t, J=7.4 Hz, 2H), 4.59 (s, 2H), 5.70 (s, 2H), 6.29 (s, 1H), 7.50 (s, 1H).

Step 7: Preparation for 6-(3-Morpholinopropyl)-3H-[1,4]oxazino[3,2-g]quinazoline-4,7(6H,8H)-dione

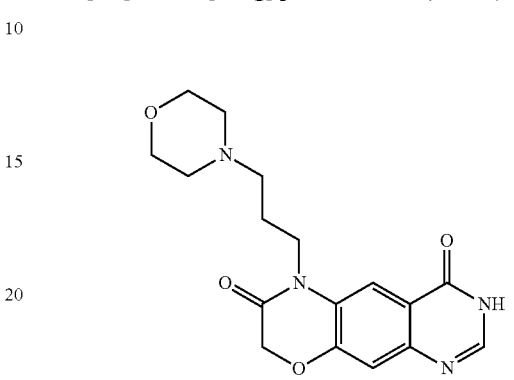

A solution of methyl 7-amino-4-(3-morpholinopropyl)-3-oxo-3,4-dihydro-2H-benzo[b][1,4]oxazine-6-carboxylate (3.49 g, 0.01 mol) in formamide (50 mL) was stirred at 150° C. for 20 hours. After that the solution was evaporated in vacuum, washed with EA and filtered to obtain a pale solid. (3.1 g, 90% yield). ESI-MS (m/z): 345.2 [M+H]$^+$.

Step 8: Preparation for 4-Chloro-6-(3-morpholinopropyl)-6H-[1,4]oxazino[3,2-g]quinazolin-7(8H)-one

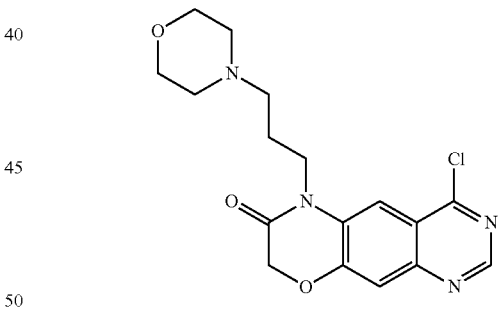

A solution of 6-(3-morpholinopropyl)-3H-[1,4]oxazino[3,2-g]quinazoline-4,7(6H,8H)-dione (1.8 g, 0.005 mol) in POCl$_3$ (20 mL) was stirred at 110° C. for 10 hours. After cooling to ambient temperature, the solution was quenched with a large amount of ice, adjusted pH to 9 with K$_2$CO$_3$, extracted with ethyl acetate and washed with saturated brine. The obtained organic layer was dried over magnesium sulfate, filtered and concentrated to obtain a crude product as a yellow solid which was purified by column chromatography on silicon gel (dichloromethane:methanol=100:1) to obtained a yellow solid (0.9 g, yield=50%). $^1$NMR (CDCl$_3$, 400 MHz, δ ppm): 1.87 (t, J=8.0 Hz, 2H), 2.36-2.47 (m, 6H), 3.70 (t, J=4.0 Hz, 4H), 4.20 (t, J=7.8 Hz, 2H), 4.86 (s, 2H), 7.59 (s, 1H), 7.75 (s, 1H), 8.96 (s, 1H). ESI-MS (m/z): 363.4 [M+H]$^+$ Step 9: Preparation for 4-((3-Chloro-4-fluorophenyl)amino)-6-(3-morpholinopropyl)-6H-[1,4]oxazino[3,2-g]quinazolin-7(8H)-one

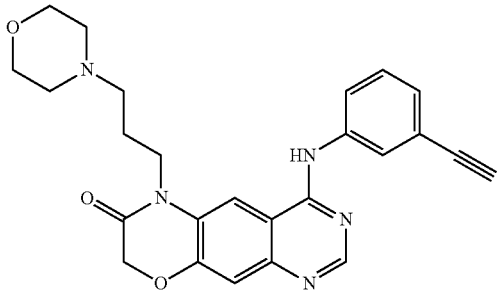 [SMILES: C#Cc1cccc(Nc2ncnc3cc4c(cc23)N(CCCN2CCOCC2)C(=O)CO4)c1]

To a solution of 10-Chloro-5-(((tetrahydrofuran-2-yl)methoxy)-2,3-dihydro-[1,4]dioxino[2,3-f]quinazoline (3.62 g, 0.01 mmol) in isopropanol (30 mL) was added 3-ethynylaniline (2.55 g, 0.015 mol). The solution was stirred at reflux for 6-8 hours, cooled to room temperature, filtered to obtain a white solid which was purified by column chromatography on silicon gel (dichloromethane:methanol=10:1) to obtain a white solid. (2.7 g, yield=60%). $^1$H NMR (CDCl$_3$, 400 MHz, δ ppm): 1.98 (t, J=7.6 Hz, 2H), 2.51-2.53 (m, 6H), 3.72 (t, J=4.0 Hz, 4H), 4.18 (t, J=7.8 Hz, 2H), 4.74 (s, 2H), 7.18 (t, J=4.4 Hz, 1H), 7.44 (s, 1H), 7.60 (q, J=5.2 Hz, 1H), 7.65 (s, 1H), 7.90 (q, J=6.4 Hz, 1H), 8.32 (s, 1H), 8.65 (s, 1H); HRMS (ESI) m/z: C$_{23}$H$_{24}$ClFN$_5$O$_3$, calculated 472.1552 [M+H]$^+$, found 472.1549 [M+H]$^+$.

Example 43

4-((3-Chloro-4-fluorophenyl)amino)-6-(3-morpholinopropyl)-6H-[1,4]oxazino[3,2-g]quinazolin-7(8H)-one (II-2)

Step 1 to 8 is the same as in example 42;

Step 9: Preparation for 4-((3-Chloro-4-fluorophenyl)amino)-6-(3-morpholinopropyl)-6H-[1,4]oxazino[3,2-g]quinazolin-7(8H)-one

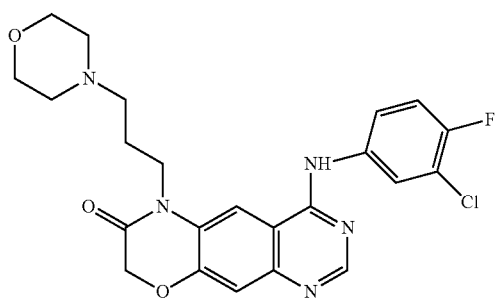 [SMILES: O=C1COc2cc3ncnc(Nc4ccc(F)c(Cl)c4)c3cc2N1CCCN1CCOCC1]

To a solution of 10-Chloro-5-(((tetrahydrofuran-2-yl)methoxy)-2,3-dihydro-[1,4]dioxino[2,3-f]quinazoline (3.62 g, 0.01 mmol) in isopropanol (30 mL) was added 3-Chloro-4-fluoroaniline (2.2 g, 0.015 mol). The solution was stirred at reflux for 6-8 hours, cooled to room temperature, filtered to obtain a white solid which was purified by column chromatography on silicon gel (dichloromethane:methanol=10:1) to obtain a white solid. (1.3 g, yield=28%). $^1$H NMR (CDCl$_3$, 400 MHz, δ ppm): 1.98 (t, J=7.6 Hz, 2H), 2.51-2.53 (m, 6H), 3.72 (t, J=4.0 Hz, 4H), 4.18 (t, J=7.8 Hz, 2H), 4.74 (s, 2H), 7.18 (t, J=4.4 Hz, 1H), 7.44 (s, 1H), 7.60 (q, J=5.2 Hz, 1H), 7.65 (s, 1H), 7.90 (q, J=6.4 Hz, 1H), 8.32 (s, 1H), 8.65 (s, 1H); HRMS (ESI) m/z: C$_{23}$H$_{24}$ClFN$_5$O$_3$, calculated 472.1552 [M+H]$^+$, found 472.1549 [M+H]$^+$.

Example 44

4-((3-Chloro-4-methylphenyl)amino)-6-(3-morpholinopropyl)[1,4]oxazino[3,2-g]quinazolin-7(8H)-one (II-3)

Step 1 to 8 is the same as in example 42;

Step 9: Preparation for 4-((3-Chloro-4-methylphenyl)amino)-6-(3-morpholinopropyl)-6H-[1,4]oxazino[3,2-g]quinazolin-7(8H)-one

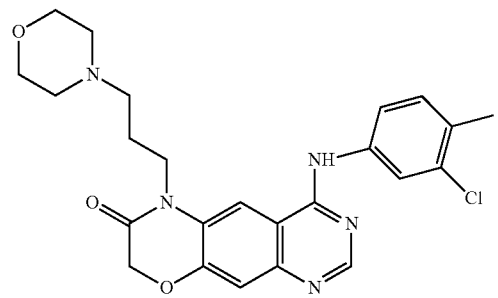 [SMILES: Cc1ccc(Nc2ncnc3cc4c(cc23)N(CCCN2CCOCC2)C(=O)CO4)cc1Cl]

To a solution of 10-Chloro-5-(((tetrahydrofuran-2-yl)methoxy)-2,3-dihydro-[1,4]dioxino[2,3-f]quinazoline (3.62 g, 0.01 mmol) in isopropanol (30 mL) was added 3-chloro-4-methylaniline (2.2 g, 0.015 mol). The solution was stirred at reflux for 6-8 hours, cooled to room temperature, filtered to obtain a white solid which was purified by column chromatography on silicon gel (dichloromethane:methanol=10:1) to obtain a white solid. (0.9 g, yield=19%). $^1$H NMR (DMSO-d$_6$, 400 MHz, δ ppm): 2.11 (t, J=7.4 Hz, 2H), 2.34 (s, 3H), 3.31-3.79 (m, 6H), 3.89 (q, J=4.0 Hz, 4H), 4.33 (t, J=6.8 Hz, 2H), 4.86 (s, 2H), 7.31-7.37 (m, 2H), 7.85 (q, J=4.0 Hz, 1H), 8.10 (s, 1H), 8.46 (s, 1H), 8.54 (s, 1H), 10.30 (s, 1H); HRMS(ESI) m/z: C$_{24}$H$_{27}$ClN$_5$O$_3$, calculated 468.1802 [M+H]$^+$, found 468.1797 [M+H]$^+$.

Example 45

4-((3-Methoxyphenyl)amino)-6-(3-morpholinopropyl)-6H-[1,4]oxazino[3,2-g]quinazolin-7(8H)-one (II-4)

Step 1 to 8 is the same as in example 42;

Step 9: Preparation for 4-((3-Methoxyphenyl)amino)-6-(3-morpholinopropyl)-6H-[1,4]oxazino[3,2-g]quinazolin-7(8H)-one

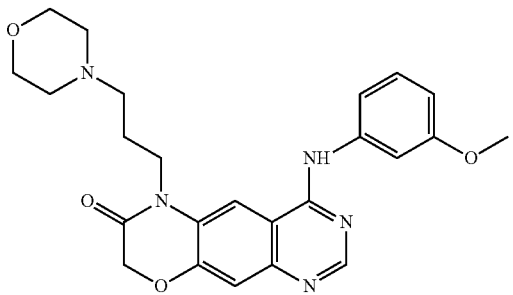 [SMILES: COc1cccc(Nc2ncnc3cc4c(cc23)N(CCCN2CCOCC2)C(=O)CO4)c1]

To a solution of 10-Chloro-5-((tetrahydrofuran-2-yl)methoxy)-2,3-dihydro-[1,4]dioxino[2,3-f]quinazoline (3.62 g, 0.01 mmol) in isopropanol (30 mL) was added 3-Methoxyaniline (1.85 g, 0.015 mol). The solution was stirred at reflux for 6-8 hours, cooled to room temperature, filtered to obtain a white solid which was purified by column chromatography on silicon gel (dichloromethane:methanol=10:1) to obtain a white solid. (1.2 g, yield=26%). (0.065 g, yield=58%). $^1$H NMR (DMSO-$d_6$, 400 MHz, δ ppm): 2.09 (t, J=7.4 Hz, 2H), 3.09-3.31 (m, 6H), 3.78 (m, 7H), 4.30 (t, J=8.0 Hz, 2H), 4.85 (s, 2H), 6.98 (q, J=4.0 Hz, 2H), 7.28 (s, 1H), 7.70 (q, J=4.0 Hz, 2H), 8.42 (q, J=8.0 Hz, 2H), 10.22 (s, 1H); HRMS (ESI) m/z: $C_{24}H_{28}N_5O_4$, calculated 450.2141 [M+H]$^+$, found 450.2140 [M+H]$^+$.

Example 46

4-((3,4-Dimethoxyphenyl)amino)-6-(3-morpholinopropyl)-6H-[1,4]oxazino[3,2-g]quinazolin-7(8H)-one (II-5)

Step 1 to 8 is the same as in example 42;

Step 9: Preparation for 4-((3,4-Dimethoxyphenyl)amino)-6-(3-morpholinopropyl)-6H-[1,4]oxazino[3,2-g]quinazolin-7(8H)-one

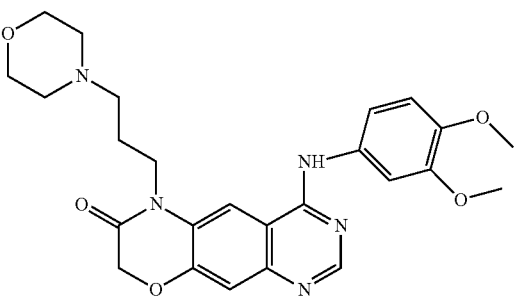 [SMILES: COc1ccc(Nc2ncnc3cc4c(cc23)N(CCCN2CCOCC2)C(=O)CO4)cc1OC]

To a solution of 4-chloro-6-(3-morpholinopropyl)-6H-[1,4]oxazino[3,2-g]quinazolin-7(8H)-one (3.62 g, 0.01 mol) in isopropanol (30 mL) was added 3,4-dimethoxyaniline (2.3 g, 0.015 mol). The solution was stirred at 80° C. for 4 hours. After cooling to ambient temperature, the solution was concentrated to obtain a yellow solid which was purified by column chromatography on silicon gel (dichloromethane:methanol=10:1) to obtained a yellow solid (1.1 g, yield=22%). $^1$H NMR (DMSO-$d_6$, 400 MHz, δ ppm): 2.11 (t, J=7.2 Hz, 2H), 3.14-3.27 (m, 6H), 3.78 (m, 10H), 4.32 (s, 2H), 4.87 (s, 2H), 6.98 (q, J=4.0 Hz, 1H), 7.30 (s, 1H), 7.41 (q, J=4.0 Hz, 1H), 7.55 (s, 1H), 8.50 (q, J=4.0 Hz, 1H), 10.41 (s, 1H); HRMS (ESI) m/z: $C_{25}H_{30}N_5O_5$, calculated 480.2247 [M+H]$^+$, found 480.2244 [M+H]$^+$. M.P.: 248~249° C.

Example 47

Determination of the Compound Inhibitory Activity Against EGFR Kinase

The inhibitory activity of compounds in formula (I) and (II) were determined using Kinase-Glo luminescent kinase assay. The receptor tyrosine kinase EGFR was tested and Gefitinib, a known EGFR inhibitor, was chosen as the positive control compound. The method is detailed below:

The sample compounds were dissolved in DMSO and diluted it to 500 μM concentration with DMSO and transferred to a dose plate. The compounds were serially diluted with DMSO in 5 fold concentration. Then each concentration was diluted 10-fold with the reaction buffer to get a 10× final concentration. Transfer the compounds with concentrations ranging from 0.003 μM to 50 μM to EGFR assay plate to determine their kinase activity with a dose of 1 μL/well.

The positive control compound Gifitinib was dissolved in DMSO as 10 mM stock solution and diluted it to 100 μM concentration with DMSO. The control compound was serially diluted with DMSO in 5 fold concentration. Then each concentration was diluted 10-fold with the reaction buffer to get a 10× final concentration. Transfer the positive control compound with concentrations ranging from 0.00064 μM to 10 μM to EGFR assay plate to determine their kinase activity with a dose of 1 μL/well.

For the HPE (hundred percent effect: No kinase and no compound, but containing ATP, substrate and 1% DMSO) and ZPE (zero percent effect: No compound but containing kinase, ATP, substrate and 1% DMSO) wells, dilute 2 μL DMSO 10-fold with reaction buffer to obtain 10% DMSO solution. Then transfer it to the assay plat, 1 μL/well. The positive control wells contain kinase, ATP, substrate and positive control compound in different concentrations. The sample compound wells contain kinase, ATP, substrate and the compounds to be tested in different concentrations.

Preparation of the reagents in need: 4×ATP: dilute ATP 4 times with assay buffer to obtain a working solution; 4× substrate: dilute Poly (glucose: tyrosine) 4 times with assay buffer to obtain a working solution; 2.5×EGFR kinase: dilute EGFR kinase 2.5 times with assay buffer to obtain a working solution.

Kinase reaction: Add 10× compounds to the assay plate in a 384-well plate layout, 1 μL/well. For the HPE and ZPE wells, equal volume (1 μL/well) of 10% DMSO was added to the 384-well assay plate; Add 2.5×EGFR kinase into the assay plate in 384-well plate layout, 4 μL/well. For HPE and ZPE wells, an equal volume (4 μL/well) of assay buffer was added to the 384-well assay plate; Centrifuge the assay plate with 1000 rpm for 1 min to mix them; Pre-incubate the assay plate for 30 min at 30° C.; Mix equal volume of 4×ATP and 4× substrate to obtain 2×ATP-substrate mixture which serves as a reaction mixture for the determination of EGFR activity; Add 2×ATP-substrate mixture to the assay plate, 5 μL/well; Centrifuge the assay plate at 1000 rpm for 1 min to mix them; Incubate the assay plate for one hour at 30° C.; Add Kinase glo plus was to each well (10 μL/well), and then incubated the assay plate for 20 min at 27° C.; Read luminescence signal with Envision plate reader.

Raw data analysis: The raw data was analyzed by Prism 5.0 and the rate of inhibition was calculated by the following formula: Compound inhibition rate=("compound" reading−ZPE)/(HPE−ZPE)*100%.

TABLE 1

Testing results for EGFR tyrosine kinase inhibitory activity

| Compound No. | EGFR (WT) $IC_{50}$ nM | EGFR (T790M) $IC_{50}$ nM |
|---|---|---|
| I-1 | <1000 | <1000 |
| I-2 | <100 | <1000 |
| I-3 | <200 | <1000 |
| I-4 | <100 | <1000 |
| I-5 | <300 | <1000 |
| I-6 | <400 | <1000 |
| I-7 | <50 | <50 |
| I-8 | <50 | <50 |
| I-9 | <1000 | <1000 |
| I-10 | <50 | <1000 |
| I-11 | <100 | <1000 |
| I-12 | <50 | <1000 |
| I-13 | <500 | <1000 |
| I-14 | <1000 | <1000 |
| I-15 | <1000 | <1000 |
| I-16 | <300 | <300 |
| I-17 | <300 | <1000 |
| I-18 | <300 | <1000 |
| I-19 | <300 | <1000 |
| I-20 | <1000 | <1000 |
| I-21 | <100 | <1000 |
| I-22 | <100 | <1000 |
| I-23 | <50 | <100 |
| I-24 | <50 | <300 |
| I-25 | <100 | <300 |
| I-26 | <100 | <300 |
| I-27 | <200 | <1000 |
| I-28 | <50 | <1000 |
| I-29 | <50 | <1000 |
| I-30 | <50 | <50 |
| I-31 | <50 | <50 |
| I-32 | <200 | <1000 |
| I-33 | <200 | <1000 |
| I-34 | <50 | <50 |
| I-35 | <50 | <50 |
| I-36 | <50 | <50 |
| I-37 | <50 | <50 |
| I-38 | <50 | <50 |
| I-39 | <50 | <100 |
| I-40 | <50 | <1000 |
| I-41 | <50 | <100 |
| II-1 | <50 | <300 |
| II-2 | <200 | <1000 |
| II3 | <200 | <1000 |
| II-4 | <200 | <1000 |
| II-5 | <200 | <1000 |
| Gefitinib | 6.3 | 22.47 |

Example 48

Cell Assay of EGFR Activity

The anti-proliferative activity was determined using cell-counting kit-8 assay (Dojindo, Japan). H358 and A549 cells lines were seeded at a density of 8000 cells/well and 3000 cells/well respectively in 96-well microtiter plates and were incubated at 37° C. overnight in a humidified incubator containing 5% $CO_2$. Cells were dosed with compounds at final concentrations ranging from 0.025 to 80 μM in each well of the plate. Three groups were set up, including compound group to be tested, blank control group, positive control group (gefitinib). Compound preparation method: dissolve compounds in DMSO and gradually dilute compounds to 66 μmol/L in concentration; then dilute the solutions serially in 4-fold with culture fluid to get 6 different concentrations for each compound, 4 wells per concentration and 200 μl per well. Note: DMSO should be less than 2% in the highest concentration of compound solution, a DMSO control group should be set up if DMSO is higher than 2%.

The 96-well plate was incubated in cell incubator for 72 hours. The culture fluid was then removed and 100 μl/well of PBS buffer was added. 10 μl/well of CCK-8 solution was added and the assay plate was incubated in the cell incubator for 1 hour. Cell survival was determined by measuring the absorbance at 470 nm using a microplate reader. A calibration curve was prepared using the average data of the 4 wells for each concentration that contain the number of viable cells to determine the $IC_{50}$ of the target compounds.

TABLE 2

Cell assay of EGFR activity

| Compound No. | H358 ($IC_{50}$ μM) | A549 ($IC_{50}$ μM) |
|---|---|---|
| I-7 | 6.92 | 11.61 |
| I-8 | 5.54 | 6.08 |
| I-16 | 17.48 | 17.51 |
| I-21 | 1.47 | 6.42 |
| I-22 | >20 | >20 |
| I-23 | 12.99 | 15.14 |
| I-24 | 8.58 | 9.69 |
| I-25 | 10.64 | 10.36 |
| I-31 | <50 | <50 |
| I-30 | 5.93 | 13.88 |
| I-31 | 7.35 | 9.33 |
| I-33 | 9.64 | 12.1 |
| I-34 | 22.74 | 16.09 |
| I-35 | 8.89 | 10.54 |
| I-36 | 7.41 | 11.95 |
| I-37 | 11.64 | 12.09 |
| I-39 | 6.10 | 10.18 |
| I-41 | 9.51 | 11.47 |
| II-1 | 13.46 | 7.51 |
| II-2 | 13.49 | 5.58 |
| Gefitinib | 14.66 | 9.28 |

Pharmaceutical Uses, Formulations, Administration

Pharmaceutical Uses and Indications

This invention provides compounds having biological properties which make them of beneficial for treating or ameliorating diseases in which kinases may be involved. For instance, a number of compounds of this invention have been shown to inhibit tyrosine kinase activity of EGFR and ErbB2, among other tyrosine kinases which are believed to mediate the growth, development and/or metastasis of cancer. A number of compounds of the invention have also been found to possess potent in vitro activity against cancer cell lines, including H358 cells and A549 cells.

Such compounds are thus beneficial for the treatment of cancers, including both primary and metastatic cancers, including solid tumors as well as cancers which are resistant to other therapies, including other therapies involving the administration of kinase inhibitors such as Tarceva or Iressa.

Such cancers include, among others, cancers of the breast, cervix, colon and rectum, lung, ovaries, pancreas, prostate, head and neck, gastrointestinal stroma, as well as diseases such as melanoma, multiple myeloma, non-Hodgkin's lymphoma, melanoma, gastric cancers, including cases which are resistant to one or more other therapies, including among others, Tarceva or Iressa.

Resistance to various anticancer agents can arise from one or more mutations in a mediator or effector of the cancer (e.g., mutation in a kinase such as EGFR) which correlate with alteration in the protein's drug binding properties, phosphate binding properties, protein binding properties, autoregulation or other characteristics. For example, in the case of EGFR, T790M mutation is believed to decrease the binding affinity of Gifitinib.

Again, compounds of this invention, both as monotherapies and in combination therapies, will be useful against non-small-cell lung cancer (NSCLC), breast cancer, and other cancers, including those which are resistant in whole or part to other anticancer agents, specifically including Tarceva, Iressa, and other kinase inhibitors, and specifically including non-small-cell lung-cancer involving one or more mutations in EGFR, within or outside the kinase domain, including but not limited to those noted in any of the foregoing publications.

Pharmaceutical Methods

The method of the invention comprises administering to a subject in need a therapeutically effective amount of a compound of the invention.

A "therapeutically effective amount" is that amount effective for detectable killing or inhibition of the growth or spread of cancer cells; the size or number of tumors; or other measures of the level, stage, progression or severity of the cancer. The exact amount required will vary from subject to subject, depending on the species, age, and general condition of the subject, the severity of the disease, the particular anticancer agent, its mode of administration, combination treatment with other therapies, and so on.

The anticancer compounds of the invention are preferably formulated in dosage unit form for ease of administration and uniformity of dosage. The phrase "dosage unit form" as used herein refers to a physically discrete unit of anticancer agent appropriate for the patient to be treated. The total daily usage of the compound and compositions of the present invention will be determined by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of this invention.

Furthermore, after formulation with an appropriate pharmaceutically acceptable carrier in a desired dosage, the compositions of this invention can be administered to humans and other animals orally, rectally, parenterally, intracisternally, intravaginally, intraperitoneal, topically (as by transdermal patch, powders, ointments, or drops), sublingually, bucally, as an oral or nasal spray, or the like. The effective systemic dose of the compound will typically be in the range of 0.01 to 500 mg of compound per kg of patient body weight, preferably 0.1 to 125 mg/kg, and in some cases 1 to 25 mg/kg, administered in single or multiple doses. Generally, the compound may be administered to patients in need of such treatment in a daily dose range of about 50 to about 2000 mg per patient Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. It may be administered daily for a period of days (e.g. 1-30 days) without administration of the compound, repeated indefinitely or for a given number of repetitions, e.g. 4-10 cycles. As an example, a compound of the invention may be administered daily for 5 days, then discontinued for 9 days, then administered daily for another 5-day period, then discontinued for 9 days, and so on, repeating the cycle indefinitely, or for a total of 4-10 times.

The amount of compound which will be effective in the treatment or prevention of a particular disorder or condition will depend in part on well-known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well-known factors, including route of administration, and the age, body weight, sex and general health of the individual; the nature, severity and clinical stage of the disease; the use (or not) of concomitant therapies; and the nature and extent of genetic engineering of cells in the patient.

The effective dosage of the compound of this invention may vary depending upon the particular compound utilized, the mode of administration, the condition, and severity thereof of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of this invention is used as part of a combination regimen, dosages of each of the components of the combination are administered during a desired treatment period. The components of the combination may be administered at the same time; either as a unitary dosage form containing both components, or as separate dosage units; the components of the combination can also be administered at different times during a treatment period, or one may be administered as a pretreatment for the other.

Compounds of Invention

Compounds of present invention can exist in free form for treatment, or where appropriate, as a pharmaceutically acceptable salt or another derivative. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates, and other types of compounds, are well known in the art. The salts can be prepared in situ during the isolation and purification of the compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydro bromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methane-sulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkylsulfonate and aryl sulfonate.

Additionally, the term "pharmaceutically acceptable ester" refers preferably to esters which hydrolyze in vivo and include those that break down readily in the human body to leave the parent compound or a salt thereof. Suitable ester groups include those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates. Obviously, esters can be formed with a hydroxy I or carboxylic acid group of the compound of the invention.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood.

Compositions

Compositions are provided which comprise any one of the compounds described herein (or a prodrug, pharmaceutically acceptable salt or other pharmaceutically acceptable derivative thereof), and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. TARCEVA or other kinase inhibitors, interferon, bone marrow transplant, farnesyltransferase inhibitors, bisphosphonates, thalidomide, cancer vaccines, hormonal therapy, antibodies, radiation, etc). For example, additional therapeutic agents for inclusion in a pharmaceutical composition with a compound of this invention may be another one or more anticancer agents.

As described herein, the compositions of the present invention comprise a compound of the invention together with a pharmaceutically acceptable carrier includes all solvents, diluents, or other vehicle, dispersion or suspension aids, surface active agents, isotonic agents, thickening or emulsifying agents, preservatives, solid binders, lubricants and the like, as suited to the particular dosage form. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also includes a class of compositions comprising the active compounds of this invention in connection with one or more pharmaceutically-acceptable carriers and/or diluents and/or adjuvants (collectively referred to herein as "carrier" materials). The active compounds of the present invention may be administered by any suitable route, preferably in the form of a pharmaceutical composition adapted to such a route, and in a dose effective for the treatment intended. The compounds and compositions of the present invention may be administered orally, mucosally, topically, rectally, pulmonarily, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals. For oral administration, the pharmaceutical composition may be in the form of a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

The active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. In the case of skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% w/w of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% of a polyhydric alcohol such as propylene glycol, butane-1,3-diol, mannitol, sorbitol, glycerol, polyethylene glycol and mixtures thereof. The topical formulation may include a compound which enhances absorption or penetration of the active ingredient through the skin or other affected areas. Examples of such dermal penetration enhancers include dimethylsulfoxide and related analogs.

The compounds can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The oily phase of the emulsions of this invention may be constituted from known ingredients in a known manner.

For an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glycerylmonostearate, sodium lauryl sulfate, glyceryldistearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyloleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used. Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w. Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables. For pulmonary administration, the pharmaceutical composition may be administered in the form of an aerosol or with an inhaler including dry powder aerosol. Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an antivascular hyper proliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyper proliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-atocopHerol polyethylenegylcol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as U-, P-, and y-cyclodextrins, or chemically modified derivatives such as hydroxyalkyl, including 2 and 3-hydroxypropyl-cyclodextrins, or other solubilized derivatives may also be advantageously used to enhance delivery of compounds of the formulae described herein.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening, flavoring and/or coloring agents may be added. The pharmaceutical compositions may comprise formulations utilizing liposome or microencapsulation techniques, various examples of which can be found in the literatures.

The pharmaceutical compositions may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

Combinations

While the compounds of the invention can be administered as the sole active pharmaceutical agent, they can also be used in combination with one or more other compounds of the invention or with one or more other agents. When administered as a combination, the therapeutic agents can be formulated as separate compositions that are administered at the same time or sequentially at different times, or the therapeutic agents can be given as a single composition. The phrase "combination therapy", in referring to the use of a compound of this invention together with another pharmaceutical agent, means the coadministration of each agent in a substantially simultaneous manner as well as the administration of each agent in a sequential manner, in either case, in a regimen that will provide beneficial effects of the drug combination. Coadministration includes inter alia the simultaneous delivery, e.g., in a single tablet, capsule, injection or other dosage form having a fixed ratio of these active agents, as well as the simultaneous delivery in multiple, separate dosage forms for each agent respectively.

The administration of compounds of the present invention, thus, may be in conjunction with additional therapies known to those skilled in the art in the prevention or treatment of cancer, such as radiation therapy or cytostatic agents, cytotoxic agents, other anti-cancer agents and other drugs to ameliorate symptoms of the cancer or side effects of any of the drugs.

If formulated as a fixed dose, such combination products employ the compounds of this invention within the accepted dosage ranges. Compounds of this invention may also be administered sequentially with other anticancer or cytotoxic agents when a combination formulation is inappropriate. The invention is not limited in the sequence of administration; compounds of this invention may be administered prior to, simultaneously with, or after administration of the other anticancer or cytotoxic agent.

Currently, standard treatment of primary tumors consists of surgical excision, followed by either radiation or chemotherapy, and typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

The anti-cancer treatment described herein may be applied as a sole therapy or may involve, in addition to the compound of the invention, conventional surgery or radiotherapy or chemotherapy or immunotherapy. Such chemotherapy could be administered concurrently, simultaneously, sequentially or separately to treatment with the compound of the invention and may include one or more of the following categories of anti-tumor agents:

(1) antiproliferative/antineoplastic drugs and combinations thereof, as used in medical oncology, such as alkylating agents (for example czs-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(2) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5a-reductase such as finasteride;

(3) anti-invasion agents, for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline [AZD0530 (saracatinib); WO01/94341], N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med Chem., 2004, 47, 6658-6661) and bosutinib (SKI-606), and metalloproteinase inhibitors like marimastat, inhibitors of urokinase plasminogen activator receptor function or antibodies to Heparanase.

The above description is the preferred embodiment of this invention, it should be noted that, to those who skilled in this field, the further improvements and modifications may be made under the principle of this invention. These improvements or modifications should also be regarded as within the scope of this invention.

We claim:
1. A compound of N-substituted phenyl-5-substituted alkoxyl-2,3-dihydro-[1,4]dioxane[2,3-f]quinazolin-10-amine represented by structure formula (I), or a pharmaceutically acceptable salt or prodrug molecule thereof,

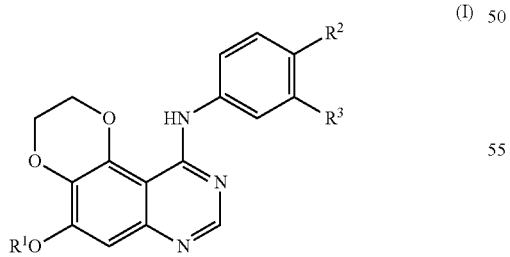

wherein
$R^1$ is selected from the group consisting of 1) —H, 2) $C_1$-$C_5$ alkyl or branched alkyl, 3) alkoxy or alkoxy substituted $C_1$-$C_5$ alkyl or branched alkyl, and 4) nitrogen-containing saturated heterocycle or nitrogen-containing saturated heterocycle substituted $C_1$-$C_5$ alkyl or branched alkyl;

$R^2$ is selected from the group consisting of 1) —H, 2) halogen, 3) aryl alkoxy, 4) $C_1$-$C_3$ alkyl, and 5) $C_1$-$C_3$ alkoxy or branched alkoxy;

$R^3$ is selected from the group consisting of 1) —H, 2) halogen, 3) $C_2$-$C_4$ unsaturated alkyl; 4) nitro, 5) cyano; and 6) $C_1$-$C_3$ alkoxy or branched alkoxy.

2. The compound according to claim 1, wherein $R^1$ is alkoxy selected from the group consisting of tetrahydrofuranyl alkoxy, tetrahydropyranyl alkoxy, dioxanyl alkoxy, morpholinyl alkoxy, $C_1$-$C_5$ alkoxy, and branched alkoxy.

3. The compound according to claim 1, wherein $R^2$ is Halogen selected from the group consisting of fluoride, chloride, and bromide.

4. The compound according to claim 1, wherein $R^3$ is Halogen selected from the group consisting of fluoride, chloride, and bromide.

5. A method for preparing a compound (I), comprising the following steps:

a) adding methyl 2-(2-chloroethoxy)-3,4-dihydroxybenzoate and potassium carbonate into N, N-dimethyl formamide (DMF) to form a mixture, then stirring the mixture at 60° C. for 2 hours, then cooling the mixture to room temperature, then pouring the mixture into ice water, then filtering the solution to obtain a compound of methyl 8-hydroxy-2,3-dihydrobenzo[b][1,4]dioxine-5-carboxylate represented by formula (III)

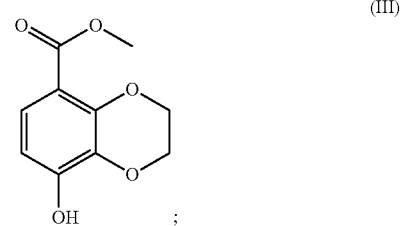

b) adding the compound of methyl 8-hydroxy-2, 3-dihydrobenzo[b][1,4]dioxine-5-carboxylate represented by formula (III), potassium carbonate and halogenated hydrocarbon with $R^1$ group or halogenated hydrocarbon obtained from reactive transformation of alcohol with $R^1$ group into a polar aprotic solvent to form a first solution, then stirring the first solution at 40-100° C. for 2-6 hours to obtain a compound of methyl 8-alkoxyl-2,3-dihydrobenzo[b][1,4]dioxine-5-carboxylate represented by formula (IV),

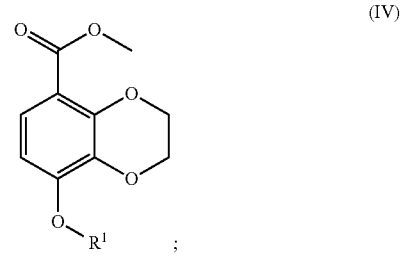

c) dissolving the compound of methyl 8-alkoxyl-2, 3-dihydrobenzo[b][1,4]dioxine-5-carboxylate represented by formula (IV) in glacial acetic acid to form a second solution, then dropwise adding a mix acid of fuming nitric acid and glacial acetic acid into the second solution at low temperature, then stirring the second solution for 1-2 hours, then pouring the second solution into ice water to separate-out solid, after separating and drying the solid, dissolving the solid in glacial acetic acid to form a third solution, then adding Zn powder to the third solution for reduction, then filtering and concentrating the third solution, then adding ethyl acetate to dissolve to form a fourth solution, then rinsing the fourth solution, then drying and concentrating the fourth solution, then performing separation on the fourth solution to obtain a compound of methyl 6-amino-8-alkoxyl-2, 3-dihydrobenzo[b][1,4]dioxine-5-carboxylate represented by formula (V),

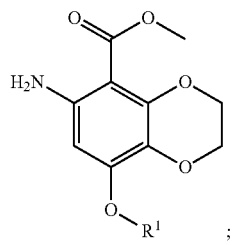
(V)

d) dissolving the compound of methyl 6-amino-8-alkoxyl-2,3-dihydrobenzo[b][1,4]dioxine-5-carboxylate represented by formula (V) in formamide to form a fifth solution, then heating up and stirring the fifth solution at 100-180° C. for 10-20 hours, then cooling the fifth solution to room temperature, then concentrating the fifth solution at a reduced pressure to obtain solid substance, then drying the solid substance, then adding the solid substance into phosphoryl trichloride for reaction at 80-130° C. for 12-24 hours to form a sixth solution, then cooling the sixth solution to room temperature, then pouring the sixth solution into an ice-water mixture, then adding potassium carbonate to adjust the PH of the sixth solution to 8, then extracting the sixth solution with ethyl acetate, then filtering and concentrating the solution to obtain a compound of 10-chloro-5-alkoxyl-2,3-dihydro-[1,4]dioxino[2,3-f] quinazoline represented by formula (VI),

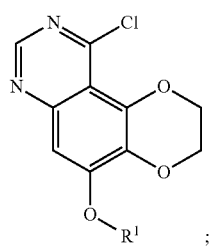
(VI)

e) dissolving the compound of 10-chloro-5-alkoxy-2, 3-dihydro-[1,4]dioxino[2,3-f]quinazoline represented by formula (VI) and 3, 4-disubstituted aniline in isopropanol to form a seventh solution, then stirring and heating up the seventh solution at 60-100° C. for 2-8 hours and then cooling the seventh solution to room temperature, then concentrating the seventh solution, then performing chromatographic separation on the seventh solution to obtain a compound of N-substituted phenyl-5-substituted alkoxyl-2,3-dihydro[1,4]dioxino [2,3-f]quinazolin-10-amine represented by formula (I)

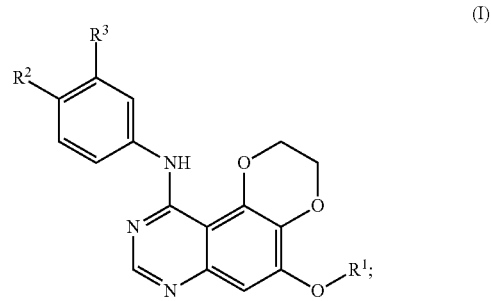
(I)

wherein
$R^1$ is selected from the group consisting of 1) —H, 2) $C_1$-$C_5$ alkyl or branched alkyl, 3) alkoxy or alkoxy substituted $C_1$-$C_5$ alkyl or branched alkyl, and 4) nitrogen-containing saturated heterocycle or nitrogen-containing saturated heterocycle substituted $C_1$-$C_5$ alkyl or branched alkyl;
$R^2$ is selected from the group consisting of 1) —H, 2) halogen, 3) aryl alkoxy, and 4) $C_1$-$C_3$ alkyl, 5) $C_1$-$C_3$ alkoxy or branched alkoxy;
$R^3$ is selected from the group consisting of 1) —H, 2) halogen, 3) $C_2$-$C_4$ unsaturated alkyl; 4) nitro, 5) cyano; and 6) $C_1$-$C_3$ alkoxy or branched alkoxy.

6. The compound according to claim 1, wherein $R^2$ is aryl alkoxy selected from the group consisting of fluoride benzyloxy, chloride benzyloxy, bromide benzyloxy, substituted benzyloxy, cyano benzyloxy, nitro benzyloxy, pyridylmethyl, $C_1$-$C_3$ alkyl substituted pyridylmethyl, fluoride pyridylmethyl, and chloride pyridylmethyl.

7. The compound according to claim 1, wherein $R^2$ is $C_1$-$C_3$ alkyl selected from the group consisting of methyl, ethyl, propyl, and isopropyl.

8. The compound according to claim 1, wherein $R^2$ is $C_1$-$C_3$ alkoxy or branched alkoxy selected from the group consisting of methoxy, ethoxy, propoxy, and isopropoxy.

9. The compound according to claim 1, wherein $R^3$ is $C_2$-$C_4$ unsaturated alkyl selected from the group consisting of ethenyl, propenyl, 1-butenyl, 2-butenyl, ethynyl, propynyl, 1-butynyl, and 2-butynyl.

10. The compound according to claim 1, wherein $R^3$ is $C_1$-$C_3$ alkoxy or branched alkoxy selected from the group consisting of methoxy, ethoxy, propoxy, and isopropoxy.

* * * * *